United States Patent
Saito

[19]

[11] Patent Number: 5,879,339

[45] Date of Patent: Mar. 9, 1999

[54] HUB FOR SYRINGE, CONNECTING STRUCTURE OF HUB, SYRINGE, PISTON, NEEDLE ASSEMBLY UNIT, CONNECTING STRUCTURE BETWEEN NEEDLE ASSEMBLY UNIT AND SYRINGE, SYRINGE ASSEMBLY AND METHOD OF ASSEMBLING SYRINGE ASSEMBLY

[76] Inventor: Yoshikuni Saito, Ooaza Kitanogami 1930, Kurobanemachi, Nasu-gun, Tochigi-Ken, Japan

[21] Appl. No.: 614,632

[22] Filed: Mar. 13, 1996

Related U.S. Application Data

[62] Division of Ser. No. 263,752, Jun. 22, 1994, abandoned.

[30] Foreign Application Priority Data

| Jun. 29, 1993 | [JP] | Japan | 5-184439 |
| Jul. 23, 1993 | [JP] | Japan | 5-202643 |
| Aug. 30, 1993 | [JP] | Japan | 5-237439 |
| Aug. 30, 1993 | [JP] | Japan | 5-237440 |
| Nov. 26, 1993 | [JP] | Japan | 5-321029 |

[51] Int. Cl.⁶ ............................................. A61M 5/315
[52] U.S. Cl. ............................................. 604/228; 604/110
[58] Field of Search ............................................. 604/110, 195, 604/197, 198, 218, 220, 228, 240–243

[56] References Cited

U.S. PATENT DOCUMENTS

| 4,675,005 | 6/1987 | DeLuccia . |
| 4,692,156 | 9/1987 | Haller . |
| 4,710,170 | 12/1987 | Haber et al. . |
| 4,747,829 | 5/1988 | Jacob et al. . |
| 4,747,830 | 5/1988 | Gloyer et al. . |
| 4,941,883 | 7/1990 | Venturini . |
| 4,950,241 | 8/1990 | Ranford . |
| 4,950,251 | 8/1990 | Haining . |
| 4,986,813 | 1/1991 | Blake, III et al. ............ 604/110 |
| 5,026,354 | 6/1991 | Kocses . |
| 5,098,402 | 3/1992 | Davis . |
| 5,205,824 | 4/1993 | Mazur . |
| 5,215,529 | 6/1993 | Fields et al. . |
| 5,295,969 | 3/1994 | Fischell et al. . |
| 5,308,329 | 5/1994 | Mazur et al. . |
| 5,338,304 | 8/1994 | Adams ................... 604/110 |
| 5,403,288 | 4/1995 | Stanners ................. 604/232 |

FOREIGN PATENT DOCUMENTS

| 4091085 | 10/1985 | Australia . |
| 1418988 | 10/1988 | Australia . |
| 2879589 | 8/1989 | Australia . |
| 278493 | 8/1988 | European Pat. Off. . |
| 282097 | 9/1988 | European Pat. Off. . |
| 347742 | 12/1989 | European Pat. Off. . |
| 364387 | 4/1990 | European Pat. Off. . |
| 9215295 | 2/1993 | Germany . |
| S56149633 | 4/1983 | Japan . |
| S5724143 | 8/1983 | Japan . |
| S5932266 | 9/1986 | Japan . |
| S61-178348 | 11/1986 | Japan . |
| S63-2357 | 1/1988 | Japan . |
| S63-107382 | 4/1988 | Japan . |
| S63-503456 | 4/1988 | Japan . |

(List continued on next page.)

*Primary Examiner*—Ronald Stright, Jr.
*Assistant Examiner*—A. T. Nguyen
*Attorney, Agent, or Firm*—Eckert Seamans Cherin & Mellott, LLC

[57] ABSTRACT

A syringe assembly has a hub body which can be inserted into a hub insertion hole and pulled out thereof into inside a sringe body. A chamfer portion is formed at the hub body, being capable of engaging with the hub insertion hole. A needle insertion hole capable of being inserted a needle therein is provided with an end face of the hub body in a direction of an axis center of the hub body. A flow hole is provided with the hub body such that the needle insertion hole and an inside of the syringe body are communicated with each other in the direction of the axis center. A piston engagement hole is provided on end face side of the hub body, so as to engage with the piston. A seal taper is annularly formed at the hub body, such that its outside diameter is made narrower for the end face side, so as to abut on and contact with an inner face of the hub insertion hole.

13 Claims, 28 Drawing Sheets

FOREIGN PATENT DOCUMENTS

| | | |
|---|---|---|
| S63-144125 | 6/1988 | Japan . |
| S63-50608 | 7/1988 | Japan . |
| S63-219534 | 9/1988 | Japan . |
| S63-317634 | 12/1988 | Japan . |
| H1-7522 | 1/1989 | Japan . |
| H1-25601 | 2/1989 | Japan . |
| H1-94284 | 4/1989 | Japan . |
| H1-165147 | 6/1989 | Japan . |
| H1-201506 | 8/1989 | Japan . |
| H1-508739 | 8/1989 | Japan . |
| H2-500795 | 12/1989 | Japan . |
| H2-62155 | 6/1990 | Japan . |
| H2-509324 | 7/1990 | Japan . |
| H2-238860 | 9/1990 | Japan . |
| H2-256678 | 9/1990 | Japan . |
| H2-401754 | 12/1990 | Japan . |
| H3-41240 | 2/1991 | Japan . |
| 8900432 | 1/1989 | WIPO . |
| 8900435 | 1/1989 | WIPO . |
| 8909075 | 3/1989 | WIPO . |
| 8904681 | 6/1989 | WIPO . |
| 8909075 | 10/1989 | WIPO . |
| 9104065 | 4/1991 | WIPO . |
| 9107198 | 5/1991 | WIPO . |
| 9211883 | 12/1991 | WIPO . |
| 9209320 | 6/1992 | WIPO . |
| 9211883 | 7/1992 | WIPO . |

HUB FOR SYRINGE, CONNECTING STRUCTURE OF HUB, SYRINGE, PISTON, NEEDLE ASSEMBLY UNIT, CONNECTING STRUCTURE BETWEEN NEEDLE ASSEMBLY UNIT AND SYRINGE, SYRINGE ASSEMBLY AND METHOD OF ASSEMBLING SYRINGE ASSEMBLY

This is a division, of application Ser. No. 08/263,752 filed Jun. 22, 1994 now abandoned.

BACKGROUND OF THE INVENTION

This invention relates to a hub for a syringe, connecting structure of the hub, the syringe, a piston, a needle assembly unit, connecting structure between the needle assembly unit and the syringe, a syringe assembly and a method of assembling the syringe assembly, suitable for applying to a throwaway syringe assembly.

Since patient's blood included pathogenic bacteria adheres to a needle of a syringe assembly used, many throwaway syringe assemblies have been used for preventing secondary infection.

A conventional throwaway syringe assembly is disposed so as to discard after use. However, since it is necessary to remove a danger of secondary infection generating through the wound of a hand or the like by a needle attached a patient's blood and the like thereto when the syringe assembly is dealt with, the needle is cut from the syringe assembly with scissors or the like after use, and after that, they are discarded.

However, the handling operation of a conventional throwaway syringe assembly requires a long time since it is necessary to handle it with religious care so as not to hurt a hand or the like with the needle just after its use till the needle is cut.

In addition, the cutting operation of a conventional throwaway syringe assembly to be executed before disposal is troublesome.

Then, the throwaway syringe assembly, capable of maintaining safety just after use by inserting a needle into a syringe of the syringe assembly just after use using a screw or the like, and omitting cutting operation of a needle, has been proposed. However, the assembly and the operation of the proposed syringe assembly are difficult since its structure is complex.

It is preferable to use a syringe assembly more widely in such a manner that according to use, a plurality of kinds of needles are selected for a syringe or a plurality of kinds of syringes are selected for a needle so as to connect just before injection action at a site of treatment. However, it is difficult to easily insert a needle and a hub for connecting a needle with a syringe into a syringe at a site of treatment in a conventional throwaway syringe assembly proposed.

An object of the present invention is to provide a hub for a syringe, connecting structure of the hub, the syringe, a piston, a needle assembly unit, a connecting structure between the needle assembly unit and the syringe, a syringe assembly and a method of assembling the syringe assembly, in a throwaway syringe assembly, with which safety of the operations can be maintained just after use till its disposal and its disposal operation does not require a long time, its assembly and operation is easy, and which can be used for various purposes, taking the above-mentioned circumstances into consideration.

SUMMARY OF THE INVENTION

Of the present invention, the 1st invention comprises a hub for a syringe assembly, said syringe assembly having a syringe body, such as the syringe body 2, slidably attached a piston, such as the piston 39, thereto, said syringe body having a hub insertion hole, such as the hub insertion hole 4b, cylindrically formed at a top thereof, said hub to be attachably and detachably attached to said hub insertion hole, said hub comprising:

a cylindrical hub body, such as the hub body 15, through which said hub can be inserted into said hub insertion hole and can be pulled out of said hub insertion hole in said syringe body;

a held portion, such as the chamfer portion 16b, the held groove 61, or the held rib 63, provided with said hub body so as to engage with said hub insertion hole;

a needle insertion hole, such as the needle insertion hole 21, capable of inserting a needle, such as the needle 36, therein provided at one end, such as the end face 20a, of said hub body in a direction of an axis center, such as in the direction of the axis center P1, of said hub body;

a flow hole, such as the flow hole 27, provided with said hub body such that said needle insertion hole and an inside of said syringe body can be communicated with each other in said direction of said axis center;

a hub side engagement means, such as the piston engagement hole 29, provided at the other end, such as the end face 16a, of said hub body so as to engage with said piston; and a seal taper, such as the seal taper 17 (the form of the seal taper may be a plurality of fine rough portions annularly formed with the axis center P1 as its center, as well as a smooth face as shown in FIG. 5.), annularly provided with said hub body so as to abut on and contact with an inside face of said hub insertion hole such that its outside diameter is made narrower for said one end side of said hub body.

With this invention, the hub and the hub insertion hole are contacted with each other through the seal taper and the held portion, and it is easy to attach and detach the hub to and from the hub insertion hole. In addition, a predetermined seal efficiency and a predetermined holding efficiency can be exercised between the hub and the hub insertion hole. The operation of disposing the hub in case of assembly and the operation of pulling the needle into the syringe assembly after use can be smoothly and easily executed.

Of the present invention the 2nd invention comprises a structure of connecting a hub in which a hub for a syringe assembly is attachably and detachably connected with a syringe, such as the syringe 100, having a syringe body, such as the syringe body 2, formed a hub insertion hole, such as the hub insertion hole 4b, at a top thereof, said structure of connecting said hub comprising:

said hub body of said hub as set forth in claim 1 attachably and detachably inserted in said hub insertion hole so as to be inserted into said hub insertion hole and be pulled out of said hub insertion hole in said syringe body;

an insertion taper, such as the insertion taper 9, annularly provided with said hub insertion hole such that its inside diameter is made narrower for said top side of said syringe body, and said seal taper of said hub body being contacted with said insertion taper with seal contact with a predetermined seal pressure, such as the seal pressure F1,; and a holding portion, such as the rib for holding 11, or the holding groove 62, provided with an inner peripheral face of said hub insertion hole, being capable of engage with said held portion of said hub body, so as to hold and release said hub body with a predetermined holding force, such as the holding force F2.

With this invention, in addition to the effects of the 1st invention, the hub and the inner peripheral face of the hub insertion hole are contacted with each other through the seal taper and the insertion taper, and the held portion and the holding portion. Then, it is easy to attach and detach the hub to and from the hub insertion hole, and it is easy and effective to assemble the syringe assembly. Besides, since the direction in which the hub is pulled is one in which the seal taper is separated from the insertion taper when the needle used is pulled into the syringe assembly, the hub can be pulled inside the syringe assembly with a small pulling force making use of seal pressure. And, it is possible to smoothly easily execute the operation of discarding the syringe assembly used.

Of the present invention the 3rd invention comprises a syringe assembly, comprising:

a syringe and a hub having the connecting structure of the 2nd invention;

a piston, such as the piston 39, provided with said syringe body, occupying an inside of said syringe body in a direction of an axis so as to be movable in said direction of said axis with respect to said syringe body;

a piston side engagement means, such as the hub engagement portion 46, capable of engaging with said hub side engagement means of said hub provided with said piston, facing said hub side engagement means; and a needle, such as the needle 36, provided in said needle insertion hole of said hub.

With this invention, in addition to the effects of the 2nd invention, it is possible to engage the hub with the piston side engagement means of the piston after use so as to pull them inside of the syringe together with the needle. The needle used can be easily pulled into the syringe by only the operation of pressing and pulling the piston, the same as the operation of an usual sryinge assembly. Then, its operation is easy for everyone and there is no danger of error operation, and high safety is secured.

Of the present invention, the 4th invention comprises the syringe assembly of the 3rd invention, wherein said piston is comprised such that a piston body, such as the piston body 40, can be bent and taken between an operation portion, such as the outer press plate 42, and a liquid medicine press portion, such as the inner press plate 43.

With this invention, in addition to the effects of the 3rd invention, the piston is bent and taken, thereby the needle can remain inside the syringe being held with the top end portion of the piston. Then it is not operable from the outside. High safety is secured in case of disposal operation after that.

Of the present invention, the 5th invention comprises the syringe assembly of the 4th invention, wherein a piston stopper, such as the engagement rib 3, is provided with said syringe body so as not to pull said liquid medicine press portion of said piston out of said syringe body.

With this invention, in addition to the effects of the 4th invention, it is possible to prevent an operator from hurting with the needle used by inadvertently pulling the piston out of the syringe body when the piston is moved together with the needle. Therefore, high safety is secured.

Of the present invention, the 6th and the 7th inventions comprise the syringe assembly of the 4th or the 5th invention, wherein a notch for bending and taking, such as the notch 41, is formed at said piston body of said piston.

With both inventions, in addition of the effects of the respective inventions, the operation of bending and taking of the piston can be easily executed by making use of the notches.

Of the present invention, the 8th invention comprises the syringe assembly of the 7th invention, wherein said notch is formed so as to position at an end portion, such as the opening end 3$a$, of said syringe body when said piston abuts on said piston stopper.

With this invention, in addition to the effects of the respective inventions, the piston is pulled till it abuts on the piston stopper, and after that, the piston can be immediately bent and taken by making use of its end portion, and the operation of storing and remaining the needle in the syringe can be successively executed. Therefore, the operations of injection and disposal can be effectively executed.

Of the present invention, the 9th invention comprises a method of assembling the syringe assembly of the 3rd invention, said method comprising:

inserting said hub into said hub insertion hole from a side where said piston is inserted into said syringe body, such as the arrow B side;

disposing said hub in such a manner that said seal taper of said hub and said insertion taper of said hub insertion hole are contacted with each other with seal contact and said held portion of said hub and said holding portion of said hub insertion hole are engaged with each other; and inserting said piston into said syringe.

With this invention, assembly inserting the hub from the piston insertion side can be executed.

Of the present invention, the 10th invention comprises a syringe assembly, comprising:

a cylindrical syringe, such as the syringe X100, formed a liquid holding space, such as the medium holding space 153, therein, such as the inside space 102$a_i$;

a hub, such as the hub 109, attachably and detachably inserted into said syringe;

a needle, such as the needle 121, provided at a side back facing said liquid holding space of said hub so as to join;

a hub side engagement means, such as the piston engagement hole 115, provided with said hub such that an opening, such as the opening 117$b$, is formed at an end portion of said hub, such as the end portion 110$b$, facing said liquid holding space of said syringe, such that a communicating space, such as the piston engagement hole 115 and the flow hole 113, communicating with a liquid flow hole, such as the medium flow hole 121$a$, of said needle is formed;

a piston, such as the piston 123, occupying an inside of said syringe in a direction of an axis provided with said syringe, being movable in said direction of said axis, such as the directions as shown by the arrows XA and XB, with respect to said syringe;

a piston side engagement means, such as the hub engagement portion 131, provided with said piston, facing said hub side engagement means of said hub, so as to be inserted into and engaged with said hub side engagement means; and a first bypass means, such as the groove 132 and the bypass hole 139, communicating said communicating space and said liquid holding space with each other when said piston side engagement means is abutted on said hub, provided with said piston side engagement means.

With this invention, when the hub side engagement means and the piston side engagement means are engaged with each other at the time of the operation of storing the needle of the syringe assembly used, the liquid medicine remaining in the liquid holding space and the like are oppressed between the hub and the piston. However, the liquid medicine in which pressure rises by the oppression adequately escapes on the liquid flow hole side of the needle through the first bypass means by differential pressure, and then pressure rise of the liquid medicine remaining in the liquid holding space is extremely low restricted, and a resistance by the liquid medicine in which pressure rises does not almost acts on the piston. Then, the operation of the piston is easy without a big force.

Of the present invention, the 11th invention comprises the syringe assembly of the 10th invention, wherein said first bypass means is a groove formed along a surface of said piston side engagement means.

With this invention, in addition to the effects of the 10th invention, forming the first bypass means at the piston side engagement means becomes to be easy.

Of the present invention, the 12th invention comprises the syringe assembly of the 10th invention, wherein said first bypass means is a hole formed at said piston side engagement means.

With this invention, in addition to the effects of the 10th invention, there is no contact between the first bypass means and the hub when the piston side engagement means and the hub are abutted on each other. Then, the operation of the piston is certainly and easily executed since the first bypass means is not closed. Of the present invention, the 13th invention comprises a syringe assembly, comprising:

- a cylindrical syringe, such as the syringe X100, formed a liquid holding spacer such as the medium holding space 153, therein, such as the inside space 102a;
- a hub, such as the hub 109, attachably and detachably inserted into said syringe;
- a needle, such as the needle 121, provided on a side back facing said liquid holding space of said hub so as to join;
- a hub side engagement means, such as the piston engagement hole 115, provided with said hub such that an opening, such as the opening 117b, is formed at an end portion of said hub, such as the end portion 110b, facing said liquid holding space of said syringe, such that a communicating space, such as the piston engagement hole 115 and the flow hole 113, communicating with a liquid flow hole, such as the medium flow hole 121a, of said needle is formed;
- a second bypass means, such as the hub bypass groove 140 and the hub bypass hole 141, communicating said liquid holding space and said communicating space with each other, provided with said hub;
- a piston, such as the piston 123, occupying an inside of said syringe in a direction of an axis, such as the directions as shown by the arrows XA and XB, provided with said syringe, being movable in said direction of said axis with respect to said syringe; and
- a piston side engagement means, such as the hub engagement portion 131, provided with said piston, facing said hub side engagement means of said hub, so as to be inserted into and engaged with said hub side engagement means.

With this invention, when the hub side engagement means and the piston side engagement means are engaged with each other at the time of the operation of storing the needle of the syringe assembly used, the liquid medicine remaining in the liquid holding space and the like are oppressed between the hub and the piston. However, the liquid medicine in which pressure rises by the oppression adequately escapes on the liquid flow hole side of the needle through the second bypass means by differential pressure, and then pressure rise of the liquid medicine remaining in the liquid holding space is extremely low restricted, and a resistance by the liquid medicine in which pressure rises does not almost act on the piston. Then, the operation of the piston is easy without a big force.

Of the present invention, the 14th invention comprises the syringe assembly of the 13th invention, wherein said second bypass means is a groove formed along a surface of said hub side engagement means.

With this invent on, in addition to the effects of the 13th invention, forming the second bypass means at the hub becomes to be easy.

Of the present invention, the 15th invention comprises the syringe assembly of the 13th invention, wherein said second bypass means is a hole formed at said hub.

With this invention, in addition to the effects of the 13th invention, there is no contact between the second bypass means and the piston side eagagement means when the piston side engagement means and the hub are abutted on each other. Then, the operation of the piston is certainly and easily executed since the second bypass means is not closed.

Of the present invention, the 16th invention comprises the piston to be used for the syringe assembly of the 10th invention, comprising:

- said piston having a piston body, such as the piston body 125,;
- a press portion, such as the inner press plate 129, the packing support 130, and the packing 133, provided with a top end side of said piston body, capable of occupying an inside of said syringe in a direction of an axis, being slidable and movable inside said syringe in said direction of said axis;
- a piston side engagement means provided with said top end side of said press portion, capable of being inserted into and engaged with said hub side engagement means; and
- a first bypass means, such as the groove 132, the bypass hole 139, communicating said communicating space and said liquid holding space with each other when said piston side engagement means is abutted on said hub, provided with said piston side engagement means.

With this invention, in addition to the effects of the 10th invention, since the first bypass means is formed on the piston side, various kinds of hubs can be used according to a situation.

Of the present invention, the 17th invention comprises the piston of the 16th invention, wherein said first bypass means is a groove formed along a surface of said piston side engagement means.

In addition to the effects of the 16th invention, this invention has the effects similar to ones of the 11th invention.

Of the present invention, the 18th invention comprises the piston of the 16th invention, wherein said first bypass means is a hole formed at said piston side engagement means.

In addition to the effects of the 16th invention, this invention has the effects similar to ones of the 12th invention.

Of the present invention, the 19th invention comprises a hub, such as the hub 109, for a syringe assembly, to be inserted into a syringe, such as the syringe X100, comprising:

- said hub having a hub body, such as the hub body 190, capable of attachably and detachably inserted into said syringe;

a needle insertion portion, such as the needle insertion hole 112, capable of inserting a needle, such as the needle 121, therein provided with one end, such as the end portion 111a, of said hub body in a direction of an axis center of said hub body, such as the directions as shown by the arrows XA and XB;

a hub side engagement means, such as the piston engagement hole 115, provided with said hub body such that an opening, such as the opening 117b, is formed at the other end, such as the end portion 110b, of said hub body, such that a communicating space, such as the piston engagement hole 115 and the flow hole 113, communicating with said needle insertion portion is formed; and a second bypass means, such as the hub bypass groove 140 and the hub bypass hole 141, communicating a liquid holding space, such as the medium holding space 153, inside said syringe and said communicating space with each other when said hub body is inserted into said syringe, formed at said hub body.

This invention has the effects similar to ones of the 13th invention. Of the present invention, the 20th invention comprises the hub of the 19th invention, wherein said second bypass means is a groove formed along a surface of said hub side engagement means.

This invention has the effects similar to ones of the 14th invention.

Of the present invention, the 21st invention comprises the hub of the 19th invention, wherein said second bypass means is a hole formed at said hub body.

This invention has the effects similar to ones of the 15th invention.

Of the present invention, the 22nd invention comprises a syringe assembly, comprising:

a cylindrical portion, such as the main cylindrical portion 203;

a cylindrical hub insertion portion, such as the hub insertion portion 204, having an inside diameter smaller than one of said cylindrical portion provided with a top end side of said cylindrical portion such that a communicating portion, such as the taper 206, is formed between said cylindrical portion and said hub insertion portion;

a hub, such as the hub 209, attachably and detachably inserted into said hub insertion portion;

a needle, such as the needle 221, provided on a side back facing said cylindrical portion of said hub so as to join;

a hub side engagement means, such as the piston enagement hole 215, provided on a side of said hub facing said cylindrical portion;

a piston body, such as the piston body 225, provided with said cylindrical portion in such a manner that said piston body is inserted into inside of said cylindrical portion;

a piston side engagement means, such as the hub engagement portion 231, provided with said piston body, facing said hub side engagement means of said hub, capable of inserted into and engaged with said hub side engagement means;

an occupying means, such as the packing 233, made of elastic material, provided with said piston body, occupying inside of said cylindrical portion in a direction of an axis, such as the directions as shown by the arrows YA and YB, being slidable and movable together with said piston body in said direction of said axis with respect to said cylindrical portion;

an engagement portion, such as the end portion 235d and the engagement projection 255, capable of abutting on said communicating portion by movement of said occupying means in said direction of said axis, provided with said occupying means; and a pressing portion, such as the surface 235e, provided with said occupying means such that a gap space, such as the remaining space 251, can be formed between said pressing portion and said communicating portion when said engagement portion and said communicating portion are abutted on each other.

With this invention, when the piston body is pressed on the hub side from the injection end position so as to further feed the piston side engagement means to the hub side in the operation of storing the needle, the occupying means receives a reaction from the communicating portion abutting in the portion near the engagement portion so as to be compressed in the direction of the axis. Besides, the pressing portion is pulled out on the hub side, narrowing the gap space, that is, approaching the communicating portion. That is, the quantity of oppression of the occupying means is reduced by the quantity which the pressing portion is pulled out on the hub side in the gap space, and then the feeding of the piston side engagement means can be executed with extremely small force. Therefore, the operation of storing the needle is easily executed.

Of the present invention, the 23rd invention comprises the piston, such as the piston 223, to be used for the syringe assembly of the 22nd invention, comprising:

said piston having a piston body, such as the piston body 225;

a piston side engagement means, such as the hub engagement portion 231, provided with a top end side of said piston body so as to be inserted into and engaged with said hub side engagement means;

an occupying means, such as the packing 233, made of elastic material, provided with said piston body, capable of occupying inside of said cylindrical portion, such as the main cylindrical portion 203, in a direction of an axis, such as the directions as shown by the arrows YA and YB, being slidable and movable together with said piston body in said direction of said axis with respect to said cylindrical portion;

an engagement portion, such as the end portion 235d and the engagement projection 255, capable of abutting on said communicating portion, such as the taper 206, by movement of said occupying means in said direction of said axis with respect to said cylindrical portion, provided with said occupying means; and a pressing portion, such as the surface 235e, provided with said occupying means such that a gap space, such as the remaining space 251, can be formed between said pressing portion and said communicating portion when said engagement portion and said communicating portion are abutted on each other.

This invention has the effects similar to ones of the 22nd invention by applying the piston to the syringe assembly of the 22nd invention.

Of the present invention, the 24th invention comprises a syringe assembly comprising:

a cylindrial syringe, such as the syringe Y100, formed a liquid holding space, such as the medium holding space 253, therein;

a hub, such as the hub 209, attachably and detachably inserted into said syringe;

a needle, such as the needle 221, provided on a side back facing said liquid holding space of said hub so as to join;

a hub side engagement means, such as the piston engagement hole 215, provided on a side facing said liquid holding space of said hub;

a piston body, such as the piston body 225, provided with said syringe in such a manner that said piston body is inserted inside of said syringe;

a piston side engagement means, such as the hub engagement portion 231, provided with said piston body, facing said hub side engagement means of said hub, so as to be inserted into and engaged with said hub side engagement means;

an occupying member, such as the packing 233, made of elastic material occupying inside said syringe in a direction of an axis, such as the directions as shown by the arrows YA and YB, being movable together with said piston body in said direction of said axis with respect to said syringe, provided with said piston body, and deformation accelerating space, such as the clearance space 235f, formed inside of said occupying member.

With this invention, when the occupying member is elastically oppressed in the operation of storing the needle so as to engage the piston and the hub are engaged with each other, the deformation accelerating space inside the occupying member can be oppressed with a smaller force in comparison with the oppression of elastic material, and the quantity of elastic oppresion in the occupying member is reduced by the quantity of the deformation accelerating space. Therefore, the piston and the hub can be engaged with each other with an extremely small force, and then, the operation of storing the needle can be easily executed. Of the present invention, the 25th invention comprises the syringe assembly of the 24th invention, wherein said deformation accelerating space is hollow.

With this invention, in addition to the effects of the 24th invention, since the deformation accelerating space can be oppressed extremely easily, the engagement between the piston and the hub further becomes to be easy. Of the present invention, the 26th invention comprises the syringe assembly of the 24th invention, wherein said deformation accelerating space is filled with soft material being softer than said occupying member.

With this invention, in addition to the effects of the 24th invention, since entering injection medium or air into the deformation accelerating space is saved, the holding quantity of the injection medium in the liquid holding space in the syringe or the quantity of air remaining in the liquid holding space is correctly grasped and credibility is increased.

Of the present invention, the 27th invention comprises the piston, such as the piston 223, to be used for the syringe assembly of the 24th invention:

said piston having a piston body, such as the piston body 225;

a piston side engagement means, such as the hub engagement portion 231, provided with a top end side of said piston body so as to be inserted into and engaged with said hub side engagement means;

an occupying member, such as the packing 233, made of elastic material, provided with said piston body, capable of occupying inside of said syringe in a direction of an axis, such as the directions as shown by the arrows YA and YB, being movable together with said piston body in said direction of said axis with respect to said syringe; and a deformation accelerating space, such as the clearance space 235f, formed inside said occupying member.

This invention has the effects similar to ones of the 24th invention by applying the piston of the 27th invention to the syringe assembly.

Of the present invention, the 28th invention comprises the piston of the 27th invention, wherein said deformation accelerating space is hollow.

This invention has the effects similar to ones of the 25th invention by applying the piston of the 28th invention to the syringe assembly.

Of the present invention, the 29th invention comprises the piston of the 27th invention, said deformation accelerating space is filled with soft material being softer than said occupying member.

This invention has the effects similar to ones of the 26th invention by applying the piston of the 29th invention to the syringe assembly.

Of the present invention, the 30th invention comprises an occupying member for a syringe assembly comprising:

a main body, such as the packing body 235, made of elastic material;

a sliding face for syringe, such as the sliding face 235g, formed at a periphery of said main body;

a liquid pressing face, such as the surface 235e, formed at one end of said main body;

a supporting face, such as the supporting face 235h, formed at the other end of said main body;

a piston engagement insertion space, such as the engagement hole 235a, provided with said main body; and a deformation accelerating space, such as the clearance space 235f, formed between said piston engagement insertion space and said sliding face for syringe.

This invention has the effects similar to ones of the 27th invention by applying the occupying member of the 30th invention to the piston.

Of the present invention, the 31st invention comprises the occupying member of the 30th invention, wherein said deformation accelerating space is hollow.

This invention has the effects similar to ones of the 28th invention by applying the occupying member of the 31st invention to the piston.

Of the present invention, the 32nd invention comprises the occupying member of the 30th invention, said deformation accelerating space is filled with soft material being softer than said main body.

This invention has the effects similar to ones of the 29th invention by applying the occupying member of the 32nd invention to the piston.

Of the present invention, the 33rd invention comprises a needle assembly unit comprising:

a hub body, such as the hub body 310, cylindrically formed;

an abutting end portion, such as the end face 310a, formed on one end side of said hub body;

an engagement holding portion, such as the engagement holding pillar portion 311, provided with said abutting end portion side of said hub body, having an outside diameter, such as the outside diamter ZL2, smaller than one, such as the outside diameter ZL1 or ZL1', of said hub body;

a needle, such as the needle 321, connected with said engagement holding portion;

an engagement means for piston, such as the piston engagement hole 315, provided on an opposite side of said one end side of said hub body;

an engagement means for syringe, such as the hub stop groove 310c, annularly formed on an outer peripheral face side, such as the outer peripheral face 310f, of said hub body;

a reaction fixed member, such as the hub fixed member 361, formed a hub engagement hole, such as the hub engagement hole 362, provided with said engagement holding portion so as to engage such that said engagement holding portion is inserted into said hub engagement hole so as to be inserted into and pulled out of; and a fixed means for syringe, such as the syringe engagement projection 363, formed at said reaction fixed member.

When the needle assembly unit according to this invention is connected with the syringe for the syringe assembly, the reaction fixed member of the needle assembly unit is fixed by and engaged with the syringe through the syringe fixed member, and therefore, the abutting end portion side of the hub body can be indirectly supported by the syringe through the reaction fixed means. Then, no means for directly supporting the hub body so as not to slip the hub body out of the top end side thereof to the outside may be provided on the syringe for connecting with the needle assembly unit. And, the syringe having no means for directly supporting the hub body is used, thereby the hub body can be easily inserted from the top end side of the syringe since no resistance is received at the time of insertion. Accordingly, when the needle assembly unit according to this invention is used, the hub body connected the needle can be easily connected with the syringe at the site of treatment. Then, a plurality of kinds of needle assembly units and a plurality of kinds of syringes which are respectively not yet connected with each other are prepared at the site of treatment, and then, according to use, such as treatment, appropriate needle assembly unit and the syringe to be used are selected from a plurality of kinds of the needle assembly units and a plurality of kinds of the syringes so as to connect both with each other just before injection action. As a result, the syringe assembly can be used for various purposes.

Of the present invention, the 34th invention comprises a syringe comprising:

a syringe body, such as the syringe body 302, in the shape of a cylinder;

a hub insertion portion, such as the hub insertion portion 307, cylindrically formed on a top end side of said syringe body through a hub introducing opening, such as the opening end 307g;

an engagement means for reaction fixed member, such as the hub fixed member engagement groove 307c, formed on an outer peripheral face side, such as the outer peripheral face 307f, of said hub insertion portion; and an engagement means for hub, such as the hub stop rib 307d, annularly formed on an inner peripheral face side, such as the inner peripheral face 307a, of said hub insertion portion.

The reaction fixed member is engaged with and fixed by the syringe according to this invention through the reaction fixed member engagement means. When the hub body for the syringe assembly is inserted into the syringe, the hub body can be indirectly supported by the syringe side through the reaction fixed member so as not to slip the hub body out of the top end side of the syringe to outside. Then, no means for directly supporting the hub body so as not to slip the hub body out of the top end side of the syringe to the outside may be provided on the syringe. That is, the hub body can be easily inserted from the top end side of the syringe since no resistance is received at the time of insertion. Accordingly, when the syringe according to this invention is used, the hub body connected the needle can be easily connected with the syringe at the site of treatment. Then, a plurality of kinds of needles connected with the hub body, engaging with the reaction fixed member and the syringe are prepared in such a state that both are not yet connected with each other at the site of treatment, and then, according to use, such as treatment, a needle is selected from a plurality of kinds of needles for a syringe (or, a syringe is selected from a plurality of kinds of syringes for a needle) so as to connect with each other just before the injection action. As a result, the syringe assembly can be used for various purposes.

Of the present invention, the 35th invention comprises a connecting structure between the needle assembly unit of the 33rd invention and the syringe of the 34th invention, comprising:

said hub body inserted inside of said hub insertion portion such that said abutting end portion side of said hub body is back faced to said syringe body, such that said engagement means for syringe of said hub body and said engagement means for hub of said hub insertion portion are free to be engaged with and disengaged from each other; and said reaction fixed member installed on an outer pripheral face side of said hub insertion portion such that said engagement means for reaction fixed member of said hub insertion portion and said fixed means for syringe of said reaction fixed member are engaged with each other.

The needle assembly unit of the 33rd invention and the syringe of the 34th invention can be easily connected with each other at the site of treatment, forming the connecting structure according to this invention. Then, a plurality of kinds of needles connected with the hub body, engaging with the reaction fixed member and a plurality of kinds of syringes are prepared in such a state that both are not yet connected with each other at the site of treatment, and then, according to use, such as treatment, a needle is selected for a plurality of kinds of syringes or a plurality of kinds of needles are selected for a syringe just before the injection action so as to connect with each other. As a result, the syringe assembly can be used for various purposes.

DESCRIPTION OF THE PREFERRED EMBODIMENT

Embodiments of the present invention will now be described hereinafter with respect to the accompanying drawings.

Figure 1:
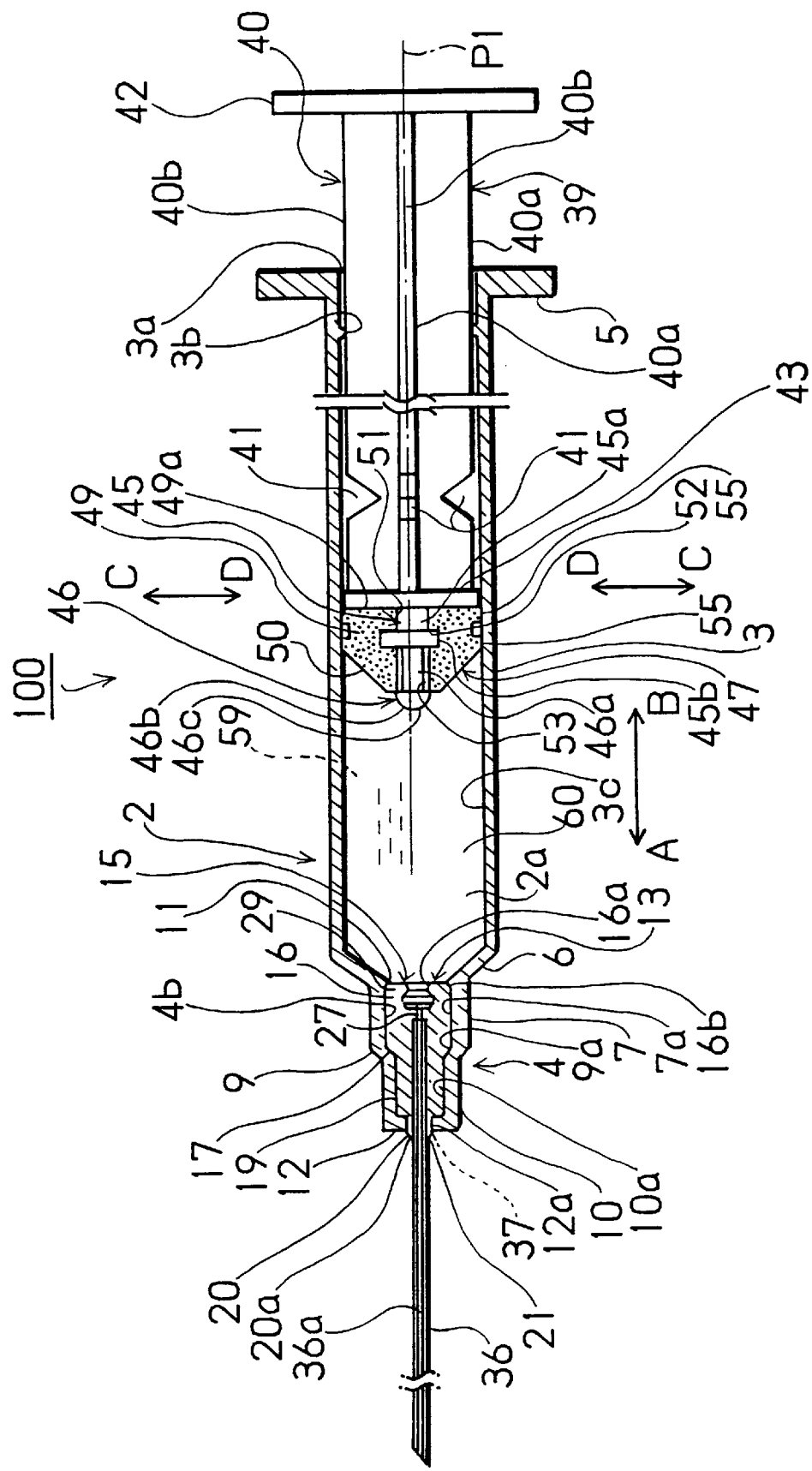
FIG. 1 is a typical sectional view showing an example of a syringe assembly according to the present invention.

A syringe assembly 1 according to the present invention has a syringe 100 made of resin, as shown in FIG. 1. A syringe body 2 is provided with the syringe 100 (FIG. 1 is a typical cross section of the syringe assembly 1, but a side is shown in a part of a piston 39, described hereinafter, not the section, for convenience.). A main cylindrical portion 3, cylindrically formed, is provided with the syringe body 2. A direction of an axis center of the main cylindrical portion 3, that is, the reciprocating directions parallel to an axis center P1 are an arrow A direction in the figure (or the left direction of the paper of FIG. 1.) and an arrow B direction (or the right direction of the paper of FIG. 1).

On the outer periphery side of the main cylindrical portion 3, a syringe support 5, being in the shape of a plate, is provided near an opening end 3a of the arrow B side of the main cylindrical portion 3 (the right side of the paper of FIG. 1), in such a manner as forming a flange of the main cylindrical portion 3. On an inner peripheral face 3c side of the main cylindrical portion 3, an engagement rib 3b, projecting in the direction for the axis center P1 of the main cylindrical portion 3, that is, the direction as shown by an arrow D of the figure, is annularly formed near the opening end 3a along the inner peripheral face 3c.

On the arrow A side of the main cylindrical portion 3 (the left side of the paper of FIG. 1) a taper 6 in the shape of a funnel is formed unitedly connecting with the main cylindrical portion 3. The inside diameter in the section perpendicular to the directions as shown by the arrows A and B of the taper 6 (that is, the circular section) is made narrower for the direction as shown by the arrow A.

The inside of the main cylindrical portion 3 and the inside of the taper 6 communicate with each other in the directions as shown by the arrows A and B, and the space which consists of both insides combined is an inside space 2a of the syringe body 2.

Figure 2:
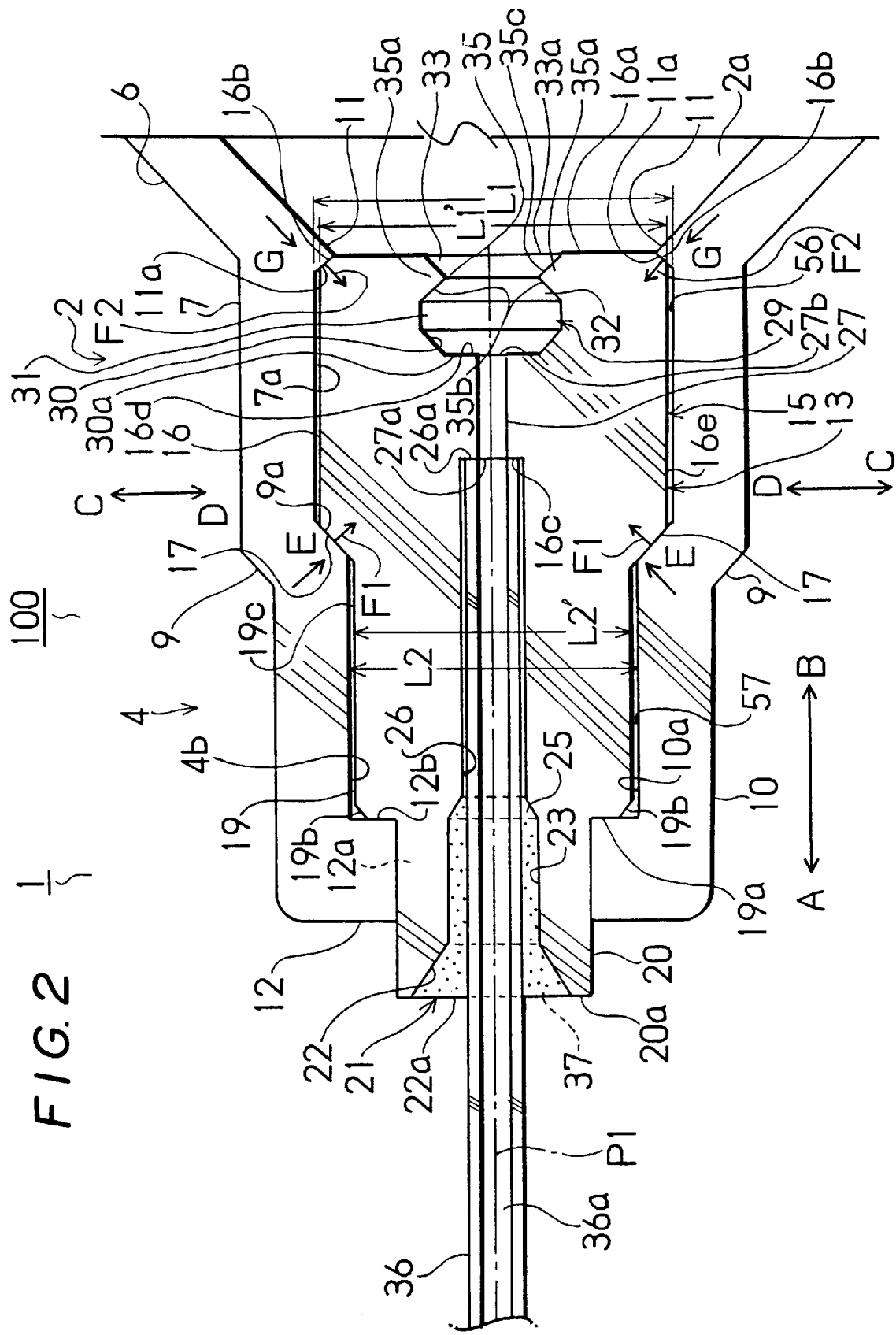
FIG. 2 is an enlarged sectional view in a portion near a hub of the syringe assembly as shown in FIG. 1.

On the side of the arrow A of the taper 6, that is, on the side of the top of the syringe body 2, as shown in FIGS. 1 and 2, a cylindrical hub insertion portion 4 is formed unitedly connecting with the taper 6, and the hub insertion portion 4 has a first small cylindrical portion 7. On this occasion, the first small cylindrical portion 7 is formed unitedly connecting with the taper 6, and the hub insertion portion 4 is formed unitedly connecting with the taper 6 in the first small cylindrical portion 7.

On the arrow A side of the first small cylindrical portion 7, an insertion taper 9 in the shape of a funnel is formed unitedly connecting with the first small cylindrical portion 7. The inside diameter in the section perpendicular to the directions as shown by the arrows A and B of the insertion taper 9 (that is, the circular section) is made narrower for the direction as shown by the arrow A.

On the arrow A side of the insertion taper 9, a second small cylindrical portion 10 in the shape of a cylinder is formed, and the second small cylindrical portion 10 is formed unitedly connected with the insertion taper 9.

The first small cylindrical portion 7, the insertion taper 9 and the second small cylindrical portion 10 are respectively formed coaxial with the main cylindrical portion 3. An inside diameter L1 of the first small cylindrical portion 7 is smaller than one of the main cylindrical portion 3, and an inside diameter L2 of the second small cylindrical portion 10 is smaller than the inside diameter L1 of the first small cylindrical portion 7 (However, the inside diameter L1 of the first small cylindrical portion 7 is one in portions excluding a rib for holding 11, as described hereinafter.).

On the side of an inner peripheral face 7a of the first small cylindrical portion 7, the side of an inner peripheral face 9a of the insertion taper 9, and the side of an inner peripheral face 10a of the second small cylindrical portion 10, a hub insertion hole 4b is formed communicating in the directions as shown by the arrows A and B. The rib for holding 11 is formed projecting for the axis center P1 near the end portion of the arrow B side of the hub insertion hole 4b, that is, near the boundary portion between the first small cylindrical portion 7 and the taper 6. The rib for holding 11 is formed along a circumference which center is the axis center P1, that is, annularly formed along the inner peripheral face 7a of the first small cylindrical portion 7.

An end wall 12, being in the shape of a circular plate, is formed on the arrow A side of the second small cylindrical portion 10 such that the outside diameter of the end wall 12 is equal to one of the second small cylindrical portion 10 and both front and back wall faces thereof are perpendicular to the directions as shown by the arrows A and B. The end wall 12 is provided matching with the second small cylindrical portion 10 and being united therewith. A circular hole 12a, which center is the axis center P1, is provided with the end wall 12 penetrating both front and back wall faces of the end wall 12 in the directions as shown by the arrows A and B.

As described before, the hub insertion portion 4 is comprised of the first small cylindrical portion 7, the insertion taper 9, the second small cylindrical portion 10 and the end wall 12. The syringe 100 is comprised such that the syringe body 2 and the syringe support 5 are unitedly formed. The syringe body 2 is comprised such that the main cylindrical portion 3, the taper 6 and the hub insertion portion 4 are unitedly formed.

On the other hand, as shown in FIG. 2, a hub 13 is inserted into the hub insertion hole 4b of the hub insertion portion 4, and the hub 13 has a hub body 15. The first pillar portion 16 in the shape of a cylinder, which longitudinal direction is parallel to the directions as shown by the arrows A and B and which axis center is the axis center P1, is provided with the hub body 15. On the arrow A side of the first pillar portion 16, a seal taper 17, which axis center is the axis center P1, is taperingly formed, unitedly connecting with the first pillar portion 16. The section perpendicular to the directions as shown by the arrows A and B of the seal taper 17 (that is, the circular section) is made narrower for the direction as shown by the arrow A. On the arrow A side of the seal taper 17, the second pillar portion 19 in the shape of a cylinder, which axis center is the axis center P1, is formed. The second pillar portion 19 is formed unitedly connecting with the seal taper 17.

An end face 16a is formed at the end portion of the arrow B side of the first pillar portion 16 (the right side of the paper of FIG. 2), perpendicular to the directions as shown by the arrows A and B. Chamfer portions 16b are taperingly formed at the corner portions of the peripheral side in the end face 16a. An end face 19a is formed at the end portion of the arrow A side of the second pillar portion 19 (the left side of the paper of FIG. 2), perpendicular to the directions as shown by the arrows A and B. Chamfer portions 19b are taperingly formed at the corner portions of the peripheral side in the end face 19a.

On the end face 19a side of the second pillar portion 19, a third pillar portion 20, projecting and extending in the direction as shown by the arrow B, is provided united with the second pillar portion 19, and coaxial therewith.

As described before, the hub body 15 is comprised of the first pillar portion 16, the seal taper 17, the second pillar portion 19, and the third pillar portion 20. The hub body 15 is inserted into the hub insertion hole 4b of the hub insertion portion 4 in such a manner that the first pillar portion 16 is inserted in the inner peripheral face 7a side of the first small cylindrical portion 7, the seal taper 17 is inserted in the inner peripheral face 9a side of the insertion taper 9, the second pillar portion 19 is inserted in the inner peripheral face 10a side of the second small cylindrical portion 10, and the third pillar portion 20 is inserted into the hole 12a of the end wall 12 penetrating the hole 12a.

The hub body 15 is inserted such that the seal taper 17 matches and closely contacts with the inner peripheral face 9a of the insertion taper 9, and the chamfer portion 16b of the first pillar portion 16 matches and closely contacts with a side face 11a of the arrow A side of the rib for holding 11 (that is, the left side of the paper of FIG. 2.).

On this occasion, the seal taper 17 receives a seal pressure F1 from the insertion taper 9 in a direction perpendicular to a contact face, that is, the direction perpendicular to the inner peripheral face 9a, and in the direction as shown by the arrow E in the figure for the axis center P1. The chamfer portion 16b receives a holding force F2 from the rib for holding 11 in a direction perpendicular to a contact face, that is, the direction perpendicular to the side face 11a of the rib for holding 11, and in the direction as shown by the arrow G in the figure, inclined to the axis center P1.

That is, in such a state that the hub 13 is inserted into the hub insertion hole 4b, the first small cylindrical portion 7 is elastically deformed slightly extending in the directions as shown by the arrows A and B, and by its restoring force, the seal pressure F1 and the holding force F2, above-mentioned, are supplied. The seal pressure F1 and the holding force F2 match with each other through the hub 13 such that the seal pressures F1 and F1, the holding forces F2 and F2, or the seal pressure F1 and the holding force F2 match with each other in the directions as shown by the arrows C and D, or in the directions as shown by the arrows A and B, thereby the hub 13 is fixed.

The outside diameter L1' of the first pillar portion 16 is smaller than the inside diameter L1 of the first small cylindrical portion 7 in the portion existing no rib for holding 11, and the outside diameter L2' of the second pillar portion 19 is smaller than the inside diameter L2 of the second small cylindrical portion 10. Therefore, a first gap space 56 is formed between an outer peripheral face 16e of the first pillar portion 16 and the inner peripheral face 7a of the first small cylindrical portion 7. A second gap space 57 is formed between an outer peripheral face 19c of the second pillar portion 19 and the inner peripheral face 10a of the second small cylindrical portion 10.

The outside diameter of the third pillar portion 20 is slightly smaller than (or the same as) the inside diameter of the hole 12a formed at the end wall 12. A wall face 12b of the arrow B side of the end wall 12 (that is, the right side of the paper of FIG. 2) and the end face 19a of the second pillar portion 19 almost contact with each other, but one of both do not operate pressing force to the other. The hub body 15 is inserted as described before.

A needle insertion hole 21 is provided with the hub 13, as shown in FIG. 2. The needle insertion hole 21 is comprised of a first taper hole 22, a first pillar hole 23, a second taper hole 25 and a second pillar hole 26.

The first taper hole 22 forms an opening 22a in the shape of a circular, which center is the axis center P1, at an end face 20a of the arrow A side of the third pillar portion 20 of the hub 13 (the left side of the paper of FIG. 2), and is formed for the direction as shown by the arrow B from the end face 20a. The diameter of the section perpendicular to the directions as shown by the arrows A and B of the first taper hole 22 (that is, the circular section, which center is the axis center P1) is made narrower for the direction as shown by the arrow B.

On the arrow B side of the first taper hole 22, the first pillar hole 23 in the shape of a cylinder, which center is the axis center P1, is provided connecting with the first taper hole 22. On the arrow B side of the first pillar hole 23, the second taper hole 25 is provided in the direction as shown by the arrow B, connecting with the first pillar hole 23. The diameter of the section perpendicular to the directions as shown by the arrows A and B of the second taper hole 25 (that is, the circular section which center is the axis center P1) is made narrower for the direction as shown by the arrow B.

On the arrow B side of the second taper hole 25, the second pillar hole 26 in the shape of a cylinder, which center is the axis center P1, is provided, connecting with the second taper hole 25. An end portion 26a of the arrow B side of the second pillar hole 26 reaches the inside of the first pillar portion 16. The end portion 26a of the second pillar hole 26 contacts with a wall face 16c perpendicular to the directions as shown by the arrows A and B.

On the other hand, a flow hole 27 is provided with the first pillar portion 16 of the hub 13, adjacent to the arrow B side of the second pillar hole 26 of the needle insertion hole 21 (the right side of the paper of FIG. 2). The flow hole 27, which center is the axis center P1, having the diameter smaller than one of the second pillar hole 26, is provided in the shape of a cylinder. The flow hole 27 communicates with the second pillar hole 26 of the needle insertion hole 21, forming a circular opening 27a at the wall face 16c of the first pillar portion 16.

A piston engagement hole 29 is provided with the first pillar portion 16 of the hub 13, adjacent to the arrow B side of the flow hole 27 (the right side of the paper of FIG. 2). The piston engagement hole 29 is comprised of the first taper hole 30, the pillar hole 31, the second taper hole 32 and the third taper hole 33.

The first taper hole 30 is provided in the first pillar portion 16, adjacent to the arrow B side of the flow hole 27 (the right side of the paper of FIG. 2). The section perpendicular to the directions as shown by the arrows A and B of the first taper hole 30 is a circular section, which center is the axis center P1. The diameter of the section of the first taper hole 30 is made wider for the direction as shown by the arrow B. The diameter of a circular end portion 30a of the arrow A side of the first taper hole 30 is bigger than one of the flow hole 27. Therefore, the end portion 30a contacts with a wall face 16d perpendicular to the directions as shown by the arrows A and B. At the wall face 16d, a circular opening 27b is formed by provision of the flow hole 27. The first taper hole 30 and the flow hole 27 communicate with each other through the opening 27b.

On the arrow B side of the first taper hole 30, the pillar hole 31 in the shape of a cylinder, which center is the axis center P1, is provided connecting with the first taper hole 30. On the arrow B side of the pillar hole 31, the second taper hole 32, which diameter of the section perpendicular to the directions as shown by the arrows A and B (that is, the circular section which center is the axis center P1) is made narrower for the direction as shown by the arrow B, is provided in the direction as shown by the arrow B, connecting with the pillar hole 31. On the arrow B side of the second taper hole 32, the third taper hole 33 is provided in the direction as shown by the arrow B, connecting with the second taper hole 32. The diameter of the section perpendicular to the directions as shown by the arrows A and B of the third taper hole 33 (that is, the circular section which center is an axis center P2) is made wider for the direction as shown by the arrow B. Therefore, the portion sandwitched between a wall face 35b facing the second taper hole 32 and a wall face 35c facing the third taper hole 33 forms a projection 35a, projecting for the axis center P1 with a boundary portion 35 between the second taper hole 32 and the third taper hole 33 of the first pillar portion 16 as an apex.

The arrow B side of the third taper hole 33 opens outside forming a circular opening 33a at the end face 16a of the first pillar portion 16.

on the other hand, a needle 36 is inserted into the needle insertion hole 21 of the hub 9, as shown in FIG. 1 or FIG. 2. The top of the needle 36 positions at the outside of the syringe body 2, and the needle 36 is inserted into the needle insertion hole 21 from the rear end side. The rear end of the needle 26 abuts on the wall face 16c formed on the arrow B side of the needle insertion hole 21. A medium flow hole 36a provided penetrating in the directions as shown by the arrows A and B from the top to the rear of the needle 36 and the flow hole 27 communicate with each other in the directions as shown by the arrows A and B through the right end portion of FIG. 2 of the flow hole 36a.

An adhesive 37 is filled with in a space between the needle 36 and the hub 13 of the needle insertion hole 21 and is hardened.

As shown in FIG. 1, the piston 39 is provided with the syringe assembly 1 (FIG. 1 is a typical cross section of the syringe assembly 1, but a side is shown in a piston body 40, an outer press plate 42 and an inner press plate 43, described hereinafter, of the piston 39, not the section, for convenience.).

The piston 39 has the bar-shaped piston body 40 extending in the directions as shown by the arrows A and B. The piston body 40 is comprised such that two congruent plate portions 40a, each which is a plate shaped rectangle especially long in the directions as shown by the arrows A and B, are unitedly cross provided with each other such that the sections thereof form the shape of a cross. The width perpendicular to the directions as shown by the arrows A and B of the plate face of the plate portion 40a is almost equal to the inside diameter at the engagement rib 3b of the main cylindrical portion , and the piston body 40 is inserted into the main cylindrical portion 3 through the opening end 3a from the arrow A side of the piston body 40.

On each plate portion 40a of the piston body 40, notches 41 are formed from both side portions 40b, 40b of respective plate portions 40a, 40a to the direction of the axis center (that is, the axis center P1) of the piston body 40 in the shape of a wedge near the direction by the arrow A. Four notches 41 are provided at the positions adjusted one another in the directions as shown by the arrows A and B.

The outer press plate 42, which plate face is a circular plate perpendicular to the directions as shown by the arrows A and B, is provided on the end portion side of the arrow B side of the piston body 40, being united with the piston body 40, and coaxial with the piston body 40. The diameter of the outer press plate 42 is fully bigger than the inside diameter of the main cylindrical portion 3.

As shown in FIG. 1, the inner press plate 43, which plate face is a circular plate perpendicular to the directions as shown by the arrows A and B, is provided on the end portion side of the arrow A side of the piston body 40, being united with the piston body 40 and coaxial with the piston body 40 (Therefore, the inner press plate 43 is positioned inside the main cylindrical portion 3.). The diameter of the inner press plate 43 is almost equal to the inside diameter of the main cylindrical portion 3 (Therefore, the diameter of the inner press plate 43 is bigger than the inside diameter at the engagement rib 3b of the main cylindrical portion 3.).

As shown in FIG. 1, a packing support 45 is provided with the inner press plate 43 on the arrow A side of it. A pillar portion 45a in the shape of a circular cylinder, which extends in the directions as shown by the arrows A and B, is provided with the packing support 45, coaxial with the inner press plate 43. The diameter of the pillar portion 45a is smaller than one of the inner press plate 43, and the pillar portion 45a is provided on the arrow A side of the inner press plate 43, being united with the inner press plate 43. A circular plate portion 45b, which plate face is a circular plate perpendicular to the directions as shown by the arrows A and B, is provided on the arrow A side of the pillar portion 45a, coaxial with the pillar portion 45a, united with the pillar portion 45a. The diameter of the circular plate portion 45b is bigger than one of the pillar portion 45a, and is smaller than one of the inner press plate 43.

A hub engagement portion 46 is provided on the arrow A side of the circular plate portion 45b, and a pillar portion 46a in the shape of a circular cylinder, which extends in the directions as shown by the arrows A and B, is provided with the hub engagement portion 46, coaxial with the circular plate portion 45b. The diameter of the pillar portion 46a is smaller than one of the circular plate portion 45b. The pillar portion 46a is provided on the arrow A side of the circular plate portion 45b, being united with the circular plate portion 45b. A semi-spherical insertion portion 46b, which diameter is bigger than one of the pillar portion 46a is provided on the arrow A side of the pillar portion 46a, united with the pillar portion 46a, directing a spherical surface 46c to the arrow A side.

The diameter of the pillar portion 46a is almost equal to the inside diameter of the boundary portion 35 between the second taper hole 32 and the third taper hole 33 of the piston engagement hole 29 provided at the hub 13, and the diameter of the insertion portion 46b is smaller than the inside diameter of the cylindrical hole 31 of the piston engagement hole 29.

On the other hand, a packing 47 made of flexible resin is supportingly provided with the packing support 45. The packing 47 is comprised of a pillar portion 49, which extends in the directions as shown by the arrows A and B, and a taper 50, connecting the arrow A side of the pillar portion 49, being united with the pillar portion 49. The outside diameter of the taper 50 is made narrower for the direction as shown by the arrow A. The form of the taper 50 allow the taper 50 to be inserted into the inside of the taper 6 of the syringe body 2 in a natural state so as to adjust to the inside of the taper 6.

A first hole 51, which diameter is the same as one of the pillar portion 45a of the packing support 45, and which length in the directions as shown by the arrows A and B is the same as one of the pillar portion 45a, is provided with the packing 47 in the direction as shown by the arrow A from an end face 49a side of the arrow B side of the pillar portion 49, coaxial with the pillar portion 49. Furthermore, a second hole 52, which diameter is the same as one of the circular plate portion 45b of the packing support 45, and which length in the directions as shown by the arrows A and B is the same as one of the circular plate portion 45b, is provided with the packing 47, connecting with the arrow A side of the first hole 51, coaxial with the pillar portion 49. And, a third hole 53, which diameter is the same as the outside diameter of the section perpendicular to the directions as shown by the arrows A and B of the insertion portion 46b of the hub engagement portion 46, and which length in the directions as shown by the arrows A and B is the same as one of the pillar portion 46a of the hub engagement portion 46 is provided with the packing 47, connecting with the arrow A side of the second hole 52, coaxial with the pillar portion 49. The third hole 53 is open on the taper 50 side of the packing 47 to the direction as shown by the arrow A.

In other words, the packing 47 is provided so as to engage with the packing support 45 such that the pillar portion 46a of the hub engagement portion 46 penetrates the third hole 53, the circular plate portion 45b of the packing support 45 is inserted into the second hole 52, and the pillar portion 45a of the packing support 45 penetrates the first hole 51.

Figure 3:
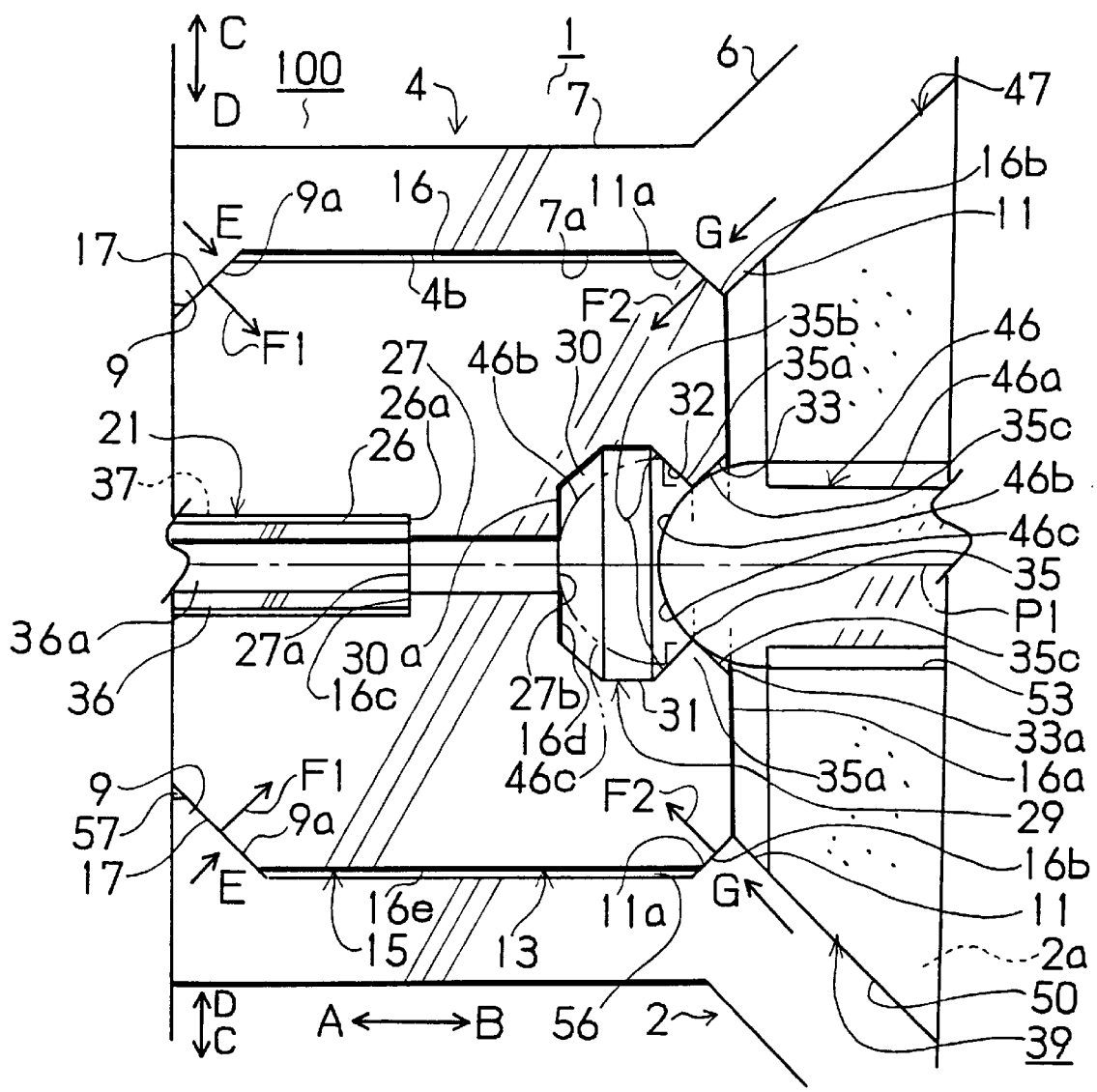
FIG. 3 is a view showing a routine of engaging the hub as shown in FIG. 2 with the piston.

In such a state that the taper 50 of the packing 47 is inserted and adjusted into the inside of the taper 6 of the syringe body 2 in a natural state, as shown in FIG. 3, the form of the packing 47 is set in such a manner that the spherical surface 46c of the insertion portion 46b of the hub engagement portion 46 of the arrow A side of the packing support 45 which is engaged with the packing 47 is in contact with the wall face 35c facing the third taper hole 33 of the piston engagement hole 29.

The diameter of the pillar portion 49 of the packing 47 is almost equal to one of the inner press plate 43. However, on the outer periphery side of the pillar portion 49 of the packing 47, annular folds 55 are double formed, being arraged in the directions as shown by the arrows A and B along the outer periphery of the pillar portion 49. Then, the pillar portion 49 and the fold 55 of the packing 47 are inserted into the main cylindrical portion 3 of the syringe body 2, reducing their sizes by elastic deformation in the direction for the axis center P1 (that is, in the direction as shown by the arrow D.). That is, the pillar portion 49 of the packing 47 and the fold 55 press the inner peripheral face 3c of the main cylindrical portion 3 with a force in the direction away from the axis center (that is, the direction as shown by the arrow C), and the part between the packing 47 and the main cylindrical portion D is sealed against water (or against air). Since the pillar portion 49 of the packing 47 applys a force so as to reduce the diameter of the first hole 51 and the second hole 52 to the first hole 51 side and the second hole 52 side of the packing 47, the packing support 45, inserted into the first hole 51 and the second hole 52, and the packing 47 are pressing each other so as to closely contact with each other. The part between the packing 47 and the packing support 45 is sealed against water (or against air).

The inner peripheral face 3c of the main cylindrical portion 3 of the syringe body 2 is smoothly formed, and then, the piston 39, into which the packing 37 is inserted, is slidable in the directions as shown by the arrows A and B in the inside space 2a of the main cylindrical portion 3.

The syringe assembly 1 is comprised as described hereinbefore. In order to assemble the syringe assembly 1, the following steps are executed.

That is, the syringe 100, the hub 13, the needle 36, the piston 39 and the packing 47, which are the comprising parts of the syringe assembly 1, are prepared. At first, the hub 13 is inserted into the syringe 100.

That is, the hub 13 is inserted into the inside space 2a of the syringe body 2 from the opening end 3a of the syringe body 2. The insertion is executed so as to face the third pillar portion 20 side of the hub 13 to the hub insertion portion 4 side of the syringe body 2 (the side of the arrow A of the figure). The hub 13 is further inserted into the hub insertion hole 4b to the arrow A side of the figure to the position where the seal taper 17 of the hub 13 abuts on the rib for holding 11 of the hub insertion hole 4b side. Since the outside diameter of the third pillar portion 20 and the second pillar portion 19 of the hub 13 is smaller than the inside diameter L1 in the portion of the rib for holding 11 in the first cylindrical portion 7, the hub 13 is smoothly inserted to the position where the seal taper 17 abuts on the rib for holding 11 of the hub insertion hole 4b side.

A force in the direction as shown by the arrow A is further added to the hub 13 after the seal taper 17 abuts on the rib for holding 11, thereby a stress in the direction perpendicular to the abutting face, and in the direction away from the axis center P1 is added to the rib for holding 11 in the point where the seal taper 17 and the rib for holding 11 of the hub 13 abut on each other. That is, by receiving this stress, the first small cylindrical portion 7 near the rib for holding 11 and the taper 6 elastically enlarge and expand in the direction away from the axis center P1 being perpendicular to the axis center P1, that is, in the direction as shown by the arrow C in the figure (At the same time, the hub body 15 and the like are elastically deformed in the direction reducing the diameter of it.).

The portion near the rib for holding 11 enlarges and expands in the direction as shown by the arrow C and the inside diameter of the first small cylindrical portion 7 in the rib for holding 11 becomes to be equal to the outside diameter of the first pillar portion 16, thereby the hub 13 receiving a force pressing in the direction as shown by the arrow A advances in the direction as shown by the arrow A. The hub 13 is further advanced in the direction as shown by the arrow A by pressing until the seal taper 17 of the hub 13 abuts on the outer peripheral face 9a of the insertion taper 9.

After the hub 13 advances until abutting, the hub 13 is further pressed in the direction as shown by the arrow A. By pressing, the hub 13 gives a stress in the direction perpendicular to the abutting face of the insertion taper 9 on which the hub 13 abuts on the arrow A side, that is, in the direction near the arrow A and in the direction near the arrow C, and the stress is transferred to the first small cylindrical portion 7 being unitedly provided with the insertion taper 9 as a stress in the direction as shown by the arrow A. Therefore, the first small cylindrical portion 7 is lengthened in the directions as shown by the arrows A and B by elastic deformation.

As the first small cylindrical portion 7 lengthens, the rib for holding 11 is moved along the outer peripheral face 16e relatively to the arrow B side against the hub 13, and the position of the rib for holding 11 and the position of the chamfer portion 16b of the hub 13 are matched to each other. Both are matched to each other, thereby the portion near the rib for holding 11 of the first small cylindrical portion 7 slightly returns. The rib for holding 11 and the hub 13 engage with each other in the chamfer portion 16b such that the side face 11a of the rib for holding 11 abuts on the chamfer portion 16b.

As the hub 13 advances in the direction as shown by the arrow A, the third cylindrical portion 20 of the hub 13 reaches the hole 12a of the end wall 12 which is at the corresponding position and is inserted into the hole 12a.

As explained heretofore, insertion of the hub 13 into the syringe 100 finishes. As described before, the hub 13 is fixed by the hub insertion portion 4 balancing respective forces between the hub 13 and the hub insertion portion 4.

The insertion operation of the hub 13 into the syringe 100 is executed by pressing the hub 13 so as to insert, and then, it is easy without complex assembling operations.

Subsequently, the packing 47 is inserted into the piston 39. In the first place, the first hole 51 of the packing 47 is broadened with hands or the like so as to equalize the diameter of the first hole 51 with one of the circular plate portion 45b of the packing support 45, making use of the flexibility of the packing 47. After that, the hub engagement portion 46 side of the piston 39 is inserted in the direction as shown by the arrow A from the first hole 51 side of the packing 47. Next, the piston 39 is further inserted until the insertion portion 46b of the hub engagement portion 46 passes and penetrates the third hole 53 of the packing 47 in the direction as shown by the arrow A and the insertion portion 46b projects on the side of the arrow A of the taper 50 of the packing 47, that is, the pillar portion 46a of the hub engagement portion 46 is inserted into the third hole 53 and the pillar portion 45a of the packing support 45 and the circular plate portion 45b are inserted into the first hole 51 and the second hole 52 which are respectively broadened.

After that, the hand by which the first hole 51 is broadened is left therefrom so as to return the packing 47 to its natural state, thereby the insertion of the packing 47 is finished.

Subsequently, the piston 39, into which the packing 47 is inserted, is inserted into the syringe body 2.

The insertion of the piston 39 is executed in such a manner that the side where the packing 47 of the piston 39 is inserted, is inserted into the inside space 2a of the syringe body 2 from the, opening end 3a side of the syringe body 2.

On this occasion, the outside diameter in the pillar portion 49 of the packing 47 and the fold 55 in a natural state is bigger than the inside diameter of the main cylindrical portion 3 of the syringe body 2. However, the packing 47 can be inserted into the inside space 2a of the syringe body 2 by reducing the outside diameter of the pillar portion 49 of the packing 47 and the fold 55 making use of the flexibility of the packing 47.

That is, the taper 50 side of the packing 47 is adjusted to the opening end 3a, and after that, the piston 39 is pressed in the direction as shown by the arrow A, thereby the packing 47 is inserted into the inside space 2a of the syringe body 2, adjusting to the inside space 2a of the syringe body 2, that is, reducing the outside diameter of the pillar portion 49 of the packing 47 and the fold 55.

Since the outside diameter of the inner press plate 43 and the width of the plate portion 40a of the piston body 40 are almost equal to the inside diameter of the main cylindrical portion 3 of the syringe body 2 (or smaller), the inner press plate 43 and the piston body 40 are smoothly inserted into the inside space 2a of the syringe body 2.

By inserting the piston 2 into the direction as shown by the arrow A, the packing 47 and the inner press plate 43 pass the position of the engagement rib 3b of the main cylindrical portion 3.

When passing the position of the engagement rib 3, the packing 47 receives the reaction against the force pressing the piston 2 in the direction as shown by the arrow A from the engagement rib 3, and passes reducing the outside diameter of the pillar portion 49 and the fold 55 so as to equalize with the inside diameter of the engagement rib 3b of the main cylindrical portion 3 of the syringe body 2 by the reaction.

When the inner press plate 43 passes the position of the engagement rib 3b following after the packing 47, the periphery side of the inner press plate 43, which outside diameter is bigger than the inside diameter of the engagement rib 3, abuts on the enagagement rib 3b. In case of abutting, the force pressing the piston 39 in the direction as shown by the arrow A elastically expands the portion near the engagement rib 3b of the main cylindrical portion 3 in the direction as shown by the arrow C through the inner press plate 43, and through the engagement rib 3b abutting on the inner press plate 43. Therefore, the inner press plate 43 passes the position of the engagement rib 3b, broadening the inside diameter in the engagement rib 3b. After the passing, the inner press plate 43 leaves from the engagement rib 3b, and then, no force expanding the main cylindrical portion 3 in the direction as shown by the arrow C acts, and the portion near engagement rib 3b of the main cylindrical portion 3 restores in the direction as shown by the arrow D.

After the packing 47 and the inner press plate 43 pass the position of the engagement rib 3b of the main cylindrical portion 3, the piston 39 is further inserted in the direction as shown by the arrow A, and as shown in FIG. 3, the piston 39 is inserted to the position, at which the taper 50 of the packing 47 is inserted and adjusted into the inside of the taper 6 of the syringe body 2, and then, the insertion of the piston 39 finishes.

In such a state that the taper 50 of the packing 47 is inserted and adjusted into the inside of the taper 6 of the syringe body 2, as shown in FIG. 3, the insertion portion 46b of the hub engagement portion 46 of the piston 39 exists in such a manner that the spherical surface 46c side of the insertion portion 46b is in contact with the wall face 35c facing the third taper hole 33 of the piston engagement hole 29, which is provided with the hub 13.

Subsequently, the needle 36 is inserted into the needle insertion hole 21 of the hub 13 so as to attach. That is, the needle 36 is inserted, from the rear end side of the needle 36, into the needle insertion hole 21 in the direction as shown by the arrow B, as shown in FIG. 2 till the rear end abuts on the wall face 16c of the hub 13 of the bottom of the needle insertion hole 21. After the insertion, the space between the hub 13 in the needle insertion hole 21 and the needle 36 is filled with the adhesive 37, and then, the adhesive 37 is hardened. Then, insertion of the needle 36 into the hub 13 finishes.

When the needle insertion hole 21 is filled with the adhesive 37, the adhesive 37 can flow to the bottom side of the needle insertion hole 21 (that is, the arrow B side) without forming a space in the needle insertion hole 21 to the utmost by the first taper hole 22 and the second taper hole 25 which are provided with the needle insertion hole 21.

Assembly of the syringe assembly 1 finishes by the end of insertion of the needle 36.

As described hereinbefore, most operations in assembly of the syringe assembly 1 (that is, all operations excluding one for insertion of the needle 36) are executed by pressing, and therefore, the assembly of the syringe assembly 1 is easy without complex operations.

The syringe assembly 1 assembled as shown before, is used and, after that, the syringe assembly 1 is discarded as follows.

At first, the syringe assembly 1 assembled is filled with a liquid injection medium 59. Filling it with the injection medium 59 is executed in such a manner that the main cylindrical portion 3 of the syringe body 2 of the syringe assembly 1 is grasped and supported with one hand, and the top end of the needle 36 of the syringe assembly 1 is inserted into the injection medium 59 which is inside of a medicine bottle (not shown), and after that, the piston 39 is pulled out against the syringe body 2 in the direction as shown by the arrow B with the outer press plate 42 of the piston 39 grasped by the other hand.

Of the inside space 2a of the syringe body 2, the space on the side of the arrow A rather than the packing 47 or the hub engagement portion 46, that is, a medium holding space 60 communicates with the outside of the top end side of the needle 36, that is, inside of a medicine bottle (not shown) through the medium flow hole 36a of the needle 36, the flow hole 27 and the piston engagement hole 29 of the hub 13 in the directions as shown by the arrows A and B. And, the medium holding space 60 is broadened by pulling the piston 39 against the syringe body 2 in the direction as shown by the arrow B, and then, the pressure of the air of the medium holding space 60 (or the injection medium 59) is lowered. Therefore, difference of pressure arises between the medium holding space 60 and the outside of the top end side of the needle 36, that is, inside of the medicine bottle (not shown), and the injection medium 59 in the medicine bottle flows in the medium holding space 60 through the medium flow hole 36a of the needle 36, and the flow hole 27 and the piston engagement hole 29 of the hub 13.

Filling with the injection medium 59 finishes in such a manner that the piston 39 is further pulled against the syringe body 2 in the direction as shown by the arrow B so as to further broaden the medium holding space 60 and so as to stream a predetermined amount of the injection medium 59 into the medium holding space 60.

On this occasion, difference of pressure arises between the medium holding space 60 and the outside of the medium holding space 60 at the time of filling with the injection medium 59, and therefore, a differential pressure force acts on the hub 13, which separates the medium holding space 60 from the outside of the medium holding space 60 in the direction as shown by the arrow B.

However, a predetermined seal pressure F1 acting between the hub 13 and the hub insertion hole 4b is set so as not to be zero or below zero against the maximum differential pressure force potential in the direction as shown by the arrow B (especially, in the seal pressure F1). Therefore, the hub 13 is supported by the rib for holding 11 in the direction as shown by the arrow A, and the portion between the insertion taper 9 of the hub insertion portion 4 and the seal taper 17 of the hub 13 is sealed with the seal pressure F1 (which is above zero).

That is, even if the injection medium 59 in the medium holding space 60 flows in the first gap space 56 between the hub 13 and the first small cylindrical portion 7, of the hub insertion hole 4b of the hub insertion portion 4, the injection medium 59 does not pass between the insertion taper 9 and the seal taper 17 and does not leak into the second gap space 57 between the hub 13 and the second small cylindrical portion 10 and the like since the portion between the insertion taper 9 and the seal taper 17 is sealed. In addition, outside air does not also flow from the second gap space 57 side to the first gap space 56 side.

On the other hand, in the packing 47, as described before, the pillar portion 49 and the fold 55 of the packing 47 are inserted into the main cylindrical portion 3 of the syringe body 2 reducing in the direction as shown by the arrow D by elastic deformation. That is, the pillar portion 49 of the packing 47 and the fold 55 press the inner peripheral face 3c of the main cylindrical portion 3 with a force in the direction as shown by the arrow C, and the portion between the packing 47 and the main cylindrical portion 3 is sealed against water (against air). That is, the injection medium 59 of the medium holding space 60 does not leak into the inside space 2a of the arrow B side of the packing 47 and the like, passing between the packing 47 and the main cylindrical portion 3.

In addition, since the pillar portion 49 of the packing 47 and the fold 55 are reduced in the direction as shown by the arrow D by elastic deformation, the packing support 45 of the piston 39, which is inserted into the first hole 51 and the second hole 52 of the packing 47, is pressed by the packing 47 in the direction as shown by the arrow D. That is, the portion between the packing 47 and the packing support 45 is closely sealed. Therefore, the injection medium 59 of the medium holding space 60 can flow to the third hole 53 of the packing 47, but the injection medium 46 does not any further pass between the packing 47 and the packing support 45 in the second hole 52 and the first hole 51, or leaking into the inside space 2a of the arrow B side of the packing 47 and the like.

After filling with the injection medium 59, the needle 36 of the syringe assembly 1 is stuck in a patient's injection portion with the main cylindrical portion 3 of the syringe assembly 1 supported with one hand.

Subsequently, the main cylindrical portion 3 of the syringe body 2 of the syringe assembly 1 is grasped with fingers of one hand, and the syringe support 5 is supported and fixed in the direction as shown by the arrow B from a plate face of the arrow A side of the syringe support 5 with the fingers which grasp the main cylindrical portion 3. The outer press plate 42 of the piston 39 is pressed in the direction as shown by the arrow A with other fingers (the thumb) of the same hand, by which the main cylindrical portion 3 is grasped, so as to drive the piston 39 to the syringe body 2 in the direction as shown by the arrow A. By drive of the piston 39, the capacity of the medium holding space 60 reduces, thereby the injection medium 59 in the medium holding space 60 is pressurized. By pressure, pressure difference arises between the medium holding space 60 and the outside of the top end side of the needle 36, that is, the body of a patient. Therefore, the injection medium 59 of the medium holding space 60 flows into the body in the injection part of a patient through the piston engagement hole 29 of the hub 13, the flow hole 27 and the medium flow hole 36a of the needle 36.

As described before, the injection medium 59 in the medium holding space 60 is pressurized and an action force by the pressure of the injection medium 59 is acted on the hub 13 in the direction as shown by the arrow A from the end face 16a side of the hub 13 adjacent to the injection medium 59.

However, the hub 13 can sufficiently receive a reaction in the direction as shown by the arrow B, resulting from its constitution, against the action force adding to the hub 13 in the direction as shown by the arrow A in the portion where the seal taper 17 of the hub 13 and the insertion taper 9 of the hub insertion portion 4 are closely contacted with each other. Therefore, the hub 13 is supported by the insertion taper 9 in the direction as shown by the arrow B. Since the size of the seal pressure F1 between the seal taper 17 and the insertion taper 9 increases by offering a reaction against the action force adding to the hub 13 in the direction as shown by the arrow A, the portion between the seal taper 17 and the insertion taper 9 is continuously sealed and water tight state (or air tight state) is maintained.

After the predetermined amount of the injection medium 59 is streamed in the body of a patient, that is, after the taper 50 of the packing 47 is inserted and adjusted into the inside of the taper 6 of the syringe body 2, and the piston 39 is driven until the insertion portion 46b of the hub engagement portion 46 of the piston 39 abuts on the third taper hole 33 of the piston engagement hole 29 of the hub 13, as shown in FIG. 3, the whole syringe assembly 1 is pulled in the direction as shown by the arrow B with respect to a patient through the hand or fingers supporting the syringe assembly 1 therewith so as to pull the needle 36 out of the injection part of a patient.

After pulling the needle 36, the piston 39 and the hub 13 are engaged with each other.

That is, the outer press plate 42 of the piston 39 is further pressed with a finger in the direction as shown by the arrow A.

Just after finish of the flow operation of the injection medium 59 into a body, the taper 50 of the packing 47 is inserted and adjusted inside of the taper 6 of the syringe body 2, the insertion portion 46b is inserted and adjusted inside of the third taper hole 33. Therefore, a force in the direction as shown by the arrow A acts on the packing 47 as the insertion portion 46b is advanced in the third taper hole 33 in the direction as shown by the arrow A by driving the piston 39. Since the packing 47 is supported by the taper 6 in the direction as shown by the arrow B, it can not move in the direction as shown by the arrow A. However, the packing 47 has flexibility, so the packing 47 remains there reducing itself in the directions as shown by the arrows A and B by elastic deformation so that the only insertion portion 46b moves in the direction as shown by the arrow A.

Since a force in the direction as shown by the arrow A is added to the piston 39 by pressing pressure, a pressing force in the direction as shown by the arrow A is added to the insertion portion 46b of the hub engagement portion 46. In addition, by this pressing pressure force, the forces in the direction in which the insertion portion 46b and the wall face 35c of the hub 13 facing the third taper hole 33 abut on each other, that is, in the direction perpendicular to the wall face 35c, act on each other between the insertion portion 46b and the huh 13 which are abutted on each other. Resulting from its constitution, the projection 35a of the hub 13 on which the insertion portion 46b abuts in the wall face 35c elastically deforms enlarging the diameter in an apex of the projection 35a, that is, the diameter in the boundary portion 35. At the same time, the insertion portion 46b elastically deforms reducing the diameter of the section perpendicular to the axis center P1.

The piston 39 is further pressed in the direction as shown by the arrow A so as to further advance the insertion portion 46b into the third taper hole 33 in the direction as shown by the arrow A. That is, the insertion portion 46b passes the boundary portion 35 in the direction as shown by the arrow A, reducing the diameter of the insertion portion 46b and enlarging the diameter of the boundary portion 35 so as to correspond the diameter of the insertion portion 46b with one of the boundary portion 35. After the whole insertion portion 46b completely passes the boundary portion 35, the press of the piston 39 finishes.

The whole insertion portion 46b completely passes the boundary portion 35, thereby the insertion portion 46b is inserted in the space formed by the first taper hole 30, the pillar hole 31 and the second taper hole 32 as shown by the two-dot chain line of FIG. 3 so as to adjust. The pillar portion 46a extending on the arrow B side of the insertion portion 46b exists penetrating the boundary portion 35 in the directions as shown by the arrows A and B. Then, the piston 39 and the hub 13 engage with each other.

The pressing force in the direction as shown by the arrow A acts on the insertion portion 46b, thereby the pressing force in the direction as shown by the arrow A acts on the hub 13 also. However, the hub 13 is supported in the direction as shown by the arrow B in the seal taper 17 by the insertion taper 9 of the hub insertion portion 4 with the hand by which the syringe body 2 is supported (or is supported by the wall face 12b of the end wall 12 in the end face 19a of the second pillar portion 19), and then receives a reaction in the direct-on as shown by the arrow B against the pressing force from the seal taper 17 (or the end wall 12). That is, the hub 13 does not almost move in the direction as shown by the arrow A or the like if receiving the pressing force. Therefore, the hub 13 is not pulled out of the hole 12a of the end wall 12 in the direction as shown by the arrow A.

After the piston 39 and the hub 13 are engaged with each other, the main cylindrical portion 3 of the syringe body 2 is supported with one hand, the outer press plate 42 is pulled against the syringe body 2 in the direction as shown by the arrow B with the other hand. By pulling the outer press plate 42, the action force in the direction as shown by the arrow B acts on the piston 39 and the insertion portion 46b of the hub engagement portion 46.

On this occasion, as shown in FIG. 3, this action force acts such that the forces are pressed to each other between the end portion of the arrow B side of the insertion portion 46b and the portion of the root side of the projection 35a. However, the end portion of the arrow B side of the insertion portion 46b and the portion of the root side of the projection 35a are hard to elastically deform for their constitution. Therefore, the insertion portion 46b is not pulled out of the piston engagement hole 29 passing through the boundary portion 35.

In this way, the action force in the direction as shown by the arrow B acts on the insertion portion 46b, thereby the action force in the direction as shown by the arrow B acts on the hub 13 by the insertion porton 46b engaged in the piston engagement hole 29. However, the hub 13 is not supported by the rib for holding 11 in the direction as shown by the arrow A against the action force in the direction as shown by the arrow B acting on the hub 13. Then, the portion near the rib for holding 11 of the first small cylindrical portion 7 (or the taper 6) receives the action force in the rib for holding 11 through the chamfer portion 16b of the hub 13, thereby it enlarges and expands in the direction as shown by the arrow C in the figure.

The action force in the direction as shown by the arrow B is further added to the piston 39 and the portion near the rib for holding 11 of the first small cylindrical portion 7 (or the taper 6) further enlarges and expands in the direction as shown by the arrow C in the figure, thereby the hub 13 is pulled out to the direction as shown by the arrow B passing through the portion of the rib for holding 11 of the first small cylindrical portion 7 which inside diameter enlarges rather than outside diameter L1' of the first pillar portion 16 of the hub 13. The piston 39 is continuously pulled in the direction as shown by the arrow B, thereby the hub 13 is further advanced in the direction as shown by the arrow B, and the hub 13 is pulled until it is completely pulled out of the first small cylindrical portion 7 in the direction as shown by the arrow B.

On this occasion, the outside diameter L1' of the first pillar portion 16 of the hub 13 is smaller than the inside diameter L1 of the first small cylindrical portion 7, and the outside diameter L2' of the second pillar portion 19 is smaller than the inside diameter L2 of the second small cylindrical portion 10. In addition, since the seal taper 17 and the insertion taper 9 are disposed so as not to interfere with the direction in which the hub 13 is pulled out, when the hub 13 is pulled out, the hub 13 and the hub insertion portion 4 are contacted with each other only between the chamfer portion 16b (or the outer peripheral face 16e of the first pillar portion 16) and the rib for holding 11. Therefore, the pulling operation can be easily executed with a small force after the chamfer portion 16b and the rib for holding 11 are disengaged from each other.

The piston 39 is further pulled and the needle 36, which is inserted and fixed on the arrow A side of the hub 13, inserts into the hub insertion hole 4b from the hole 12a of the end wall 12 in the direction as shown by the arrow B, and further inserts in the inside space 2a of the main cylindrical portion 3 in the direction as shown by the arrow B, and the piston 39 is pulled in the direction as shown by the arrow B such that the top end of the needle 36 is completely inserted into the inside space 2a.

Figure 4:
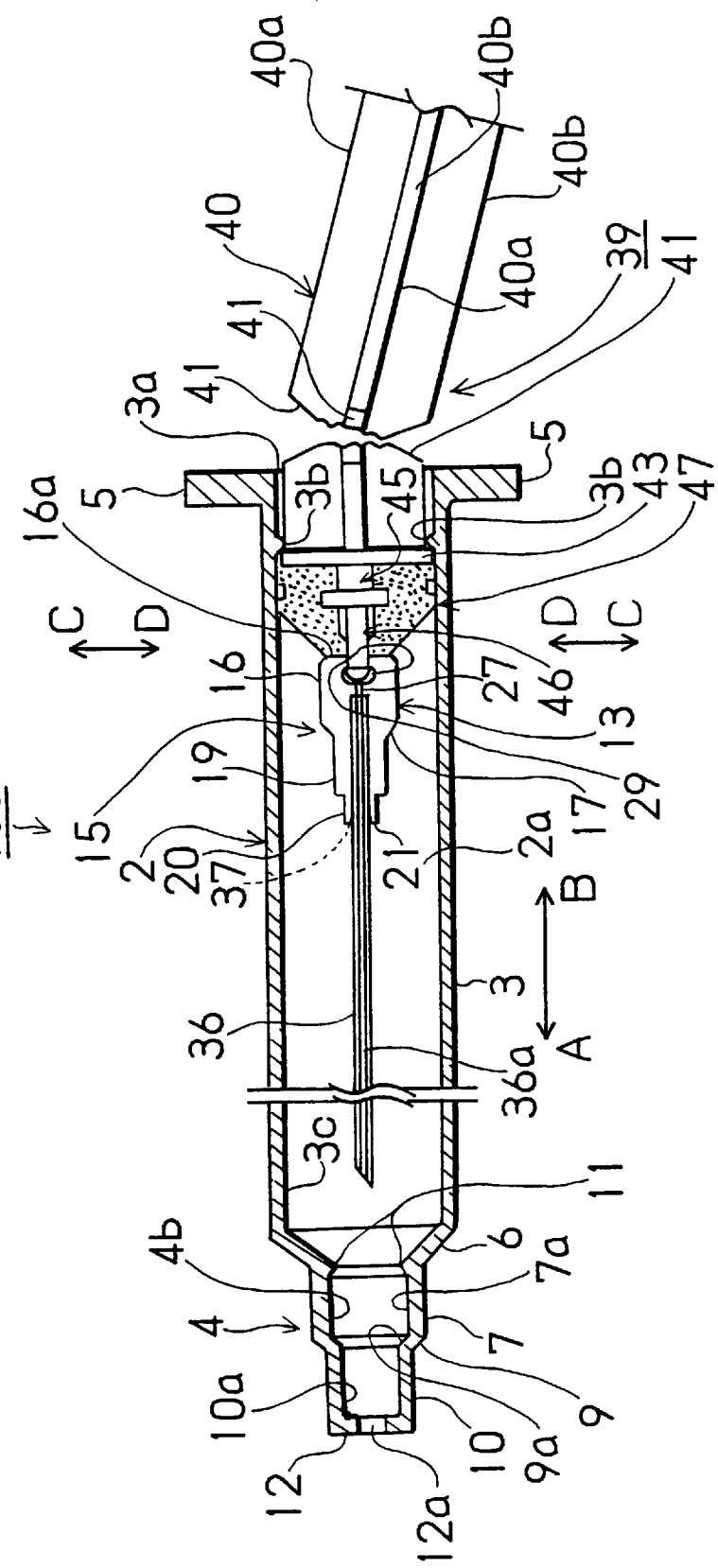
FIG. 4 is a view showing bending and taking of the piston in the syringe assembly as shown in FIG. 1.

The piston 39 is further pulled till the inner press plate 43 abuts on the engagement rib 3b of the main cylindrical portion 3 of the syringe body 2, as shown in FIG. 4, and the piston 39 is stopped.

On this occasion, the inner press plate 43 of the piston 39 is engaged with and stopped by the engagement rib 3b so as to prevent the needle 36 inserted into the hub 13 engaged with the piston 39 from springing to the outside the syringe body 2, by excessively pulling the piston 39 by mistake. In addition, the accident of secondary infection or the like generating from the hurt of hands and the like by the needle 36 can be prevented.

And, in such a state that the inner press plate 43 of the piston 39 is engaged with and stopped by the engagement rib 3b, the position of the notch 41 formed on the piston body 40 of the piston 39 is adjusted to the position of the opening end 3a of the syringe body 2 in the direction as shown by the arrows A and B, as shown in FIG. 4.

Subsequently, while the syringe body 2 is fixed with one hand, the piston 39 is grasped with the other hand, and as shown in FIG. 4, a force in the direction as shown by the arrow C is added to the piston 39. By adding a force in the direction as shown by the arrow C to the piston 39 with respect to the syringe body 2, bending stress is added to the piston body 40 with the engagement rib 3b and the opening end 3a of the syringe body 2 as a supporting point, and then the piston body 40 is broken in the notch 41, in which the structure of the piston body 40 is relatively weak with respect to bending stress, and the piston body 40 is separated into the arrow A side portion and the arrow B side portion forming a boundary with the notch 41.

By making the engagement rib 3b and the opening end 3a of the syringe body 2 a supporting point, bending stress can be effectively added to the piston body 40 using a principle of a lever. In addition, since the position of the notch 41 is at the position of the opening end 3a, that is, the position of the supporting point, the bending stress adding to the piston body 40 is effectively added to the portion of the notch 41. Therefore, the piston body 40 can be easily bent so as to be separated, that is, easily folded and taken.

Subsequently, the portion of the syringe body 2 side folded and taken and the portion of the outer press plate 42 of the piston 39 are disposed of so as to be discarded.

Since the needle 36 is completely inserted and stored in the inside space 2a of the syringe body 2 being held with the top end portion of the piston 39 remaining in the inside space 2a, there is no fear of hurting hands or the like and being secondarily infected from a wound by the needle 36. Therefore, waste disposal can be safety executed. And, the piston 39 is folded and taken, thereby the syringe assembly 1 folded and taken is not bulky, and then waste disposal can be smoothly executed. As described before, the use of the syringe assembly 1 and waste disposal after use all finish.

As described heretofore, the hub 13 of the syringe assembly 1 has the hub body 15 in the shape of a cylinder, through which the hub 13 is inserted into the hub insertion hole 4b and is pulled out of the hub insertion hole 4b to the syringe body 2. The chamfer portion 16b is provided with the hub body 15 so as to engage with the inner face of the hub insertion hole 4b. The piston engagement hole 29 is provided with the end face 16a of the hub body 15 so as to engage with the piston 39. The seal taper 17, which outside diameter is made narrower for the end face 20a side of the hub body 15, is annularly provided with the hub body 15 so as to abut on and contact with the inner face of the hub insertion hole 4b.

Then, the hub 13 and the hub insertion hole 4b can be contacted with each other through the seal taper 17 and the chamfer portion 16b. It is easy to attach and detach the hub 13 to and from the hub insertion hole 4b. In addition, a predetermined seal efficiency and a predetermined holding efficiency can be exercised between the hub 13 and the hub insertion hole 4b, and the disposing operation of the hub 13 in case of assembly and the pulling operation of the needle 36 used into the syringe assembly 1 can be smoothly and easily executed.

The connecting structure of the hub 13 is as follows. The hub body 15 is attachably and detachably inserted into the hub insertion hole 4b so as to insert into the hub insertion hole 4b and to pull out the hub insertion hole 4b to the syringe body 2. The insertion taper 9, which inside diameter is made narrower for the top end side of the syringe body 2, is annularly provided with the hub insertion hole 4b. And, the seal taper 17 of the hub body 15 is provided with the hub insertion hole 4b so as to be contacted with the insertion taper 9 with the seal pressure F1. The rib for holding is provided with the inner peripheral face of the hub insertion hole 4b so as to engage with the chamfer portion 16b of the hub body 15 such that the hub body 15 is free to be held and released with the holding force F2.

Then, the hub 13 and the inner peripheral face of the hub insertion hole 4b are contacted with each other through the seal taper 17 and the insertion taper 9, and the chamfer portion 16b and the rib for holding 11. It is easily executed to attach and detach the hub 13 to and from the hub insertion hole 4b, and the assembly operation of the syringe assembly 1 can be effectively executed. In addition, the direction in which the hub 13 is pulled is one in which the seal taper 17 is separated from the insertion taper 9 when the needle 36 used is withdrawn to the syringe assembly 1. Therefore, the hub 13 can be withdrawn inside of the syringe assembly 1 with a small pulling force making use of the seal pressure F1. The discarding operation of the used syringe assembly 1 can be smoothly and easily executed.

Besides, the syringe assembly 1 having the connecting structure of the hub 13, above described, can be withdrawn to the inside space 2a of the syringe 100 together with the needle 36 by engaging the hub 13 with the hub engagement portion 46 of the piston 39 after injection. The used needle 36 can be easily withdrawn to the inside space 2a of the syringe 100 by only pushing and pulling the piston 39, in a similar way to the operation of an usual syringe assembly, and then its operation is easy for every one. Besides, there is no danger of error operation and safety is secured.

The piston 39 is comprised such that the piston body 40 is free to be bent and taken between the outer press plate 42 and the inner press plate 43. Therefore, the needle 36 can remain such that the top end portion of the piston 39 holding the needle 36 is held in the inside space 2a of the syringe 100 by bending and taking the piston 39, thereby it is not operable from the outside. High safety is secured in case of disposal operation after that.

In addition, the engagement rib 3b is provided with the syringe body 2 so that the inner press plate 43 of the piston 39 is not pulled out of the syringe body 2. Therefore, it is possible to prevent an operator from hurting with the needle 36 used by inadvertently pulling the piston 39 out of the syringe body 2 when the piston 39 is moved together with the needle 36. Therefore, high safety is secured.

The notches 41 are provided with the piston body 40 of the piston 39. Then, the operation of bending and taking of the piston 39 can be easily executed by making use of the notches 41.

In addition, the notch 41 is formed so as to be positioned at the opening end 3a of the syringe body 2 when the piston 39 abutting on the engagement rib 3b. Therefore, the piston 39 is pulled till it abuts on the engagement rib 3b, and after that, the piston 39 can be immediately bend and taken by making use of the opening end 3a, and the operation of storing and remaining the needle 36 in the inside space 2a of the syringe 100 can be successively executed. Therefore, the operations of injection and disposal can be effectively executed.

The hub 13 explained in the above-mentioned embodiment, is comprised such that the held portion of the hub is the chamfer portion 16b of the periphery of the end face 16a. However, the hub of the present invention may be comprised such that the held portion of the hub is formed at a position different from one of the end face 16a.

Figure 5:
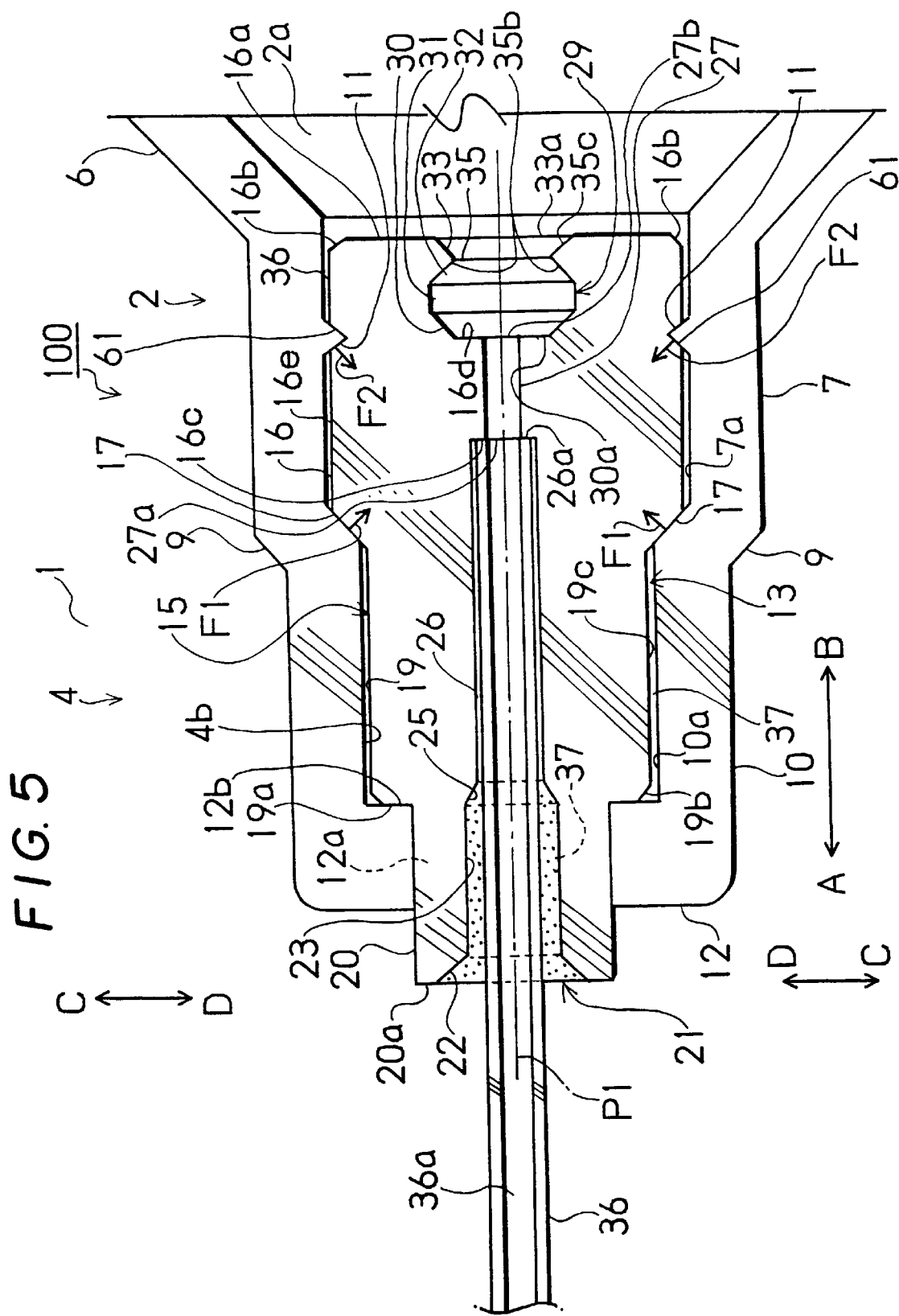
FIG. 5 is a view showing an example of the hub in which a held portion is formed in the shape of a groove.

That is, as shown in FIG. 5, the hub 13 may be comprised such that a held groove 61 in the shape of a groove is annularly formed on the outer periphery face 16e side of the first pillar portion 16 of the hub 13. In case where the held groove 61 is annularly formed, the rib for holding 11 of the hub insertion hole 4b side is formed at the position corresponding to the held groove 61 (On this occasion, the sectional form of the groove 61 can be adequately decided. Besides, it is of course possible that the sectional form is comprised so as to exercise seal action between the groove 61 and the rib 11. This point is similar to the case of FIG. 6 described hereinafter).

In case where a held portion is the held groove 61 also, a predetermined holding efficiency can be exercised between the hub 13 and the hub insertion hole 4b by engaging the held groove 61 and the rib for holding 11 with each other.

The hub 13 explained in the two embodiments above-mentioned is comprised such that the holding portion of the hub insertion hole is in the shape of a projection. However, it is possible that the holding portion of the hub insertion hole is formed in the shape of a groove. In case where the holding portion of the hub insertion hole is formed in the shape of a groove, the held portion of the hub corresponded to and engaged with the holding portion of the hub insertion hole is formed in the shape of a projection.

Figure 6:
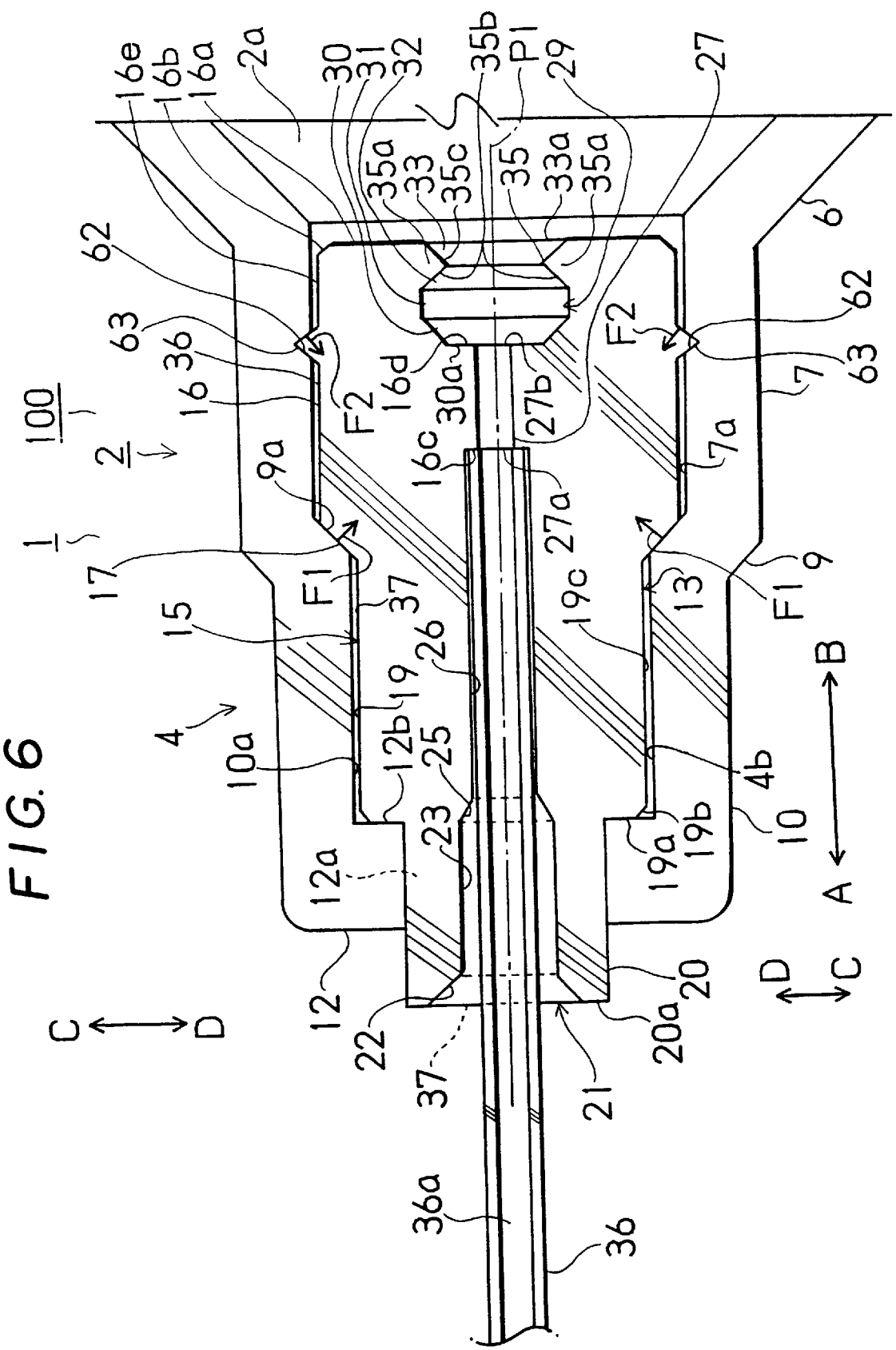
FIG. 6 is a view showing an example of a hub insertion hole in which a holding portion is formed in the shape of a groove and the hub in which the held portion is formed in the shape of a projection.

That is, as shown in FIG. 6, a holding groove 62 may be annularly formed in the shape of a groove on the inner peripheral face 7a side of the first small cylindrical portion 7 of the hub insertion hole 4b, and a held rib 63 may be annularly formed in the shape of a projection so as to correspond to the holding groove 62 on the outer periphery face 16e side of the first pillar portion 16 of the hub 13.

In case where the holding portion is the holding groove 62 and the held portion is the held rib 63, a predetermined holding efficiency can be exercised between the hub 13 and the hub insertion hole 4b by engaging the holding groove 62 and the held rib 63 with each other.

Any of the holding portion of the hub insertion hole and the held portion of the hub, explained in the respective embodiments above-mentioned, is annularly formed along the hub insertion hole or the hub. However, the holding portion and the held portion may be formed in any shape, such as point shape or broken line shape, as well as annular shape, as long as a predetermined holding efficiency can be exercised between the hub insertion hole and the hub by engaging both with each other.

Another embodiment of the present invention will now be explained hereinafter.

Figure 8:
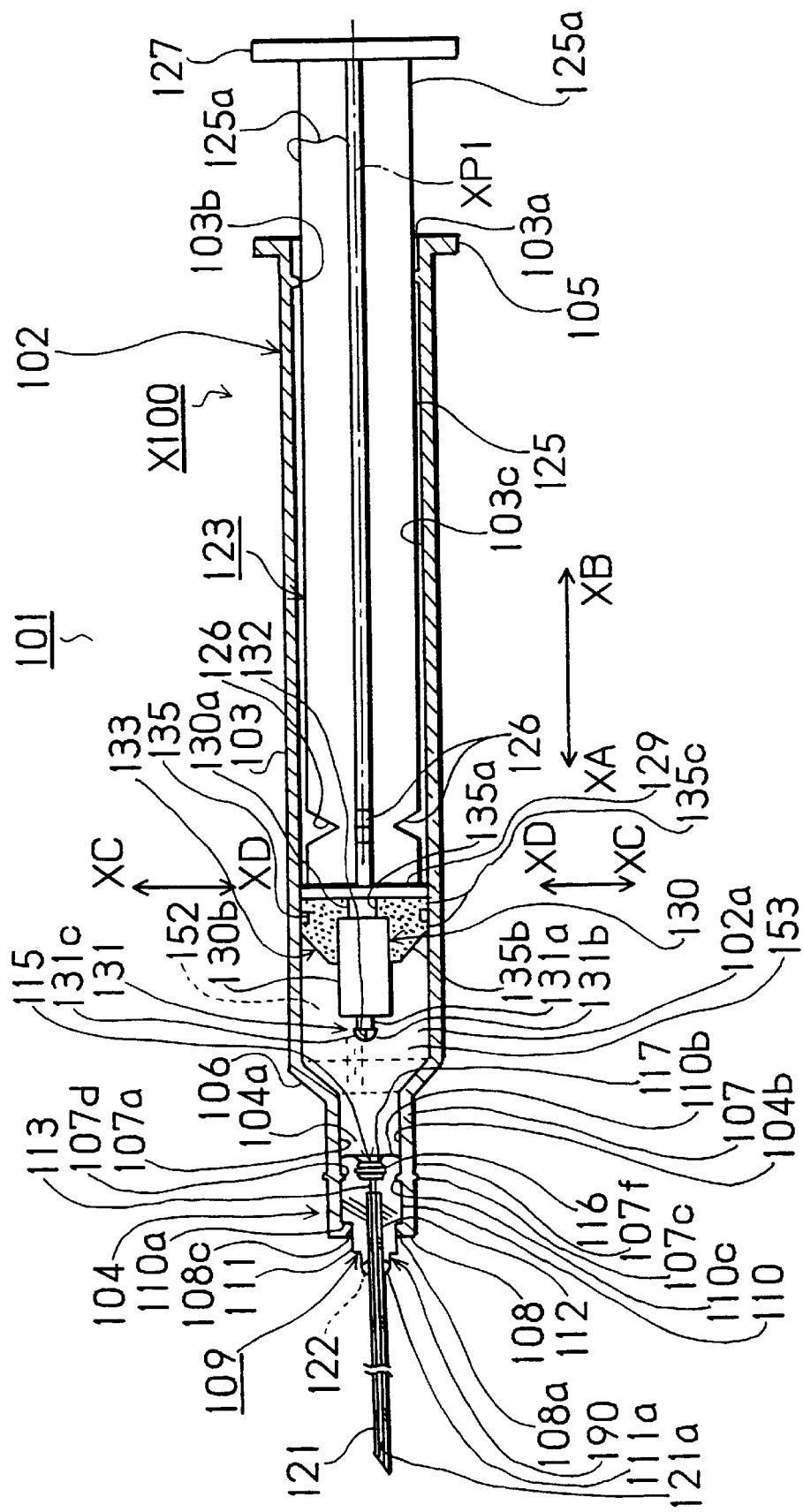
FIG. 8 is a view showing the whole syringe assembly as shown in FIG. 7.

A syringe assembly 101 according to the present invention has a syringe X100 made of resin, as shown in FIG. 8. A syringe body 102 is provided with the syringe X100 (FIG. 8 is a typical cross section of the syringe assembly 101, but a side is shown in a part of a piston 123, described hereinafter, not the section, for convenience.). A main cylindrical portion 103, cylindrically formed, is provided with the syringe body 102. A direction of an axis center of the main cylindrical portion 103, that is, the reciprocating directions parallel to an axis center XP1 are an arrow XA direction in the figure (or the left direction of the paper of FIG. 8) and an arrow XB direction (or the right direction of the paper of FIG. 8).

On the outer periphery side of the main cylindrical portion 103, a syringe support 105 is provided near an opening end 103a of the arrow XB side of the main cylindrical portion 103 (the right side of the paper of FIG. 8), in such a manner as forming a flange of the main cylindrical portion 103. On an inner peripheral face 103c side of the main cylindrical portion 103, an engagement rib 103b, projecting in the direction for the axis center XP1 of the main cylindrical portion 103, that is, the direction as shown by the arrow XD of the figure, is annularly formed near the opening end 103a along the inner peripheral face 103c.

On the arrow XA side of the main cylindrical portion 103 (the left side of the paper of FIG. 8) a taper 106 in the shape of a funnel, which inside is made narrower for the direction as shown by the arrow XA, is formed unitedly connecting with the main cylindrical portion 103.

The inside of the main cylindrical portion 103 and the inside of the taper 106 communicate with each other in the directions as shown by the arrows XA and XB, and the space into which both insides are combined is an inside space 102a of the syringe body 102.

Figure 7:
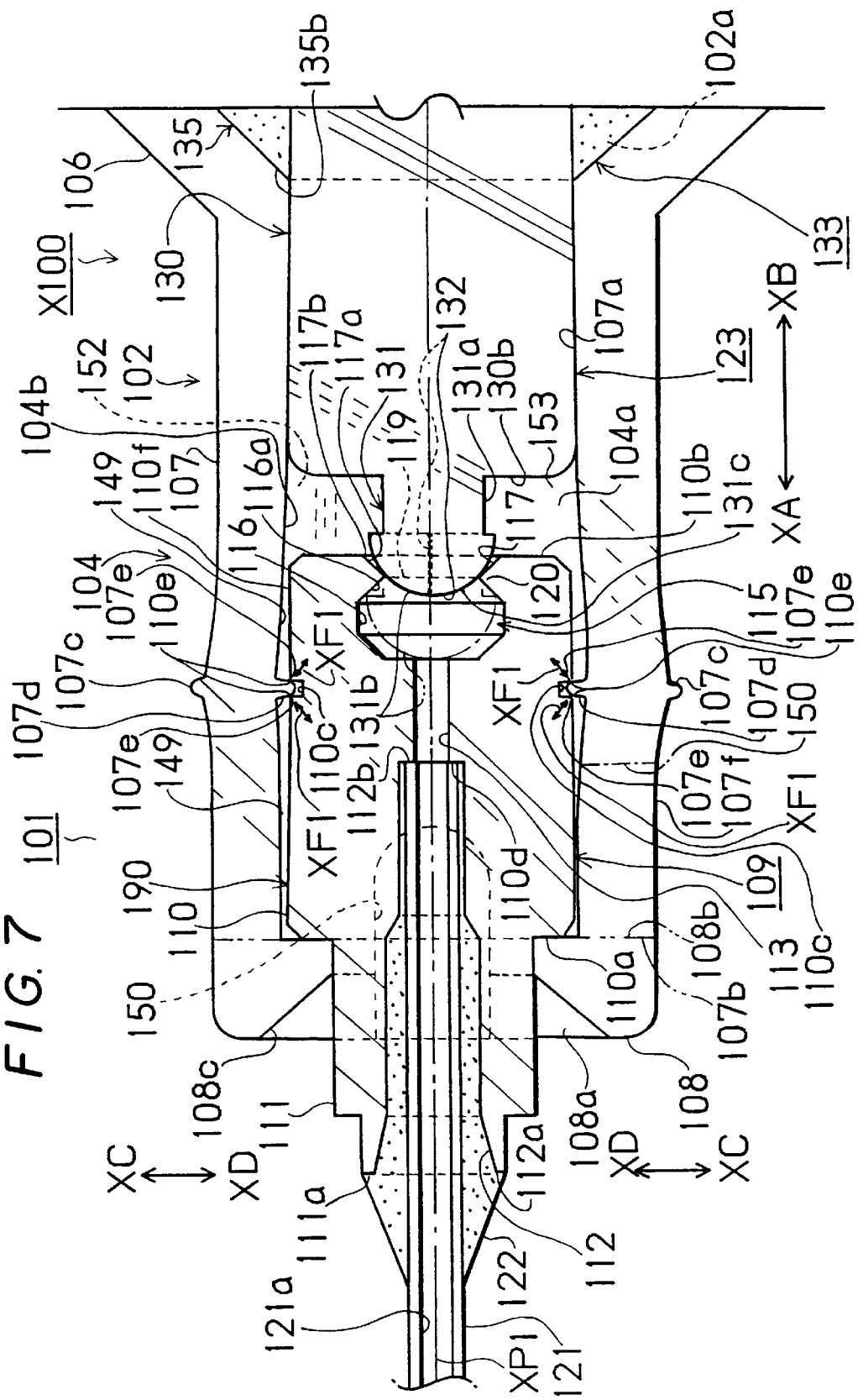
FIG. 7 is a typical sectional view showing an example of a syringe assembly according to the present invention.

On the side of the arrow XA of the taper 106, that is, on the side of the top of the syringe body 102, as shown in FIGS. 7 and 8, a hub insertion portion 104 is formed unitedly connecting with the taper 106, and the hub insertion portion 104 has a small cylindrical portion 107. The small cylindrical portion 107 is formed unitedly connecting with the taper 106 and coaxial with the main cylindrical portion 103. The inside diameter of the small cylindrical portion 107 is smaller than one of the main cylindrical portion 103.

The inside of the small cylindrical portion 107 is a hub insertion hole 104b. At the hub insertion hole 104b, a hub stop rib 107d is formed projecting for the axis center XP1.

The hub stop rib 107d is annularly formed along a smooth inner peripheral face 107a of the small cylindrical portion 107. A section of a plane including the axis center XP1 of the hub stop rib 107d (that is, a section as shown in FIG. 7) forms an arc.

On the other hand, a stiffening rib 107c is annularly formed at the position corresponding to the hub stop rib 107d putting the small cylindrical portion 107 therebetween on an outer peripheral face 107f side of the small cylindrical portion 107.

Figure 10:
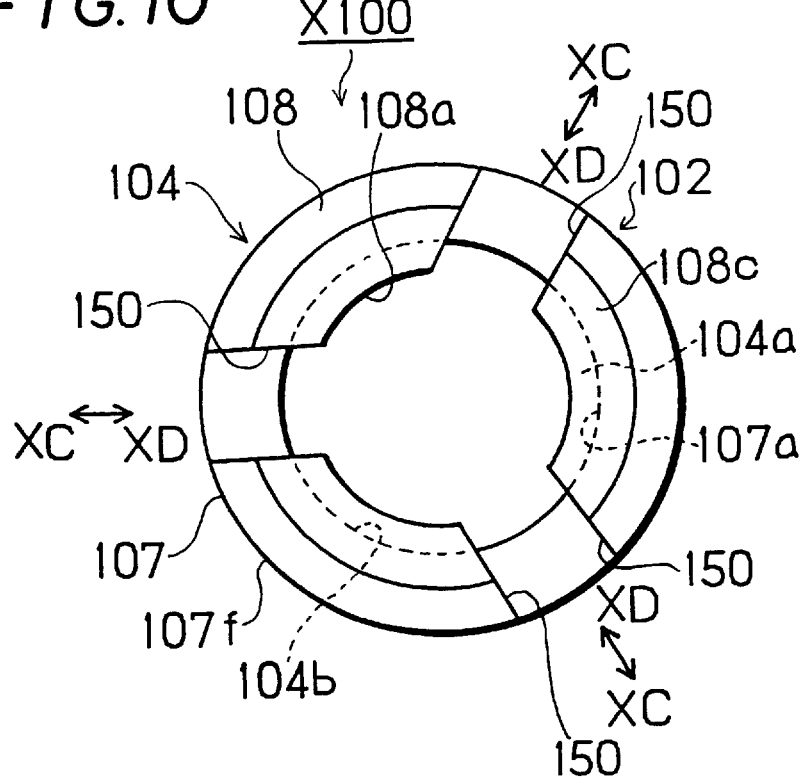
FIG. 10 is a view showing the hub insertion portion of the syringe assembly as shown in FIG. 7 seen from the arrow XB direction in the figure.

As shown in FIG. 7 or FIG. 10, an end wall 108, which outside diameter is equal to one of the small cylindrical portion 107 is provided in the shape of a disc with the small cylindrical portion 107. The end wall 108 is provided united with the small cylindrical portion 107 such that the wall face 108b of the arrow XB side of the end wall 108 and an end portion 107b of the arrow XA side of the small cylindrical portion 107 are contacted with each other. A hole 108a having a circular section, which center is the axis center XP1, is provided with the end wall 108 penetrating both front and back wall faces of the end wall 108 in the directions as shown by the arrows XA and XB. The arrow XA side of the hole 108a is taperingly formed such that a sectional inside diameter is made big for the arrow XA direction.

As shown in FIG. 7 or FIG. 10, three slits 150 are formed extending to the end wall 108 and the small cylindrical portion 107. The slits 150 are formed extending in a radial direction with respect to the axis cener XP1 in the end wall 108, that is, in the directions as shown by the arrows XC and XD in FIG. 10 (The arrow XC direction is opposite to the arrow XD direction.) and communicating with the hole 108a provided with the end wall 108, and are formed paralel to the directions as shown by the arrows XA and XB in the small cylindrical portion 107. The slits 150 are formed at the positions on the arrow XA side rather than the hub stop rib 107d and the stiffening rib 107c so as not to reach the hub stop rib 107d and the stiffening rib 107c.

The hub insertion portion 104 is comprised as explained before. The syringe X100 is comprised such that the syringe support 105, the main cylindrical portion 103 comprising the syringe body 102, the taper 106 and the hub insertion portion 104 are unitedly provided.

A hub 109 made of resin, which is harder than the syringe X100, is provided with the hub insertion hole 104b of the hub insertion portion 104. As shown in FIG. 7, the hub 109 has a hub body 190. A main pillar portion 110 in the shape of a cylinder, which longitudinal direction is parallel to the directions as shown by the arrows XA and XB, which axis ceter is the axis center XP1, is provided with the hub body 190.

On a smooth outer peripheral face 110f side of the main pillar portion 110, the hub stop groove 110c is formed. The hub stop groove 110c is annularly formed along the outer periphery side of the main pillar portion 110.

On an end face 110a of the arrow XA side of the main pillar portion 110, a small pillar portion 111 is provided extending in the directions as shown by the arrows XA and XB, coaxial and united with the main pillar portion 110.

As shown in FIG. 7, the hub 109 is provided such that the main pillar portion 110 of the hub 109 is inserted into the hub insertion hole 104b of the hub insertion portion 104, and the small pillar portion 111 of the hub 109 is inserted into the hole 108a of the end wall 108 so as to penetrate it. The hub stop rib 107d of the hub insertion portion 104 and the hub stop groove 110c of the hub 109 are at the positions corresponding to each other so as to adjust. Therefore, the hub stop rib 107d engages with the hub stop groove 110c such that the top end side in the shape of an arc of the arrow XD side is inserted into the hub stop groove 110c which is at the position corresponding to and matching with the hub stop rib 107d.

Since the width of the hub stop rib 107d in the directions as shown by the arrows XA and XB is broader than one of the hub stop groove 110c in the directions as shown by the arrows XA and XB, the hub stop rib 107d engages with the hub stop groove 110c abutting on opening ends 110e, 110e of both sides of the hub stop groove 110c in the directions as shown by the arrows XA and XB directions in seal portions 107e, 107e of the top being in the shape of a circular arc in the directions as shown by the arrows XA and XB.

On this occasion, the inner peripheral face 107a of the small cylindrical portion 107 does not contact with the outer peripheral face 110f of the hub 109 in the portions excluding the hub stop rib 107d, and a gap space 149 is formed between the inner peripheral face 107a and the outer peripheral face 110f (However, the portions excluding the hub stop rib 107d of the inner peripheral face 107a of the small cylindrical portion 107 and the outer peripheral face 110f of the hub 109 may contact with each other as long as the hub 109 can be easily inserted into the hub insertion portion 104 and the hub 109 can be easily pulled out of the hub insertion portion 104, both explained hereinafter.).

An end face 110b of the arrow XB side of the main pillar portion 110 of the hub 109 is positioned on the arrow XA side rather than the boundary between the hub insertion hole 104b and the inside space 102a (that is, the boundary between the inside of the small cylindrical portion 107 and the inside of the taper 106). A space on the arrow XB side rather than the end face 110b of the inside of the hub insertion hole 104b is a hole space 104a.

On the other hand, the hub insertion portion 104 is elastically deformed expanding the small cylindrical portion 107 in the direction as shown by the arrow XC in such a state that the hub 109 is provided with the hub insertion hole 104b. That is, a restoring force by elastic deformation of the small cylindrical portion 107 is transferred to the hub 109 through the hub stop rib 107d of the small cylindrical portion 107. That is, between the hub stop rib 107d and the hub 109, predetermined seal pressures XF1 by the restoring force act in the portion between the seal portion 107e and the opening end 110e of the hub stop groove 110c, which are contacted with each other, and then the portion between the seal portion 107e and the opening end 110e is in a water tight state or an air tight state.

Rigidity of the hub stop rib 107d and the portion near thereof is increased in the small cylindrical portion 107 by the stiffening rib 107c which is provided the position corresponding to the hub stop rib 107d putting the small cylindrical portion 107 therebetween, and then a predetermined restoring force by elastic deformation of the small cylindrical portion 107 can be effectively obtained (No stiffening rib 107c may be useful.).

As shown in FIG. 7, a needle insertion hole 112 is provided with the hub 9. By provision of the needle insertion hole 112, a circular opening 112a, which center is the axis center XP1 is formed at an end face 111a of the arrow XA side of the small pillar portion 111 of the hub 109, and the opening 112a extends from the end face 111a in the direction as shown by the arrow XB. An end portion 112b of the arrow XB side of the needle insertion hole 112 reaches the inside of the main pillar portion 110. The end portion 112b contacts with a wall face 110d of the main pillar portion 110. A taper is adequately formed such that the diameter of the needle insertion hole 112 is made narrower for the direction as shown by the arrow XB in the needle insertion hole 112.

On the other hand, a flow hole 113 is provided with the main pillar portion 10 of the hub 109 adjacent to the arrow XB side of the needle insertion hole 112. The flow hole 113, which center is the axis ceter XP1 and which diameter is smaller than one of the needle insertion hole 112 in the end portion 112b, is formed in the shape of a cylinder. The flow hole 113 communicates with the needle insertion hole 112 forming a circular opening at the wall face 110d of the main pillar portion 110.

A piston engagement hole 115, which section perpendicular to the axis center XP1 is a circle, is provided with the main pillar portion 110 of the hub 109 communicating with and adjacent to the arrow XB side of the flow hole 113, coaxial with the axis center XP1. An opening 117b, which is open outside in the end face 110b of the main pillar portion 110, is formed on the arrow XB side of the piston engagement hole 115.

The piston engagement hole 115 is comprised of two parts, that is, an engagement holding portion 116 of the arrow XA side and an introducing portion 117 of the arrow XB side. The engagement holding portion 116 having almost cylindrical shape, coaxial with the axis center XP1, has tapers which respective diameters are made narrower for the directions as shown by the arrows XA or XB in both end portions of the arrows XA and XB sides. The end portion side of the arrow XA of the engagement holding portion 116 connects with and is adjacent to the flow hole X113.

The end portion of the arrow XB side of the engagement holding portion 116 connects with and is adjacent to the introducing portion 117. The diameter of the introducing portion 117 is made bigger for the direction as shown by the arrow XB. Therefore, the portion between a wall face 116a facing the engagement holding portion 116 and a wall face 117a facing the introducing portion 117 of the main pillar portion 110 forms a projection 120 projecting for the axis center XP1 with a boundary portion 119 between the engagement holding portion 116 and the introducing portion 117 as an apex.

On the other hand, a needle 121 is inserted into the needle insertion hole 112 of the hub 109, as shown in FIG. 7 or FIG. 8. A top side of the needle 121 is positioned outside of the syringe body 102 and the needle 121 is inserted into the needle insertion hole 112 from a rear end side of it. The rear end of the needle 121 abuts on the wall face 110d formed on the arrow XB side of the needle 112. A medium flow hole 121a provided penetrating from the top end of the needle 121 to the rear end side and the flow hole 113 connect with and are adjacent to each other in the directions as shown by the arrows XA and XB.

An adhesive 122 is injected into the needle insertion hole 112 filling the portion between the needle 121 and the hub 109 therewith, and is hardened.

The piston 123 is provided with the syringe assembly 101, as shown in FIG. 7 or FIG. 8 (FIG. 8 is a typical sectional view of the syringe assembly 101, but with respect to a piston body 125, an outer press plate 127, an inner press plate 129, a packing support 130, a hub engagement portion 131 of the piston 123, described hereinafter, each section is not shown, but each side is shown, for convenience.).

The piston 123 has the bar-shaped piston body 125 extending in the directions as shown by the arrows XA and XB. The piston body 125 is comprised such that two congruent plate portions 125a, each which is a plate shaped rectangle especially long in the directions as shown by the arrows XA and XB, are unitedly cross provided with each other such that the sections thereof form the shape of a cross. The width perpendicular to the directions as shown by the arrows XA and XB of the plate face of the plate portion 125a is almost equal to the inside diameter in the engagement rib 103b of the main cylindrical portion 103, and the piston body 125 is inserted into the main cylindrical portion 103 through the opening end 103a from the arrow XA side of the piston body 125.

On each plate portion 125a of the piston body 125, notches 126 are formed from both side portions of the respective plate portions 125a, 125a in the direction of the axis center (that is, the axis center XP1) of the piston body 125 in the shape of a wedge near the direction as shown by the arrow XA. Four notches 126 are provided at the positions adjusted one another in the directions as shown by the arrows XA and XB.

The outer press plate 127, which plate face is a circular plate perpendicular to the directions as shown by the arrows XA and XB, is provided on the end portion side of the arrow XB side of the piston body 125, being united with the piston body 125.

The inner press plate 129, which plate face is a circular plate perpendicular to the directions as shown by the arrows XA and XB, is provided on the end portion side of the arrow XA side of the piston body 125 being united with the piston body 125 and coaxial with the piston body 125 (Therefore, the inner press plate 129 is positioned inside the main cylindrical portion 103.). The diameter of the inner press plate 129 is almost equal to the inside diameter of the main cylindrical portion 103 (Therefore, the diameter of the inner press plate 129 is bigger than the inside diameter in the engagement rib 103b of the main cylindrical portion 103.).

As shown in FIG. 8, the packing support 130 is provided with the inner press plate 129 on the arrow XA side. A pillar portion 130a in the shape of a circular cylinder, which extends in the directions as shown by the arrows XA and XB, is provided with the packing support 130, coaxial with the inner press plate 129. The diameter of the pillar portion 130a is smaller than one of the inner press plate 129, and the pillar portion 130a is provided on the arrow XA side of the inner press plate 129, being united with the inner press plate 129. On the arrow XA side of the pillar portion 130a, as shown in FIG. 7 or FIG. 8, an insertion pillar portion 130b in the shape of a circular cylinder, extending in the directions as shown by the arrows XA and XB, coaxial with the pillar portion 130a, having an outside diameter almost equal to an inside diameter of the small cylindrical portion 107, is provided united with the pillar portion 130a.

Figure 9:
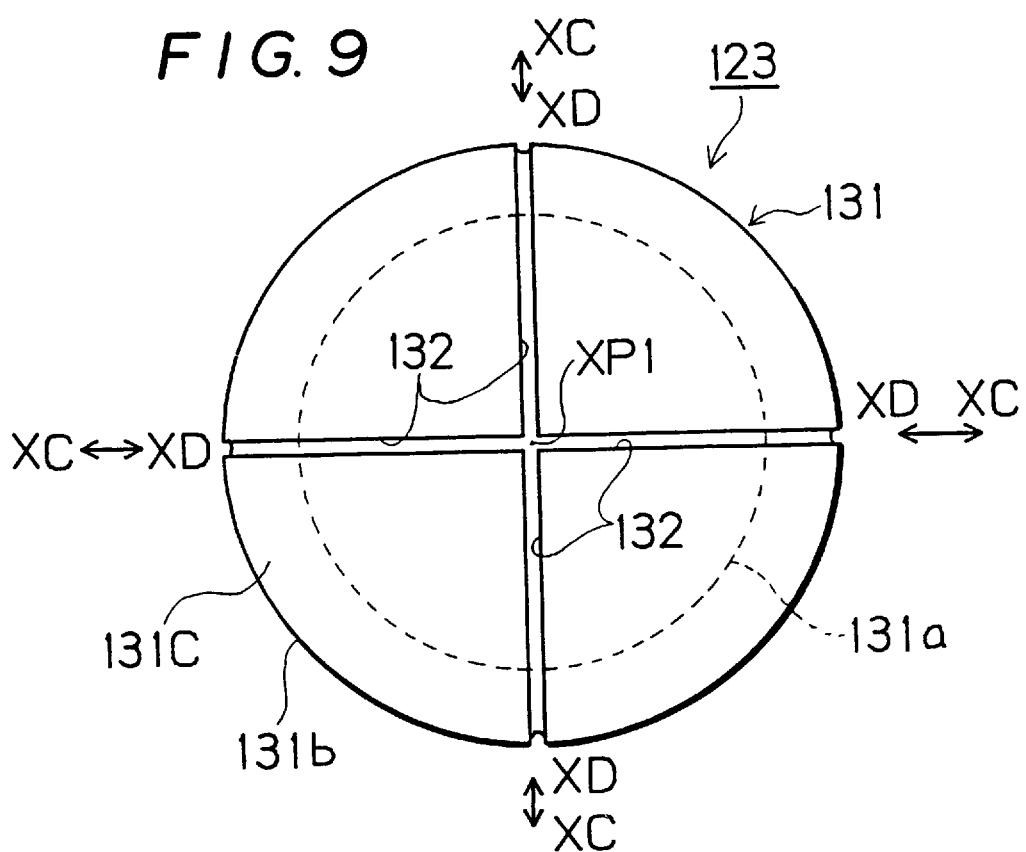
FIG. 9 is a view showing an insertion portion of a hub engagement portion of the syringe assembly as shown in FIG. 7 seen from the arrow XB direction of the figure.

The hub engagement portion 131 is provided on the arrow XA side of the insertion pillar portion 130b. As shown in FIG. 7 or FIG. 9, a pillar portion 131a being in the shape of a cylinder is provided with the hub engagement portion 131, extending in the directions as shown by the arrows XA and XB, coaxial with the insertion pillar portion 130b. The diameter of the pillar portion 131a is smaller than one of the insertion pillar portion 130b. The pillar portion 131a is provided on the arrow XA side of the insertion pillar portion 130b, united with the insertion pillar portion 130b. A semispherical insertion portion 131b, which diameter is bigger than one of the pillar portion 131a is provided on the arrow XA side of the pillar portion 131a, united with the pillar portion 131a, directing a spherical surface 131c side to the arrow XA side. A plurality of grooves 132 are provided in the shape of a stripe with the insertion portion 131b along the spherical face 131c extending from the top end portion of the arrow XA side to the arrow XB side.

The diameter of the pillar portion 131a is almost equal to the inside diameter of the boundary portion 119 of the piston engagement hole 115 provided with the hub 109. Therefore, the diameter of the insertion portion 131b is bigger than one of the boundary portion 119. The side of the insertion portion 131b is set so as to fully be inserted into and held by the engagement holding portion 116 of the piston engagement hole 115.

On the other hand, a packing 133 made of flexible resin is supportingly provided with the packing support 130, as shown in FIG. 8. The packing 133 has a packing body 135 inserted inside of the main cylindrical portion 103 of the syringe X100 so as to adjust. An engagement hole 135a is provided with the packing body 135 penetrating the packing body 135 in the directions as shown by the arrows XA and XB. The pillar portion 130a of the packing support 130 and a part of the insertion pillar portion 130 penetrate the engagement hole 135a. That is, the packing 133 engages with the packing support 130 such that the packing support 130 penetrates the engagement hole 135a, and is provided being supported by the packing support 130 by the engagement. The packing 133 in the engagement hole 135a and the packing support 130 are closely contacted with each other, that is, the portion therebetween is sealed against water or against air. The end portion of the arrow XB side of the packing body 135 abuts on the inner press plate 129 so as to easily receive a force in the direction as shown by the arrow XA by the inner press plate 129.

The arrow XA side of the packing body 135 has such a shape that it can be inserted and adjusted into the inside of the taper 106 of the syringe body 102 in a natural state, that is, the arrow XA side of it is a taper 135b taperingly formed, reducing its outside diameter for the direction as shown by the arrow XA. A portion of the arrow XA side of the insertion pillar portion 130b of the packing support 130 which is in a state of penetrating the engagement hole 135a projects on the arrow XA side rather than the taper 135b.

In such a state that the taper 135b of the packing 133 is inserted and adjusted into the inside of the taper 106 of the syringe body 102 in a natural state, as shown in FIG. 7, the form of the packing support 130 and the packing 133 is set in such a manner that the insertion pillar portion 130b of the packing support 130 engaging with the packing 133 is inserted into the hub insertion hole 104b of the syringe body 102 and the spherical face 131c of the insertion portion 131b of the hub engagement portion 131 contacts with the wall face 117a facing the introducing portion 117 of the piston engagement hole 115.

The outside diameter of the packing body 135 of the packing 133 is almost equal to one of the inner press plate 129. However, on the outer periphery side of the packing body 135, annular folds 135c are double formed, being arranged in the directions as shown by the arrows XA and XB along the outer periphery of the packing body 135. Therefore, the packing 133 is inserted into the main cylindrical portion 103 of the syringe body 102 reducing the portion near the fold 135c of the packing body 135 in the direction for the axis center XP1, that is, in the direction as shown by the arrow XD by elastic deformation. That is, the packing 133 and the main cylindrical portion 103 are closely contacted with each other in the fold 135c and the inner peripheral face 103c. The portion between the packing 133 and the main cylindrical portion 103 is sealed against water or against air.

The inner peripheral face 103c of the main cylindrical portion 103 of the syringe body 102 is smoothly formed, and then the piston 123 into which the packing 133 is inserted, is free to slide in the directions as shown by the arrows XA and XB directions in the inside space 102a of the main cylindrical portion 103.

The syringe assembly 101 is comprised as explained hereinbefore. In order to assemble the syringe assembly 101, the following steps are executed.

That is, the syringe X100, the hub 109, the needle 121, the piston 123 and the packing 133, which are the comprising parts of the syringe assembly 101, are prepared. At first, the packing 133 is inserted into the piston 123.

That is, the packing support 130 of the piston 123 is inserted into the engagement hole 135a by pressurizing it from the engagement portion 131 making use of flexibility of the packing 133 in such a manner that the insertion portion 131b of the hub engagement portion 131 of the piston 123 is adjusted to the opening end of the arrow XB side in the figure of the engagement hole 135a of the packing 133, and in the afore-mentioned state, the piston 123 is pressed to the packing 133 in the direction as shown by the arrow XA. The packing support 130 is engaged with the engagement hole 135a in a predetermined state in such a manner that the packing support 130 is inserted into the engagement hole 135a by pressurizing it, thereby insertion of the packing 133 to the piston 123 finishes.

Subsequently, the piston 123 into which the packing 133 is inserted, is inserted into the syringe body 102.

That is, after the taper 135b side of the packing 133 inserted the piston 123 therein is adjusted to the opening end 103a, the piston 123 is pressed to the syringe body 102 in the direction as shown by the arrow XA, thereby the packing 133 is inserted into the inside space 102a of the syringe body 102 while sliding, and the piston 123 inserted the packing 133 therein is inserted into the syringe body 102.

The piston 123 is inserted in the direction as shown by the arrow XA, thereby the packing 133 and the inner press plate 129 pass the position of the engagement rib 103b, of the main cylindrical portion 103, which inside diameter is reduced. When the packing 133 and the inner press plate 129 pass the position of the engagement rib 103b having the inside diameter smaller than the outside diameter of the packing 133 and the inner press plate 129, the piston 123 is pressed with a further big force in the direction as shown by the arrow XA, thereby the stress by this press is given to the engagement rib 103b from the inner press plate 129 so as to enlarge the inside diameter of the portion near the engagement rib 103b of the main cylindrical portion 103, or reaction force against this press is given to the packing 133 from the engagement rib 103b so as to make it pass there adequately reducing the outside diameter of the packing 133 by the reaction force.

The piston 123 is further inserted slidingly in the direction as shown by the arrow XA, and the piston 123 is inserted into the position where the taper 135b of the packing 133 is adjusted to the inside of the taper 106 of the syringe body 102, and then insertion of the piston 123 finishes.

Subsequently, the hub 109 is inserted into the hub insertion hole 104b from the hole 108a side of the end wall 108 of the hub insertion portion 104.

That is, the end face 110b of the arrow XB side of the hub 109 is adjusted to the hole 108a of the end wall 108, and in the afore-mentioned state, the hub 109 is pressed in the direction as shown by the arrow XB. As described before, three slits 150 are provided on the end wall 108 side of the hub insertion portion 104, and the end wall 108 side of the hub insertion portion 104 is divided into three parts. By pressing, the periphery near the end face 110b side of the hub 109 and a taper face 108c in the shape of a taper, facing the hole 108a of the end wall 108 are abutted on and pressed to each other, and an action force to elastically bend and deform the divided portions in the direction as shown by the arrow XC acts on the divided portions of the hub insertion portion 104. Since the divided portion of the hub insertion portion 104 is easy to elastically bend and deform in the direction as shown by the arrow XC for its structure in comparison with the other parts of the hub insertion portion 104 which are not divided, the divided portion of the hub insertion portion 104 elastically bends and deforms in the direction as shown by the arrow XC as the hub 109 is pressed so as to enlarge the diameter of the hole 108a.

The hub 109 is further pressed so as to enlarge the diameter of the hole 108a to make it equal to the outside diameter of the main pillar portion 110 of the hub 109. Then the hub 109 is inserted into the hub insertion hole 104b, and the main pillar portion 110 of the hub 109 is completely inserted into the hub insertion hole 104b, and then the pressing and insertion of the hub 109 are stopped.

Since the gap space 149 is formed between the outer peripheral face 110f of the main pillar portion 110 of the hub 109 and the inner peripheral face 107a in the portion having no hub stop rib 107d of the small cylindrical portion 107 (or since there is no contact enough to generate big frictional resistance between the outer peripheral face 110f and the inner peripheral face 107a excluding the hub stop rib 107d in case where no gap space 149 is formed.), the hub 109 is smoothly inserted into the hole space 104a of the small cylindrical portion 107.

At the position where the main pillar portion 110 of the hub 109 is completely inserted into the hub insertion hole 104b, the small pillar portion 111 is inserted into the hole 108a so as to penetrate it.

The positional relation between the hub stop rib 107d of the hub insertion portion 104 and the hub stop groove 110c of the hub 109 is formed as the main pillar portion 110 is completely inserted into the hub insertion hole 104b, and at the same time, each of them is at the position corresponding to and adjusting to each other, and both are engaged with each other such that the seal portions 107e, 107e of the hub stop rib 107d and the opening ends 110e, 110e of the hub stop groove 110c are respectively abutted on each other abutting on each other.

As explained heretofore, insertion of the hub 109 into the syringe body 102 finishes.

The hub 109, after insertion, exists in such a manner that the spherical face 131c side of the insertion portion 131b of the hub engagement portion 131 of the piston 123 is contacted with the wall face 117a facing the introducing portion 117 of the piston engagement hole 115 provided with the hub 109.

The insertion operation of the hub 109 into the syringe body 102 can be executed only by pressing the hub 109, and therefore, it is easy with no complex assembly operation.

Subsequently, the needle 121 is inserted into the needle insertion hole 12 of the hub 109 so as to be bonded. That is, the needle 121 is inserted into the needle insertion hole 112 from the rear end side of the needle 121 in the direction as shown by the arrow XB, as shown in FIG. 7 or FIG. 8, till the rear end abuts on the innermost wall face 110d of the hub 109 of the needle insertion hole 112. After insertion, the space between the hub 109 and the needle 121 in the needle insertion hole 112 is filled with the adhesive 122, and the adhesive 122 is hardened, after that the insertion of the needle 121 to the hub 109 finishes. Since the needle insertion hole 112 has portions taperingly formed, which inside diameter is made reduced for the direction as shown by the arrow XB, the adhesive 122 flows to innermost end of the arrow XB side of the needle insertion hole 112, so the filling with the adhesive 122 is certainly executed. Insertion and attachment of the needle 121 means end of assembly of the syringe assembly 101.

As described heretofore, the assembly of the syringe assembly 101 is easy with no complex operation since the most operations (that is, all the operations excluding the operation of inserting and fixing the needle 121) are executed by pressing. In addition, since the hub 109 is inserted after the piston 123 is inserted into the syringe body 102, dust entry into the inside space 102a is extremely prevented in case of insertion of the hub 109.

The assembly above-mentioned may be executed in such a manner that the needle 121 is inserted into the hub 109 in advance, and in the afore-mentioned state, the hub 109 inserted the needle 121 therein is inserted into the syringe body 102.

The syringe assembly 101 assembled as shown before, is used and, after that, the syringe assembly 101 is discarded as follows.

At first, the needle 121 of the syringe assembly 101 is advanced into an injection medium 152 in a medicine bottle (not shown), the piston 123 is pulled in the direction as shown by the arrow XB with respect to the syringe body 102, and by differential pressure, the injection medium 152 in the medicine bottle is flowed to a medium holding space 153 which is a space on the needle 121 side rather than the piston 123 of the hole space 104a and inside space 102a of the syringe body 102 on the right hand of FIG. 7 from the hub 109 of the hub insertion portion 104 passing through the medium flow hole 121a of the needle 121, the flow hole 113 of the hub 109 and the piston engagement hole 115 so as to fill the syringe assembly 101.

In case of filling with the injection medium 152, a differential pressure force in the direction as shown by the arrow XB by differential pressure between the outside and the medium holding space 153 acts on the hub 109. However, restoring force in the direction as shown by the arrow XD which the hub insertion portion 104 has is set in such a predetermined size as described heretofore, thereby seal pressures XF1 respectively act between each seal portion 107e and each opening end 110e on the arrow XA side and the arrow XB side between the hub 109 and the hub insertion hole 104 against the maximum differential pressure force predicted, and then sealing between the hub stop rib 107d and the hub 109 is not disengaged.

After filling with the injection medium 152, the needle 121 of the syringe assembly 101 is stuck-into an injection portion of a patient.

Subsequently, the outer press plate 127 of the piston 123 is pressed in the direction as shown by the arrow XA so as to drive the piston 123 with respect to the syringe body 102 in the direction as shown by the arrow XA. The injection medium 152 of the medium holding space 153 is pressurized so as to flow into the body in the injection portion of a patient through the piston engagement hole 115 of the hub 109, the flow hole 113, the medium flow hole 121a of the needle 121.

On this occasion, the injection medium 152 is pressurized and an action force by the pressure of the injection medium 152 is added to the hub 109 in the direction as shown by the arrow XA from the end face 110b side of the hub 109 adjacent to the injection medium 152. However, the restoring force in the direction as shown by the arrow XD which the hub insertion portion 104 has is set in such a predetermined size, thereby seal pressures XF1 respectively act between each seal portion 107e and each opening end 110e on the arrow XA side and the arrow XB side between the hub 109 and the hub insertion hole 104 against the maximum action force predicted, and then sealing between the hub stop rib 107d and the hub 109 is not disengaged.

After a predetermined amount of the injection medium 152 is flowed into the body in the injection portion of a patient, that is, after the taper 135b of the packing 133 is inserted into the inside of the taper 106 of the syringe body 102 so as to adjust into it, and as shown in FIG. 7, the piston 123 is driven until the insertion portion 131b of the hub engagement portion 131 of the piston 123 abuts on the wall face 117a in the introducing hole 117 of the piston engagement hole 115 of the hub 109, the whole syringe assembly 101 is pulled in the direction as shown by the arrow XB to a patient, and the needle 121 is pulled out of the injection portion of a patient.

After the needle 121 is pulled out, the operation of storing the needle is executed as follows.

In the operation of storing the needle, an engagement operation between the piston 123 and the hub 109 is executed as follows.

That is, the outer press plate 127 of the piston 123 is further pressed with fingers in the direction as shown by the arrow XA, and while the packing 133 is elastically reduced by pressing it to the taper 106 of the syringe body 102, the insertion pillar portion 130b of the packing support 130 and the hub engagement portion 131 are pressed and moved in the hub insertion hole 104b in the direction as shown by the arrow XA, and then the insertion portion 131b of the hub engagement portion 131 is pressed and moved from the introducing portion 117 of the piston engagement hole 115 for the engagement holding portion 116 in the direction as shown by the arrow XA.

That is, the piston 123 is pressed and moved in the direction as shown by the arrow XA, thereby the insertion portion 131b is pressed to the wall face 117a in the introducing portion 117. However, the arrow XA side of the insertion portion 131b is the spherical face 131c, and then the insertion portion 131b is formed in such a manner that the section perpendicular to the axis center XP1 is reduced for the direction as shown by the arrow XA. Then, the insertion portion 131b is pressed to the wall face 117a in this spherical face 131c. The inside of the introducing portion 117 is taperingly formed reducing for the direction as shown by the arrow XA. Therefore, the insertion portion 131b is pressed in the introducing portion 117 in the direction as shown by the arrow XA, thereby stresses by pressing pressure respectively acting between the insertion portion 131b and the projection 120 forming the wall face 117a respectively effectively act, elastically recuding the cross section perpendicular to the axis center XP1 for the insertion portion 131b, elastically enlarging the inside of the introducing portion 117 in the direction as shown by the arrow XC for the projection 120. As the result, the cross section perpendicular to the axis center XP1 of the insertion portion 131b is reduced, and the inside of the introducing portion 117 is enlarged in the direction as shown by the arrow XC, thereby the insertion portion 131b being pressed in the direction as shown by the arrow XA is moved in the introducing portion 117 in the direction as shown by the arrow XA.

As shown in FIG. 7, just before the start of the operation of storing a needle, the hole space 104a between the end face 110b of the hub 109 and the insertion pillar portion 130b of the piston 123 side (that is, the medium holding space 153) is filled with the remaining injection medium 152. The operation of storing the needle starts and the piston 123 is pressed and moved in the direction as shown by the arrow XA as described before, thereby the remaining injection medium 152 is pressurized. However, a plurality of grooves 132 are provided with the insertion portion 131b as described heretofore, these grooves 132 are not closed when the insertion portion 131b and the wall face 117a are abutted on each other by pressing. Therefore, when the insertion portion 131b and the wall face 117a are abutted on each other by pressing, the hole space 104a side and the engagement holding portion 116 side communicate with the grooves 132, and the remaining injection medium 152 pressurized in the hole space 104a flows to the engagement holding portion 116 side through the grooves 132, and then, is expelled outside through the flow hole 113 and the medium flow hole 121a of the needle 121. That is, when the operation of storing the needle starts and the piston 123 is pressed and moved in the direction as shown by the arrow XA, the remaining injection medium 152 pressurized in the hole space 104a is adequately expelled outside and the pressure is not extremely increased. Therefore, resistance by pressure of the remaining injection medium 152 is not extremely acted on the piston 123 and then the piston 123 is pressed and moved in the direction as shown by the arrow XA with an extremely small force.

The piston 123 is further pressed in the direction as shown by the arrow XA so as to further move the insertion portion 131b into the introducing portion 117 in the direction as shown by the arrow XA. That is, the insertion portion 131b is moved from the arrow XA side thereof to the engagement holding portion 116 side passing through the boundary portion 119 between the introducing portion 117 and the engagement holding portion 116, and the insertion portion 131b is completely inserted into the engagement holding portion 116 as shown by the two-dot chain line of FIG. 7, thereby the pressing of the piston 123 is stopped. The insertion portion 131b is completely inserted into the engagement holding portion 116, thereby the hub engagement portion 131 and the piston engagement hole 115 are engaged with each other and then the operation of engaging the piston 123 and the hub 109 with each other finishes.

A pressing pressure force in the direction as shown by the arrow XA acts on the insertion portion 131b, thereby a pressing pressure force in the direction as shown by the arrow XA acts on the nub 109 also. However, the hub 109 is supported or can be supported with the hand by which the syringe body 102 is supported, through the hub stop rib 107 of the hub insertion portion 104 or the end wall 108 in the direction as shown by the arrow XB. Therefore, the hub 109 does not almost move in the direction as shown by the arrow XA and the like if receiving a pressing pressure force, and the hub 109 is not pulled out of the hole 108a of the end wall 108 in the direction as shown by the arrow XA.

Subsequently, the piston 123 is pulled with a predetermined pulling force against the syringe body 102 in the direction as shown by the arrow XB. That is, an action force in the direction as shown by the arrow XB by a predetermined pulling force acts on the piston 123 and the insertion portion 131b of the hub engagement portion 131. The restoring force in the direction as shown by the arrow XD which the hub insertion portion 104 has is set in such a predetermined size described heretofore. Therefore, the seal between each seal portion 107e and each opening end 110e of the arrows XA and XB sides between the hub 109 and the hub insertion portion 104 is disengaged against the action force in the direction as shown by the arrow XB by a predetermined pulling force, and then engagement between the hub stop rib 107d and the hub stop groove 110c is disengaged. The engagement between the hub stop rib 107d and the hub stop groove 110c is disengaged and the hub 109 is further advanced in the direction as shown by the arrow XB so as to be pulled until the hub 109 is completely pulled out of the hub insertion hole 104b in the direction as shown by the arrow XB.

On this occasion, the insertion portion 131b of the hub engagement portion 131 inserted into the engagement holding portion 116 of the piston engagement hole 115 is pressed for the wall face 116a of the engagement holding portion 116 in the direction as shown by the arrow XB by pulling in the direction as shown by the arrow XB, as described before. However, the portion where the insertion portion 131b and the wall face 116a are abutted on each other by pressing is one of the end portion of the arrow XB side in the insertion portion 131b, that is, one which outside diameter is biggest. Besides, since the portion which the insertion portion 131b abuts on is the base side, that is, the side where the wall is thick, of the projection 120, the insertion portion 131b and the projection 120 are in such a state that they are hard to elastically deformed for their constitution against the reaction receiving in the portion where the insertion portion 131b and the wall face 116a are abutted on each other, from the wall face 116a side or the insertion portion 131b side. Therefore, the insertion portion 131b is not pulled outside of the engagement holding portion 116 by the above-mentioned pulling in the direction as shown by the arrow XB. Then, the engagement between the piston 123 and the hub 109 is certainly maintained.

When the hub 109 is pulled out, since the gap space 149 is formed between the outer peripheral face 110f of the main pillar portion 110 of the hub 109 and the inner peripheral face 107a of the portions having no hub stop rib 107d of the small cylindrical portion 107 (or since there is no contact enough to generate big frictional resistance between the outer peripheral face 110f and the inner peripheral face 107a excluding the hub stop rib 107d if no gap space 149 is formed), the pulling operation can be executed with a small force after the engagement between the hub stop rib 107d and the hub stop groove 110c is disengaged.

The piston 123 is further pulled in the direction as shown by the arrow XB in such a manner that the needle 121 inserted and fixed on the arrow XA side of the hub 109 is inserted into the hub insertion hole 104b in the direction as shown by the arrow XB from the hole 108a of the end wall 108 and further inserted into the inside space 102a of the main cylindrical portion 103 in the direction as shown by the arrow XB, and the top end of the needle 121 is completely inserted into the inside space 102a.

The piston 123 is further pulled until the inner press plate 129 abuts on the engagement rib 103b of the main cylindrical portion 103 of the syringe body 102, and then the piston 123 is stopped.

Figure 11:
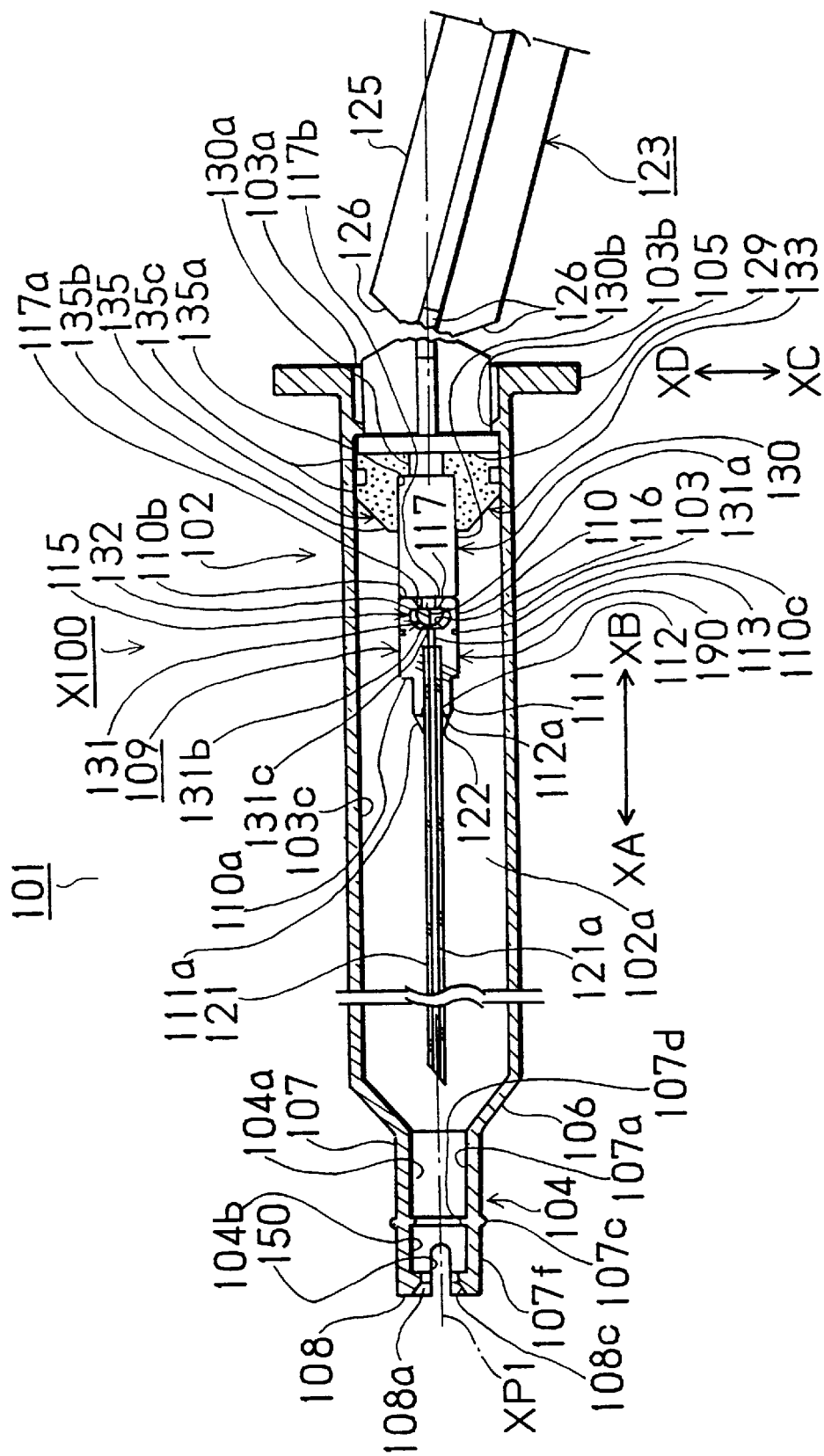
FIG. 11 is a view showing bending and taking of the piston in the syringe assembly as shown in FIG. 7.

Then, as shown in FIG. 11, the notch 126 of the piston body 125 is positioned near the opening end 103a of the syringe body 102. Subsequently, a force in the direction as shown by the arrow XC is given to the piston 123. A force in the direction as shown by the arrow XC is added to the piston 123 with respect to the syringe body 102, thereby the piston body 125 is bent in the notch 126 which structure is relatively weak against bending stress in the piston body 125, and the piston body 125 is divided into the arrow XA side portion and the arrow XB side portion forming a boundary by the notch 126.

Since the inner press plate 129 is abutted on the engagement rib 103b and stopped, a force in the direction as shown by the arrow XC added to the piston 123 is effectively acting on the notch 126 of the piston body 125 with the portion where the inner press plate 129 and the engagement rib 103b are abutted on each other as its supporting point when the piston body 125 is bent and taken, applying a principle of lever. Therefore, the piston 125 can be easily bent and taken.

Subsequently, the portion of the syringe body 102 side bent and taken and the portion of the outer press plate 127 of the piston 123 are disposed of so as to be discarded. Since the needle 121 is completely inserted and stored in the inside space 102a of the syringe body 102 being held with the top end portion of the piston 123 remaining in the inside space, there is no fear of hurting hands or the like and being secondarily infected from a wound by the needle 121. Therefore, waste disposal can be safely executed. As described before, the operation of storing the needle finishes and the use of the syringe assembly 101 and waste disposal after use all finish.

In the syringe assembly 101 explained in the above-mentioned embodiment, the slits 150 are formed at the sringe X100. However, no slit 150 may be formed at the syringe X100 of the syringe assembly 101.

In case where the syringe assembly 101 having no slit 150 at the syringe X100 is assembled, when the hub 109 is inserted into the hub insertion hole 104b, in first, the hub 109 is inserted into the inside space 102a from the opening end 103a side of the syringe X100, and thereafter the hub 109 is inserted into the hub insertion hole 104b through the inside space 102a.

The seal portion of the hub 109 explained in the above-mentioned embodiment, is a groove, that is, the hub stop groove 110c. However, any form of the seal portion is available as long as the seal portion is annularly formed on the outer peripheral face 110f side of the hub body 190, capable of engaging with the inner face of the hub insertion hole 104b.

Figure 12:
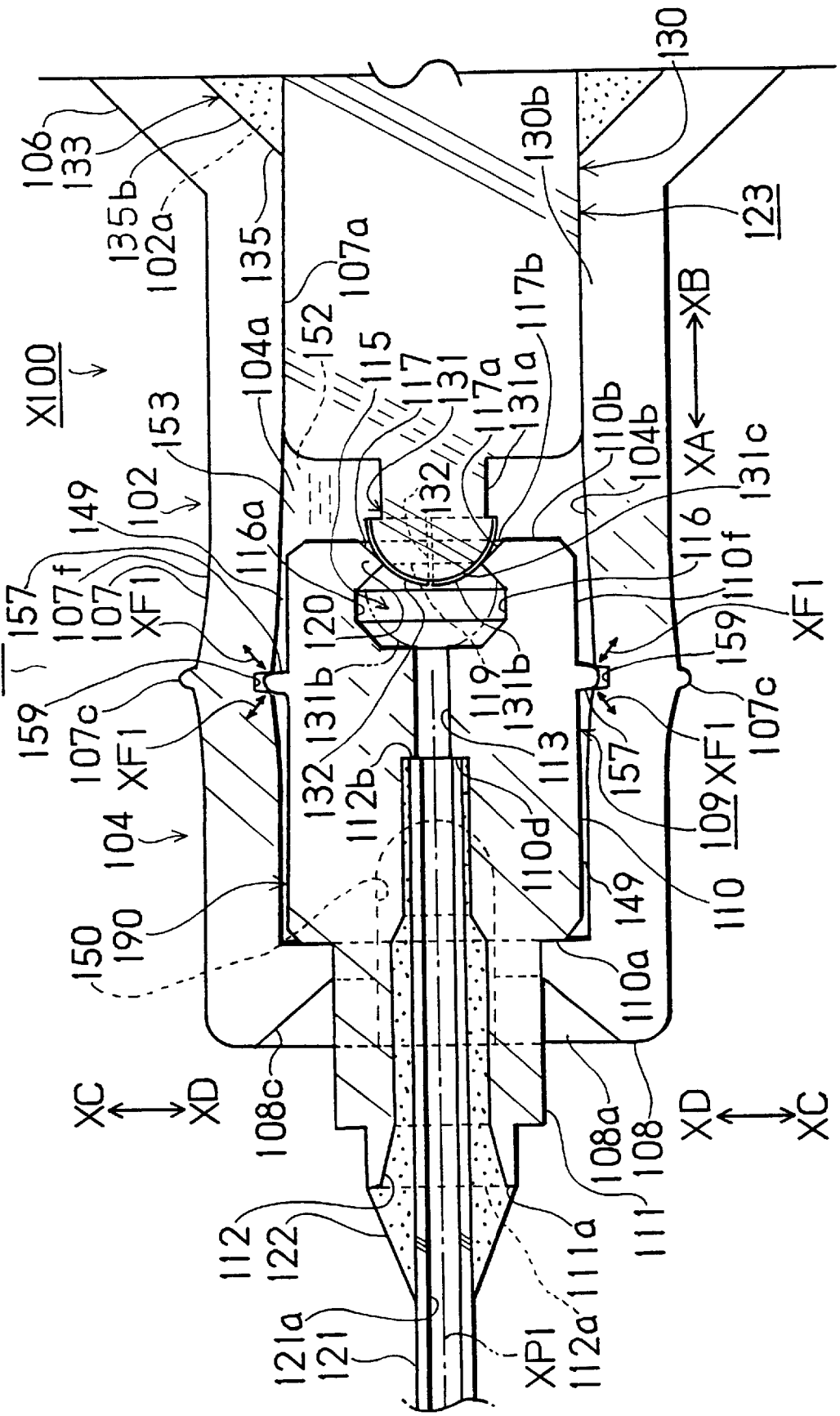
FIG. 12 is a typical sectional view showing an example of the syringe assembly in which a seal rib is formed on the hub side and a seal groove is formed on the hub insertion hole side, of the syringe assembly according to the present invention.
Figure 13:
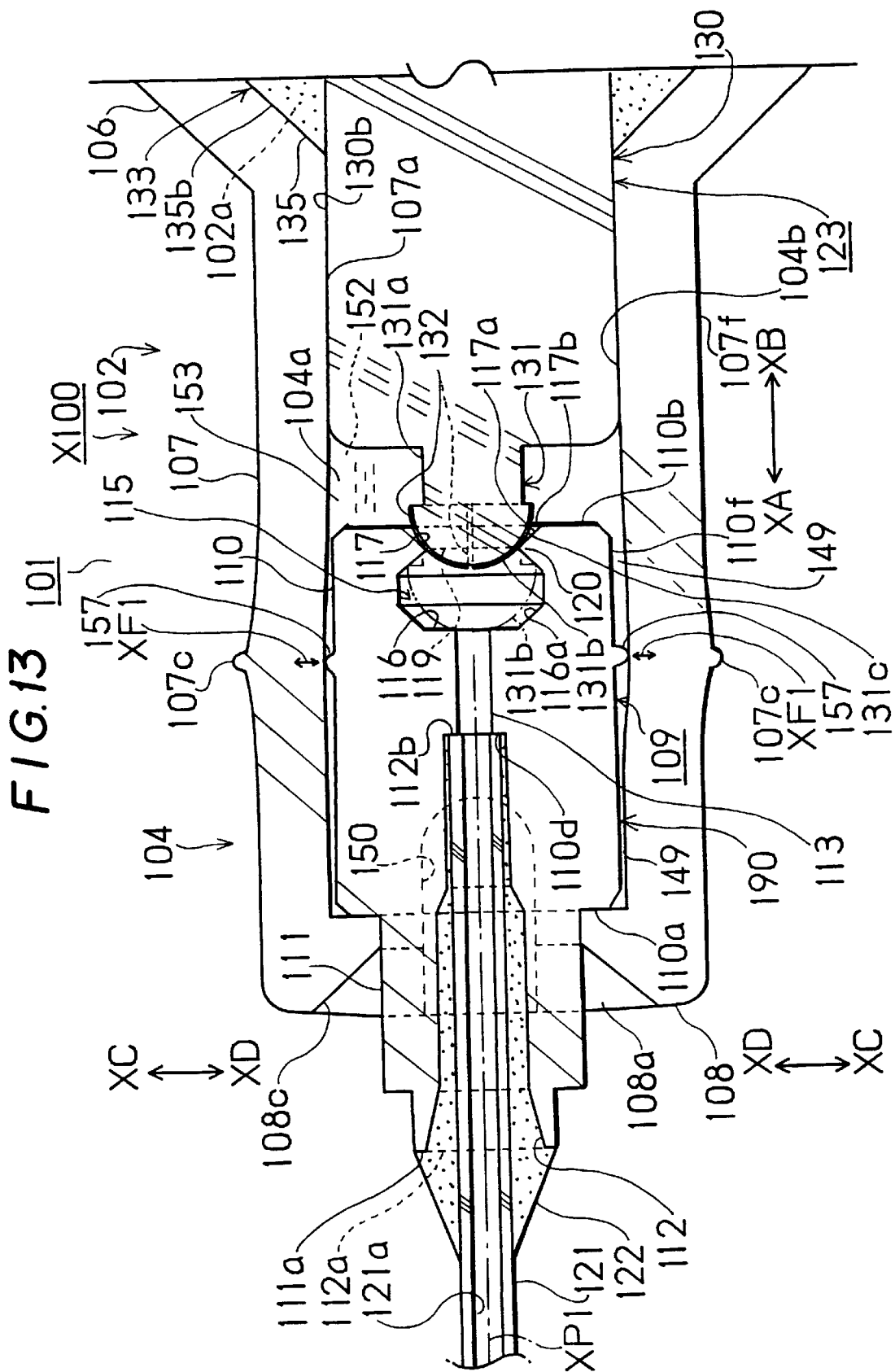
FIG. 13 is a typical sectional view showing an example of the syringe assembly in which the seal rib is formed on the hub side and a hub seal portion of the hub insertion hole side corresponds with the inner peripheral face of the hub insertion hole, of the syringe assembly according to the present invention.

For instance, as shown in FIG. 12 or FIG. 13, the seal portion may be in the shape of a projection, that is, a seal rib 157.

That is, in the embodiment as shown in FIG. 12, the seal rib 157 annularly formed is provided on the outer peripheral face 110f side of the main pillar portion 110 of the hub 109 in place of the hub stop groove 110c in the above-mentioned embodiment. In the syringe X100 used with the hub 109 provided the seal rib 157 therewith, the hub seal portion of the inner face side of the hub insertion hole 104b is provided as an annular seal groove 159 capable of engaging with the seal rib 157, in place of the hub stop rib 107d in the above-mentioned embodiment.

In the embodiment as shown in FIG. 13, the seal rib 157 annularly formed is provided on the outer peripheral face 110f side of the main pillar portion 110 of the hub 109 in place of the hub stop groove 110c in the above-mentioned embodiment. In the syringe X100 used with the hub 109 provided the seal rib 157 therewith, the hub seal portion of the inner face side of the hub insertion hole 104b is formed on the same plane as the inner peripheral face 107a. That is, the seal rib 157 engages with the inner peripheral face 107a which is the hub seal portion of the inner face side of the hub insertion hole 104b, so as to generate a frictional force in the directions as shown by the arrows XA and XB in the figure by pressing the inner peripheral face 107a in the directions as shown by the arrow XC in the figure.

Figure 14:
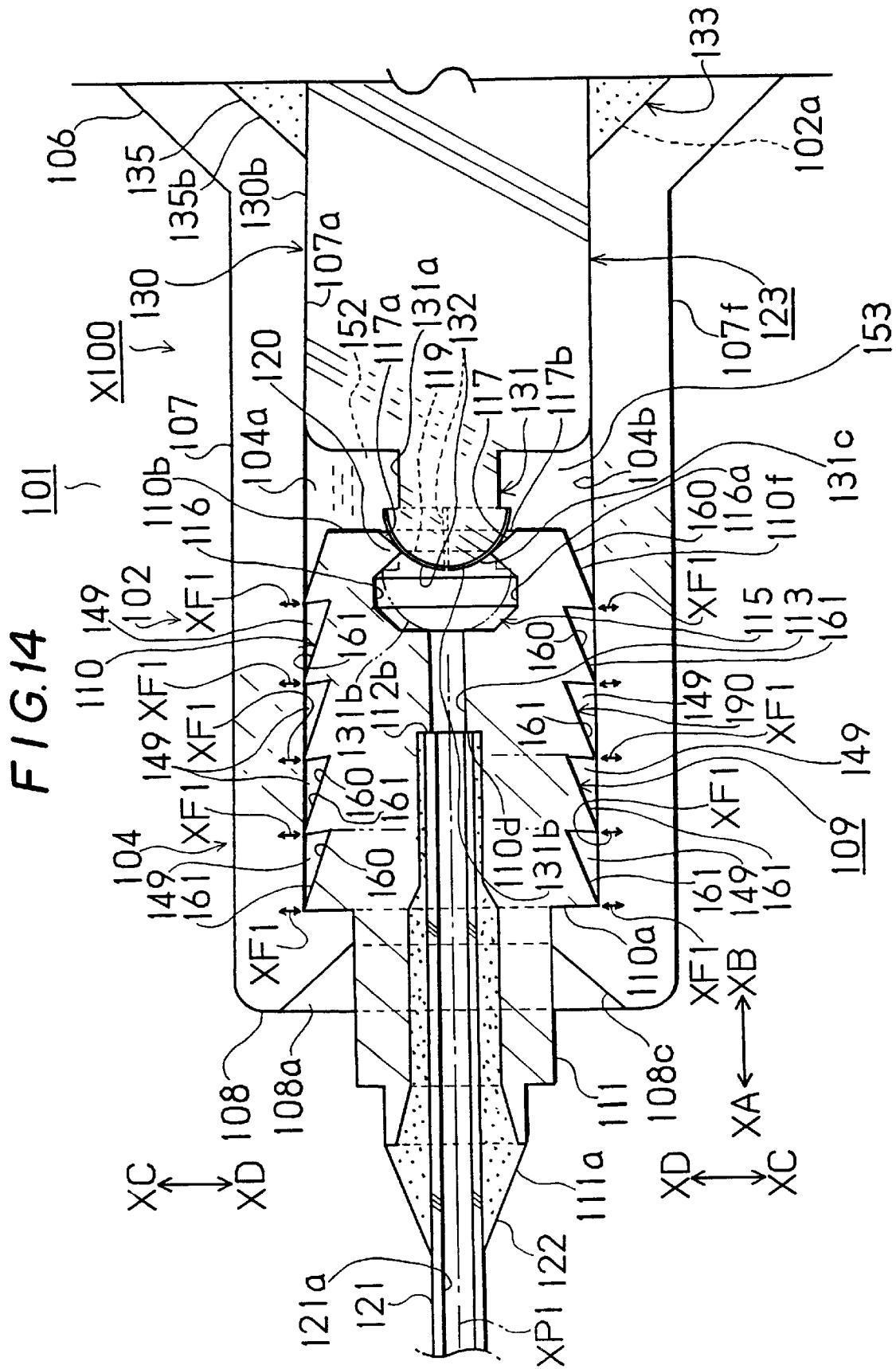
FIG. 14 is a typical sectional view showing an example of the syringe assembly in which fold portions are formed on the hub side and the hub seal portion of the hub insertion hole side corresponds with the inner peripheral face of the hub insertion hole, of the syringe assembly according to the present invention.

The seal portion of the hub 109 explained in the above-mentioned embodiment can be formed in the shape of a projection, that is, a fold portion 161, as shown in FIG. 14.

That is, in the embodiment as shown in FIG. 14, the main pillar portion 110 of the hub 109 is imaginarily comprised by a plurality of main pillar portion pieces 160 (The number is 5 in FIG. 14) in the shape of a taper which outside diameter is more reduced for the direction as shown by the arrow XB of the direction of the axis center XP1 of the main pillar portion 110, and a plurality of main pillar portion pieces 160 are formed unitedly arranging in a line in the directions as shown by the arrows XA and XB. That is, a plurality of fold portions 161 in the shape of a projection, formed by a plurality of the main pillar portion pieces 160, are annularly provided on the outer peripheral face 110f side of the main pillar portion 110 of the hub 109.

Therefore, the main pillar portion 110 of the hub 109 is inserted into the hub insertion hole 104b, thereby a plurality of the fold portions 161 of the main cylindrical portion 110 engages and contacts with the inner peripheral face 107a of the hub insertion hole 104b with a predetermined seal pressure XF1.

The main pillar portion 110 is inserted into the hub insertion hole 104b in the direction as shown by the arrow XB from the hole 108a of the end wall 108. In case of insertion, since the fold portion 161 is taperingly formed in the direction as shown by the arrow XB, the hub 109 can be smoothly inserted into the hub insertion hole 104b for its constitution. Since the main pillar portion 110 is easily inserted into the hub insertion hole 104b by the fold portions 161 in the shape of a taper, it is also applied to the syringe body 102 having no slit 150 in the hub insertion hole 104b, as well as the syringe body 102 having the slits 150 in the hub insertion hole 104b.

Figure 15:
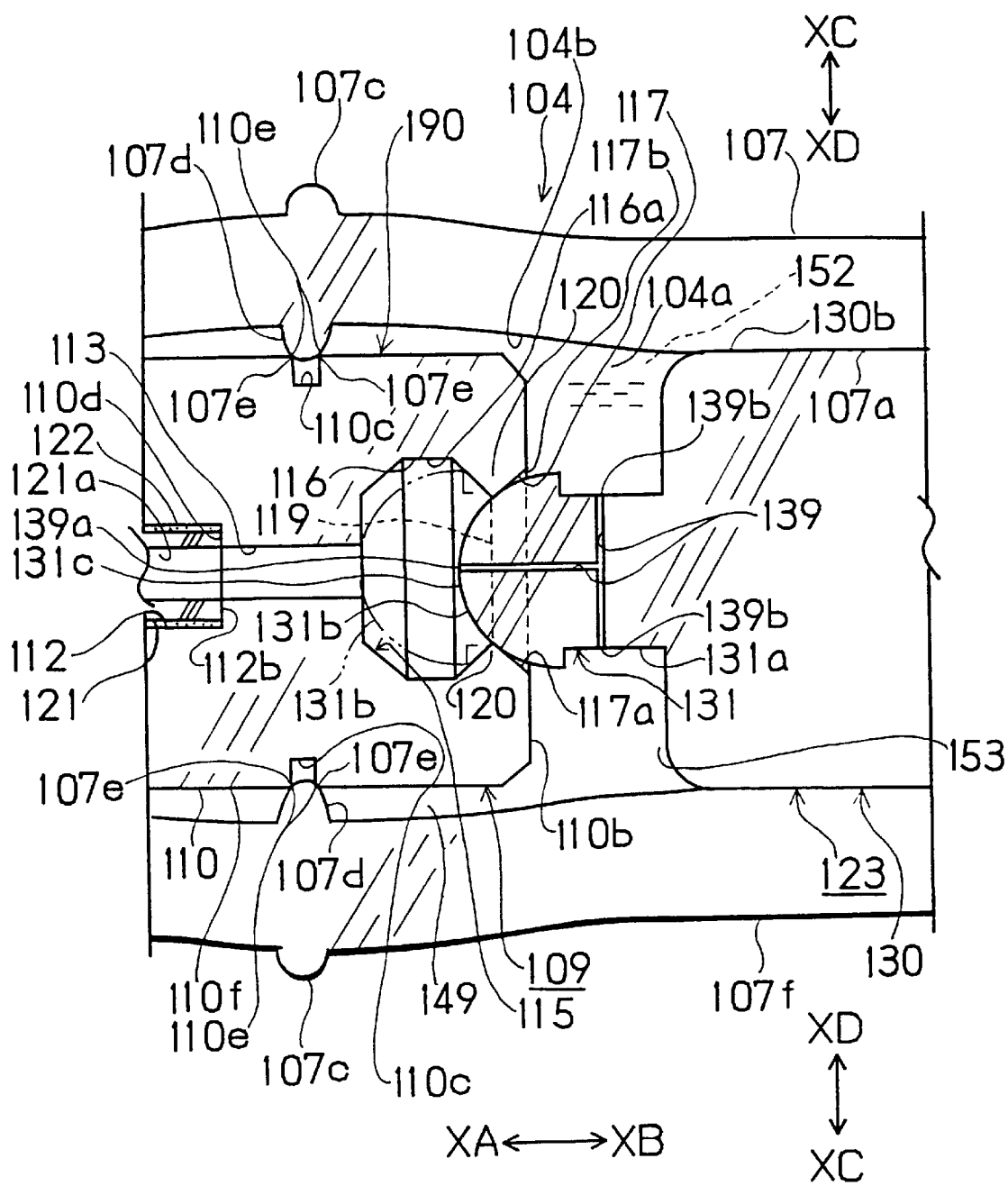
FIG. 15 is a typical sectional view showing an example of the syringe assembly in which a first bypass means is a bypass hole, of the syringe assembly according to the present invention.

In the above-mentioned embodiment, the first bypass means of the hub engagement portion 131 is provided as the groove 132 provided with the insertion portion 131b. However, any form of the first bypass means is available as long as the first bypass means is provided such that the piston engagement hole 115 of the hub 109 and the medium holding space 153 of the inside of the syringe X100 communicate with each other when the hub engagement portion 131 is abutted on the hub 109. For instance, as shown in FIG. 15, an opening 139a is formed at the top of the insertion portion 131b facing the piston engagement hole 115 of the hub engagement portion 131 (that is, the end portion of the arrow XA side), and the other plurality of openings 139b are formed on the outer peripheral face side of the pillar portion 131a of the hub engagement portion 131, and a bypass hole 139 is formed extending the insertion portion 131b and the pillar portion 131a communicating the opening 139a of the insertion portion 131b side and the opening 139b of the pillar portion 131a side with each other, and then this bypass hole 139 may be the first bypass means.

In the above-mentioned embodiment, even when the hub engagement portion 131 is abutted on the hub 109, the first bypass means is provided with the hub engagement portion 131 in order to communicate the piston engagement hole 131 and the medium holding space 153 of the syringe X100 with each other. However, in place of the first bypass means, the second bypass means, communicating a communicating space communicating with the medium flow hole 121a of the needle 121, such as the flow hole 113 of the hub 109 and the medium holding space 153 of the inside of the syringe X100 with each other, that is, communicating the piston engagement hole 115 and the medium holding space 153 with each other, can be formed on the hub 109 side.

Figure 16:
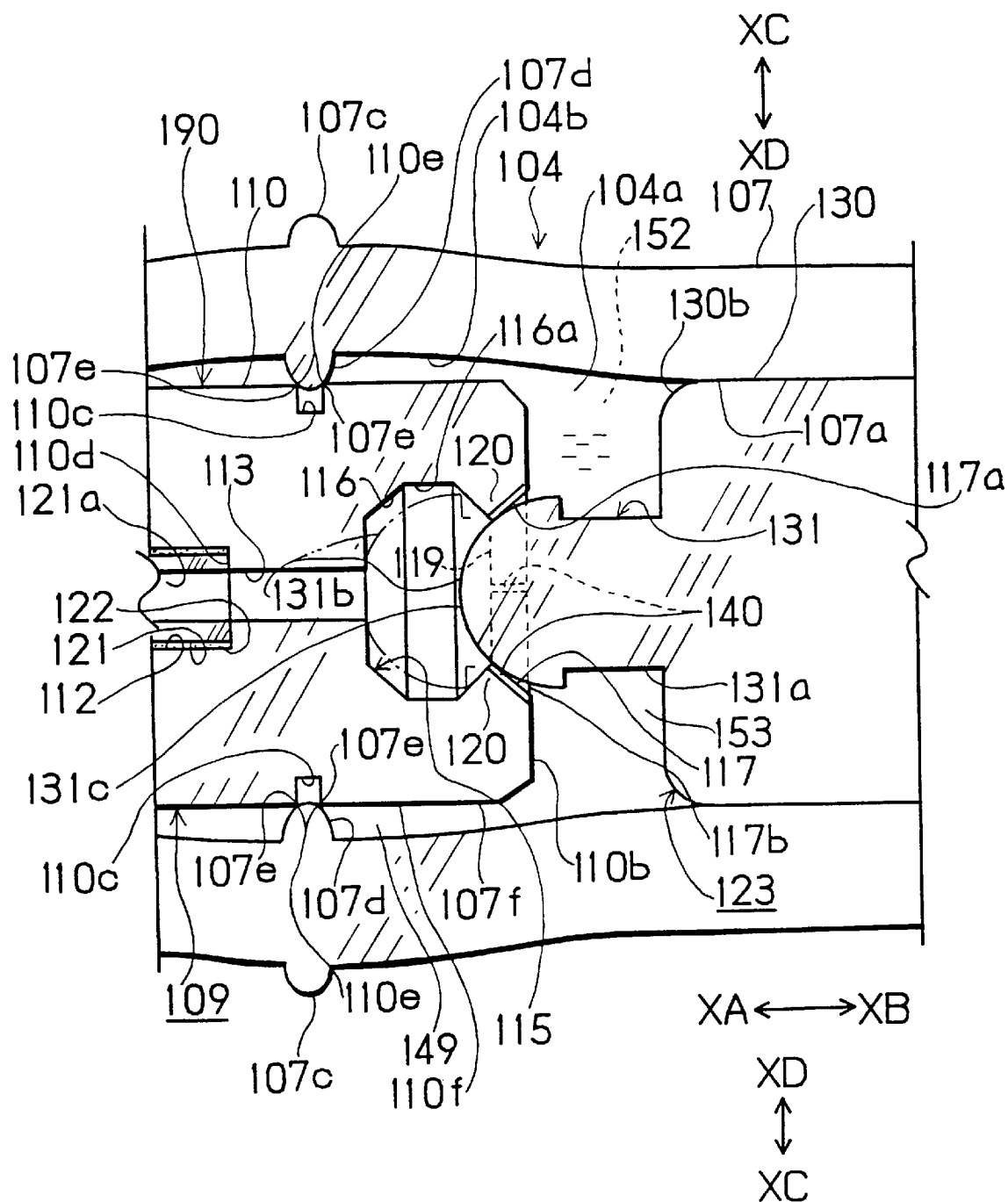
FIG. 16 is a typical sectional view showing an example of the syringe assembly in which a second bypass means is a hub bypass groove, of the syringe assembly according to the present invention.

For instance, as shown in FIG. 16, the second bypass means may be formed as a plurality of hub bypass grooves 140 formed along the wall face 117a facing the introducing hole 117 of the piston engagement hole 115, communicating the engagement holding portion 116 and the opening 117b of the introducing hole 117. In case where the hub bypass grooves 140 are formed at the wall face 117a, the piston engagement hole 115 and the medium holding space 153 of the syringe X100 communicate with each other through the hub bypass grooves 140 also when the hub engagement portion 131 and the hub 109 are abutted on each other.

Figure 17:
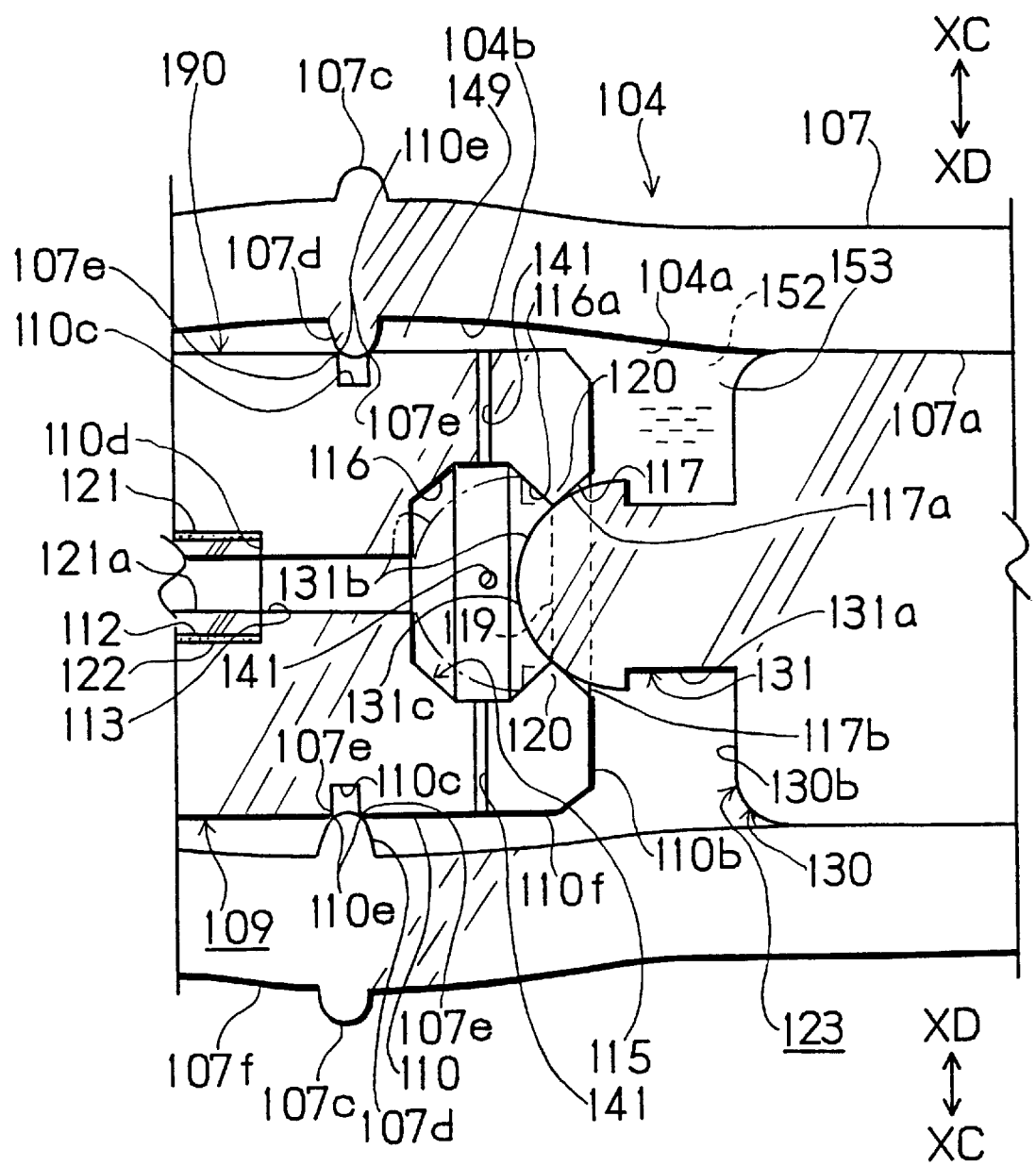
FIG. 17 is a typical sectional view showing an example of the syringe assembly in which the second bypass means is the hub bypass hole, of the syringe assembly according to the present invention.

As shown in FIG.17, the second bypass means formed in place of the first bypass means may be a hub bypass hole 141 which is a hole provided penetrating the hub body 190 between the wall face 116a of the engagement holding portion 116 and the outer peripheral face 110f of the hub 109.

The hub bypass hole 141 may be a hole provided penetrating the hub body 109 between the flow hole 113 and the outside of the hub 109.

Another embodiment of the present invention will now be described hereinafter.

Figure 18:
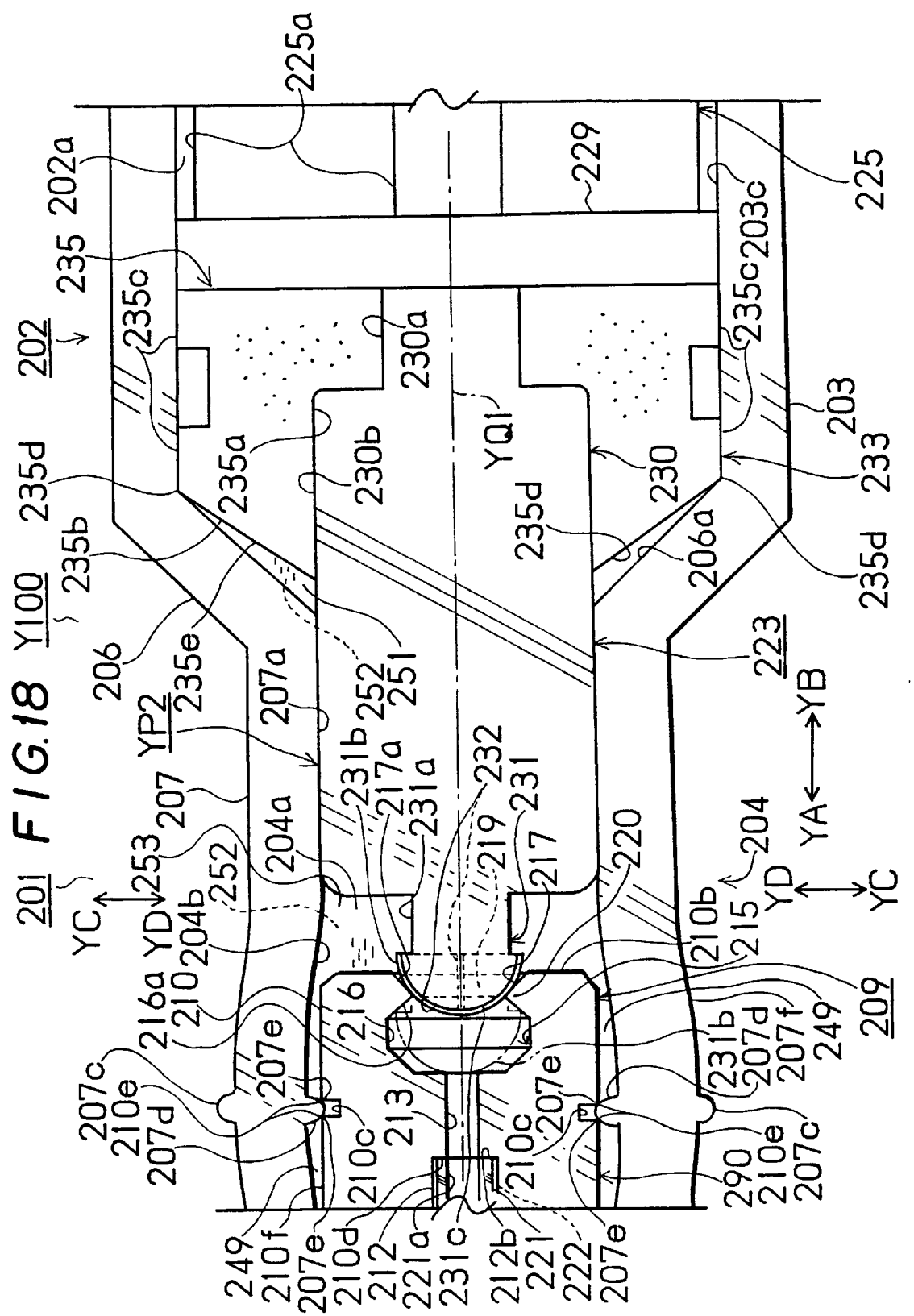
FIG. 18 is a sectional view showing the hub and the portion near the top of the piston, of an example of the syringe assembly according to the present invention.
Figure 19:
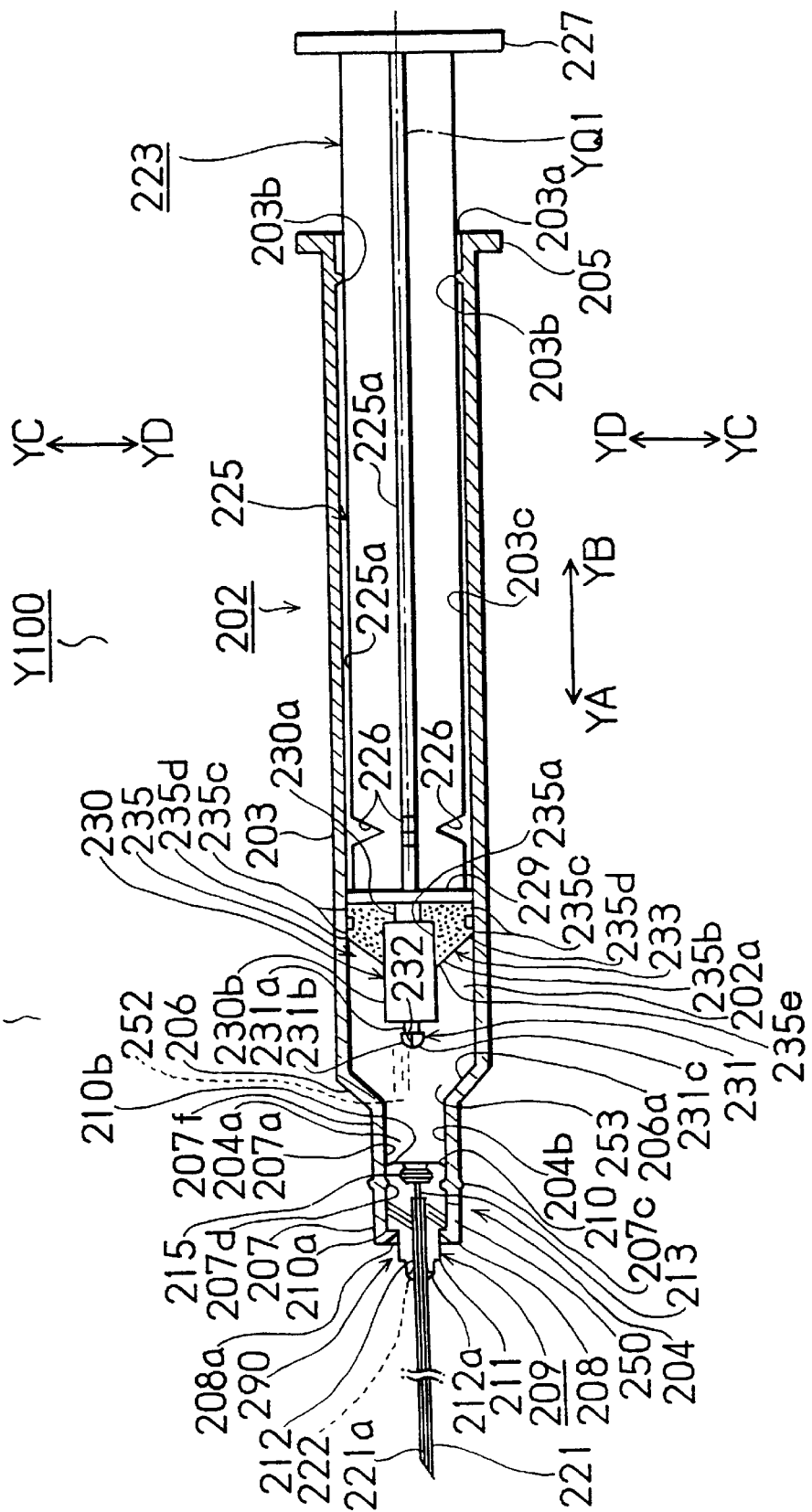
FIG. 19 is a typical sectional view showing the whole syringe assembly as shown in FIG. 18.

A syringe assembly 201 according to the present invention has a syringe Y100 made of resin, as shown in FIG. 19. A syringe body 202 is provided with the syringe Y100 (FIG. 19 is a typical cross section of the syringe assembly 201, but its side is shown in a part of a piston 223, described hereinafter, not the section, for convenience.). A main cylindrical portion 203, cylindrically formed, is provided with the syringe body 202. A direction of an axis center of the main cylindrical portion 203, that is, the reciprocating directions parallel to an axis center YQ1 are an arrow YA direction in the figure (or the left direction of the paper of FIG. 18.) and an arrow YB direction (or the right direction of the paper of FIG. 18).

On the outer periphery side of the main cylindrical portion 203, a syringe support 205 is provided near an opening end 203a of the arrow YB side of the main cylindrical portion 203 (the right side of the paper of FIG. 18), in such a manner as forming a flange of the main cylindrical portion 203. On an inner peripheral face 203c side of the main cylindrical portion 203, an engagement rib 203b, projecting in the direction for the axis center YQ1 of the main cylindrical portion 203, that is, the direction as shown by the arrow YD in the figure, is annularly formed near the opening end 203a along the inner peripheral face 203c.

On the arrow YA side of the main cylindrical portion 203 (the left side of the paper of FIG. 19) a taper 206 in the shape of a funnel, which inside diameter is reduced at a predetermined rate of K1 for the direction as shown by the arrow YA, is formed unitedly connecting with the main cylindrical portion 203.

The inside of the main cylindrical portion 203 and the inside of the taper 206 communicate with each other in the directions as shown by the arrows YA and YB, and the space combining both insides is an inside space 202a of the syringe body 202.

On the side of the arrow YA of the taper 206, that is, on the side of the top of the syringe body 202, as shown in FIG. 18 or FIG. 19, a hub insertion portion 204 is formed unitedly connecting with the taper 206, and the hub insertion portion 204 has a small cylindrical portion 207. The small cylindrical portion 237 is formed unitedly connecting with the taper 206, and coaxial with the main cylindrical portion 203, and the inside diameter of the small cylindrical portion 207 is smaller than one of the main cylindrical portion 203.

An inner peripheral face 207a side of the small cylindrical portion 207 is a hub insertion hole 204b. A hub stop rib 207d projecting for the axis center YQ1 is formed in the hub insertion hole 204b. The hub stop rib 207d is annularly formed along the inner peripheral face 207a of the small cylindrical portion 207. The section of a plane including the axis center YQ1 of the hub stop rib 207d (that is, the section as shown in FIG. 18) is a circular arc.

On the other hand, on an outer peripheral face 207f side of the small cylindrical portion 207, a stiffening rib 207c is annularly provided at the position corresponding to the hub stop rib 207d putting the small cylindrical portion 207 therebetween.

Figure 20:
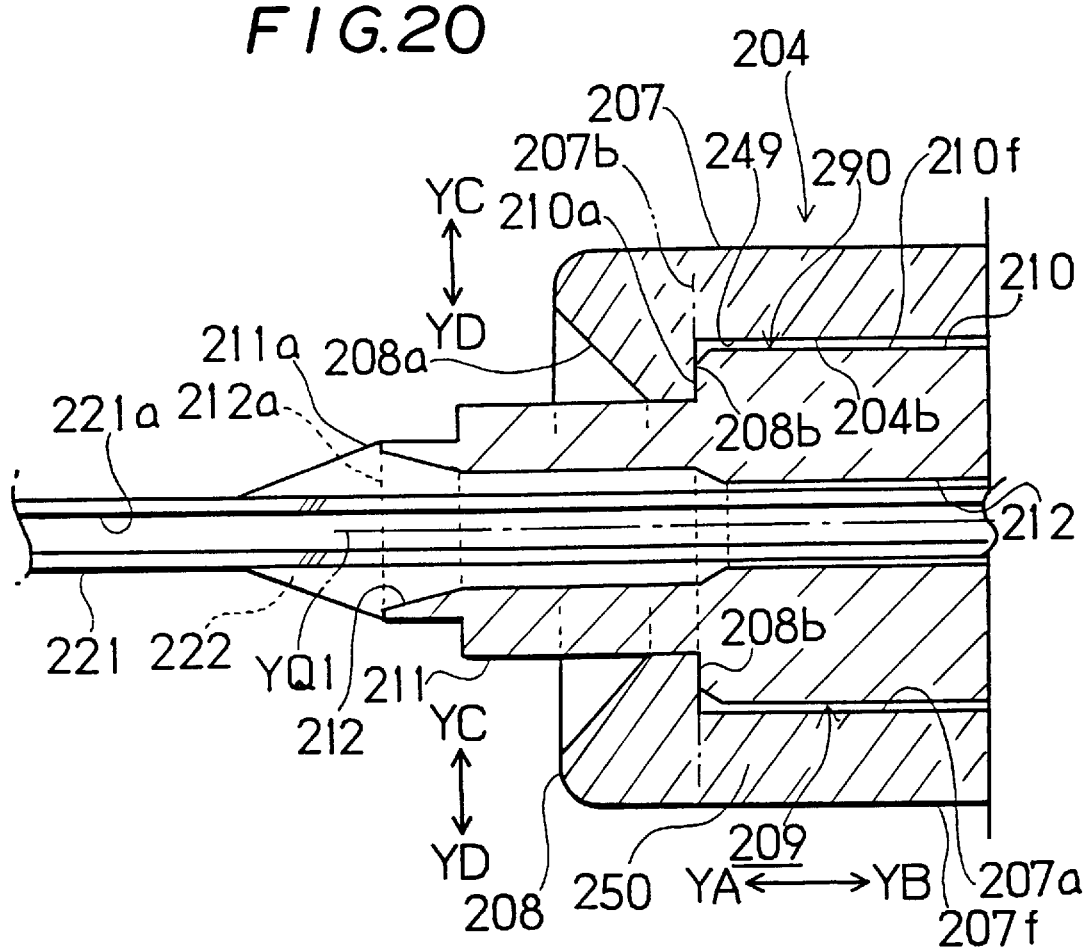
FIG. 20 is a view showing a portion near a hub insertion portion of the syringe assembly as shown in FIG. 19.
Figure 21:
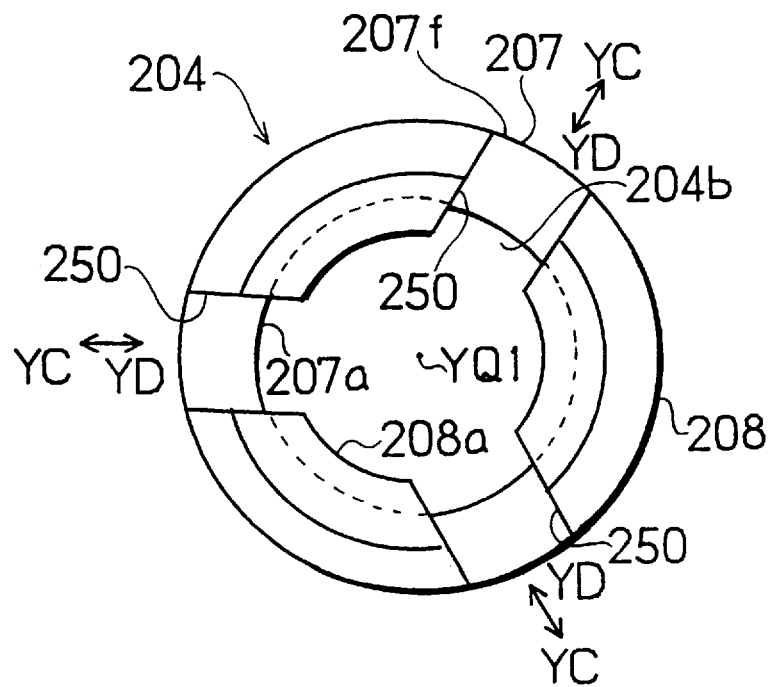
FIG. 21 is a view showing the hub insertion portion of the syringe assembly as shown in FIG. 19 seen from the arrow YB direction.

As shown in FIG. 19 through FIG. 21, an end wall 208 formed in the shape of a circular plate, which outside diameter is equal to one of the small cylindrical portion 207, is provided with the small cylindrical portion 207. The end wall 208 is provided united with the small cylindrical portion 207 contacting a wall face 208b of the arrow YB side of the end wall 208 and an end portion 207b of the arrow YA side of the small cylindrical portion 207 with each other. A hole 208a having a circular section, penetrating both front and back wall faces of the end wall 208 in the directions as shown by the arrows YA and YB, is provided with the end wall 208, with the axis center YQ1 as its center. The arrow A side of the hole 208a is taperingly formed enlarging the sectional inside diameter in the direction as shown by the arrow YA.

As shown in FIG. 20 or FIG. 21, three slits 250 are formed extending on the end wall 208 and the small cylindrical portion 207. The slits 250 are formed extending in the end wall 208 in a radial direction with respect to the axis center YQ1, that is, in the directions as shown by the arrows YC and YD in the figure (The arrow YC direction is opposite to the arrow YD direction), communicating with the hole 208a provided in the end wall 208, and parallel to the directions as shown by the arrows YA and YB in the small cylindrical portion 207. The slits 250 are formed at the positions on the arrow YA side rather than the hub stop rib 207d and the stiffening rib 207c, and not reaching the hub stop rib 207d and the stiffening rib 207c.

Since the arrow YA side of the hub insertion portion 204 is divided into three parts by the slits 250, the portions of the hub insertion portion 204 formed the slits 250 are easy to be elastically enlarged in the direction as shown by the arrow YC. That is, when the syringe assembly 201 is assembled by inserting a hub 209 described hereinafter into the syringe Y100, the portions of the hub insertion portion 204 formed the slits 250 are elastically enlarged in the direction as shown by the arrow YC and the hole 208a of the end wall 208 is enlarged, thereby the hub 209 referred hereinafter can be inserted into the hub insertion hole 204b through the hole 208a The hub insertion portion 204 is comprised as explained heretofore. The syringe Y100 is comprised of the syringe support 205, the main cylindrical portion 203 comprising the syringe body 202, the taper 206, and the hub insertion portion 204 in such a manner that these are united.

The hub 209 made of resin, which is harder than the syringe Y100, is provided with the hub insertion hole 204b of the hub insertion portion 204. As shown in FIG. 18 through FIG. 20, the hub 209 has a hub body 290. A main pillar portion 210, which longitudinal direction is parallel to the directions as shown by the arrows YA and YB, which axis center is the axis center YQ1, is provided in the shape of a cylinder with the hub body 290.

A hub stop groove 210c is formed on the side of an outer peripheral face 210f of the main pillar portion 210. The hub stop groove 210c is annularly formed along the outer peripheral side of the main pillar portion 210.

On an end face 210a side of the arrow YA side of the main pillar portion 210, a small pillar portion 211 is provided extending in the directions as shown by the arrows YA and YB directions, coaxial with and united with the main pillar portion 210. The hub 209 is provided such that the main pillar portion 210 of the hub 209 is inserted into the hub insertion hole 204b of the hub insertion portion 204, and the small pillar portion 211 of the hub 209 is inserted into the hole 208a of the end wall 208 so as to penetrate. The hub stop rib 207d of the hub insertion portion 204 and the hub stop groove 210c of the hub 209 are at the positions corresponding to and adjusting to each other, and then the hub stop rib 207d is engaged with the hub stop groove 210c inserting the top end side on the arrow YD side thereof into the hub stop groove 210c which is at the position corresponding and adjusting to one of the hub stop rib 207d.

Since the width of the hub stop rib 207d in the directions as shown by the arrows YA and YB is broader than one of the hub stop groove 210c in the directions as shown by the arrows YA and YB, the hub stop rib 207d is engaged with the hub stop groove 210c abutting on opening ends 210e, 210e of both sides of the arrows YA and YB of the hub stop groove 210c in seal portions 207e, 207e on the sides of the arrows YA and YB of the top thereof.

The inner peripheral face 207a of the small cylindrical portion 207 is not in contact with the outer peripheral face 210f of the hub 209 in the portions excluding the hub stop rib 207d, and a gap space 249 is formed bewteen the inner peripheral face 207a and the outer peripheral face 210f. That is, since contact between the inner peripheral face 207a side of the hub insertion portion 204b and the hub 209 is executed only between the hub stop rib 207d and the outer peripheral face 210f side of the hub 209, when the syringe assembly 201 is assembled by inserting the hub 209 into the syringe Y100, the hub 209 can be easily inserted into the hub insertion portion 204. In addition, in case of the operation of storing a needle, described hereinafter, the hub 209 is easily pulled out of the hub insertion portion 204 (As long as insertion of the hub 209 into the hub insertion portion 204 and pulling of the hub 209 out of the hub insertion portion 204 can be easily executed, the portions excluding the hub stop rib 207d of the inner peripheral face 207a of the small cylindrical portion 207 may be in contact with the outer peripheral face 210f of the hub 209.).

An end face 210b of the arrow YB side of the main pillar portion 210 of the hub 209 is positioned on the arrow YA side rather than the boundary between the hub insertion hole 204b and the inside space 202a (that is, the boundary between the inside of the small cylindrical portion 207 and the inside of the taper 206), and the space of the inside of the hub insertion hole 204b on the arrow YB side rather than the end face 210b is a hole space 204a.

On the other hand, the hub insertion portion 204 is elastically deformed expanding the small cylindrical portion 207 in the direction as shown by the arrow YC in such a state that the hub 209 is provided with the hub insertion hole 204b. That is, the restoring force by elastic deformation of the small cylindrical portion 207 is transferred to the hub 209 through the hub stop rib 207d of the small cylindrical portion 207. That is, predetermined seal pressures by the restoring force respectively act between the hub stop rib 207d and the hub 209 in the portions between the seal portion 207e and the opening end 210e of the hub stop groove 210c in which both abut on each other, and then, the portion between the seal portion 207e and the opening end 210e is in a water tight state or an air tight state.

The rigidity of the hub stop rib 207d and the portion near thereof is increased in the small cylindrical portion 207 by the stiffening rib 207c which is at the position corresponding to the hub stop rib 207d putting the small cylindrical portion 207 therebetween, and then a predetermined restoring force by elastic deformation of the small cylindrical portion 207 can be effectively obtained.

As shown in FIG. 18 through FIG. 20, a needle insertion hole 212 is provided with the hub 209. The needle insertion hole 212 is provided forming a circular opening 212a, which center is the axis ceter YQ1, at an end face 211a of the arrow YA side of the small pillar portion 211 of the hub 209, extending from the end face 211a in the direction as shown by the arrow YB. An end portion 212b of the arrow YB side of the needle insertion hole 212 reaches the inside of the main pillar portion 210 and the end portion 212b is in contact with a wall face 210d of the main pillar portion 210. In the needle insertion hole 212, tapers are adequately formed such that the diameter of the needle insertion hole 212 is made narrower for the direction as shown by the arrow YB.

On the other hand, a flow hole 213 is provided with the main pillar portion 210 of the hub 209 adjacent to the arrow YB side of the needle insertion hole 212 (right side of the paper of FIG. 18). The flow hole 213 is cylindrically formed such that its center is the axis center YQ1 and its diameter is smaller than one of the end portion 212b of the needle insertion hole 212. The flow hole 213 is provided forming a circular opening at the wall face 210d of the main pillar portion 210, communicating with the needle insertion hole 212.

A piston engagement hole 215, which section perpendicular to the axis center YQ1 is a circle, is provided with the main pillar portion 210 of the hub 209 communicating with and adjacent to the arrow YB side of the flow hole 213, coaxial with the axis center YQ1. The arrow YB side of the piston engagement hole 215 is open outside in the end face 210b of the main pillar portion 210.

The piston engagement hole 215 is comprised of two parts, an engagement holding portion 216 of the arrow YA side and an introducing portion 217 of the arrow YB side. The engagement holding portion 216 is almost cylindrical shape, coaxial with the axis center YQ1, and both end portion sides of the arrows YA and YB thereof are tareringly formed such that each diameter is made narrower for the direction as shown by the arrow YA or arrow YB. The end portion side of the arrow YA side of the engagement holding portion 216 is communicated and connected with the flow hole 213.

The introducing portion 217 communicates with and is adjacent to the end portion of the arrow YB side of the engagement holding portion 216. The diameter of the introducing portion 217 is made bigger for the direction as shown by the arrow YB. Then, the portion sandwitched between a wall face 216a facing the engagement holding portion 216 and a wall face 217a facing the introducing portion 217 of the main pillar portion 210 forms a projection 220 projecting for the axis center YQ1 with a boundary portion 219 between the engagement holding portion 216 and the introducing portion 217 as an apex.

On the other hand, as shown in FIG. 19 or FIG. 20, a needle 221 is inserted into the needle insertion hole 212 of the hub 209. The needle 221 is inserted into the needle insertion hole 212 from the rear end portion thereof and the top end side is positioned outside of the syringe body 202. The rear end of the needle 221 abuts on the wall face 210d formed on the arrow YB side of the needle insertion hole 212. A medium flow hole 221a provided penetrating from the top end to the rear end side of the needle 221 and the flow hole 213 are adjacent to and communicate with each other in the directions as shown by the arrows YA and YB.

An adhesive 222 is injected into the needle insertion hole 212 filling between the needle 221 and the hub 209 and is hardened.

The piston 223 is provided with the syringe assembly 201, as shown in FIG. 18 or FIG. 19 (FIG. 19 is a typical sectional view of the syringe assembly 201, but with respect to a piston body 225, an outer press plate 227, an inner press plate 229, a packing support 230, a hub engagement portion 231, referred hereinafter, of the piston 223, their sides are shown, not their sections, for convenience.)

The piston 223 has the bar-shaped piston body 225 extending in the directions as shown by the arrows YA and YB. The piston body 225 is comprised such that two congruent plate portions 225a, each which is a plate shaped rectangle especially long in the directions as shown by the arrows YA and YB, are unitedly cross provided with each other such that the sections thereof form the shape of a cross. The width perpendicular to the directions as shown by the arrows YA and YB of the plate face of the plate portion 225a is almost equal to the inside diameter in the engagement rib 203b of the main cylindrical portion 203, and the piston body 225 is inserted into the main cylindrical portion 203 through the opening end 203a from the arrow YA side of the piston body 225.

On each plate portion 225a of the piston body 225, notches 226 are formed from both side portions of the respective plate portions 225a, 225a in the direction of the axis center (that is, the axis center YQ1) of the piston body 225 in the shape of a wedge near the direction by the arrow YA. Four notches 226 are provided at the positions adjusted one another in the directions as shown by the arrows YA and YB.

The outer press plate 227 in the shape of a circular plate, which plate face is perpendicular to the directions as shown by the arrows YA and YB, is provided united with the piston body 225 on the end portion side of the arrow YB side of the piston body 225.

The inner press plate 229 in the shape of a circular plate, which plate face is perpendicular to the directions as shown by the arrows YA and YB, is provided united and coaxial with the piston body 225 on the end portion side of the arrow YA side of the piston body 225 (Therefore, the inner press plate 229 is positioned inside of the main cylindrical portion 203.), and the diameter of the inner press plate 229 is almost equal to the inside diameter of the main cylindrical portion 203 (Therefore, the diameter of the inner press plate 229 is bigger than the inside diameter in the engagement rib 203b of the main cylindrical portion 203.).

As shown in FIG. 19, the packing support 230 is provided with the inner press plate 229 on the arrow YA side thereof. A pillar portion 230a in the shape of a cylinder, extending in the directions as shown by the arrows YA and YB, is provided with the packing support 230, being coaxial with the inner press plate 229. The diameter of the pillar portion 230a is smaller than one of the inner press plate 229. The pillar portion 230a is provided on the arrow YA side of the inner press plate 229, being united with the inner press plate 229. As shown in FIG. 18 or FIG. 19, an insertion pillar portion 230b in the shape of a cylinder, extending in the directions as shown by the arrows YA and YB being coaxial with the pillar portion 230a, having an outside diameter almost equal to the inside diameter of the small cylindrical portion 207, is provided on the arrow YA side of the pillar portion 230a, being united with the pillar portion 230a.

The hub engagement portion 231 is provided on the arrow YA side of the insertion pillar portion 230b. A pillar portion 231a in the shape of a cylinder, extending in the directions as shown by the arrows YA and YB, is provided with the hub engagement portion 231, being coaxial with the insertion pillar portion 230b. The diameter of the pillar portion 231a is smaller than one of the insertion pillar portion 230b. The pillar portion 231a is provided on the arrow YA side of the insertion pillar portion 230b, being united with the insertion pillar portion 230b. An insertion portion 231b in the shape of a hemi-sphere, which diameter is bigger than one of the pillar portion 231a, is provided on the arrow YA side of the pillar portion 231a, being united with the pillar portion 231a facing a spherical face 231c side to the arrow YA side. A plurality of grooves 232 in the shape of a stripe are provided with the insertion portion 231b, being parallel to the spherical face 231c, extending from the top portion of the arrow YA side to the arrow YB side.

The diameter of the pillar portion 231a is almost equal to the inside diameter in the boundary portion 219 of the piston engagement hole 215 provided with the hub 209. Therefore, the diameter of the insertion portion 231b is bigger than one of the boundary portion 219. The size of the insertion portion 231b allows itself to be sufficiently inserted into and to be held by the engagement holding portion 216 of the piston engagement hole 215.

On the other hand, as shown in FIG. 18, a packing 233 made of flexible resin, is supported with the packing support 230. The packing 233 has a packing body 235 which is inserted inside of the main cylindrical portion 203 of the syringe Y100 so as to adjust. An engagement hole 235a penetrating the packing body 235 in the directions as shown by the arrows YA and YB is provided with the packing body 235. The pillar portion 230a of the packing support 230 and a part of the insertion pillar portion 230b penetrating the engagement hole 235a. That is, the packing 233 engages with the packing support 230 such that the packing support 230 penetrates the engagement hole 235a, thereby the packing 233 is supported by the packing support 230. The end portion of the arrow YB side of the packing body 235 abuts on the inner press plate 229 so as to easily receive a force in the direction as shown by the arrow YA by the inner press plate 229.

The arrow YA side of the packing body 235 is a taper 235b. While the form of the inside of the taper 206 of the syringe body 202 is a taper, reducing the inside diameter at a predetermined rate K1 for the direction as shown by the arrow YA, as described before, the form of the taper 235b in a natural state is a taper, reducing the outside diameter at a predetermined rate K2, which is bigger than a predetermined rate K1. That is, the taper 235b is formed forming a remaining space 251 between a surface 235e excluding the end portion 235d of the taper 235b and the inner peripheral face 206a of the taper 206 when an end portion 235d of the arrow YB side of the taper 235b in a natural state abuts on an inner peripheral face 206a of the taper 206 inside of the taper 206.

A part of the arrow YA side of the insertion pillar portion 230b of the packing support 230 penetrating the engagement hole 235a further projects on the arrow YA side rather than the taper 235b.

In such a state that the end portion 235d of the taper 235b is abutted on the inside of the taper 206 of the syringe body 202 when the taper 235b of the packing 233 is in a natural state, as shown in FIG. 18, the insertion pillar portion 230b of the packing support 230 enagaging with the packing 233 is inserted into the hub insertion hole 204b of the syringe body 202. The form of the packing 233 is set so as to make such a state where the spherical face 231c of the insertion portion 231b of the hub engagement portion 231 contacts with the wall face 217a facing the introducing portion 217 of the piston engagement hole 215.

The outside diameter of the packing body 235 of the packing 233 is almost equal to one of the inner press plate 229. However, on the outer peripheral side of the packing body 235, annular folds 235c are double formed along the outer periphery of the packing body 235 arranging in a line in the directions as shown by the arrows YA and YB. Therefore, the packing 233 is inserted into the main cylindrical portion 203 of the syringe body 202, reducing the portion near the fold 235c of the packing body 235 in the direction for the axis center YQ1, that is, in the direction as shown by the arrow YD by elastic deformation. That is, the packing 233 and the main cylindrical portion 203 are closely contacted with each other in the folds 235c and the inner peripheral face 203c, and the portion between the packing 233 and the main cylindrical portion 203 is sealed with water seal or air seal.

The inner peripheral face 203c of the main cylindrical portion 203 of the syringe body 202 is smoothly formed. Therefore, the piston 223 inserted the packing 233 therein is free to slide in the inside space 202a of the main cylindrical portion 203 in the directions as shown by the arrows YA and YB.

The syringe assembly 201 is comprised as before, and then the syringe assembly 201 is used and, after that, the syringe assembly 201 is discarded as follows.

At first, the needle 221 of the syringe assembly 201 is advanced into an injection medium 252 in a medicine bottle (not shown), the piston 223 is pulled in the direction as shown by the arrow YB with respect to the syringe body 202, and by differential pressure, the injection medium 252 in the medicine bottle is flowed to a medium holding space 253 on the needle 221 side rather than the piston 223 of the hole space 204a of the hub insertion portion 204 and the inside space 202a of the syringe body 202 passing through the medium flow hole 221a of the needle 221, the flow hole 213 of the hub 209 and the piston engagement hole 215 so as to fill the syringe assembly 201 with the injection medium 252.

In case of filling of the injection medium 252, a differential pressure force in the direction as shown by the arrow YB by differential pressure between the outside and the medium holding space 253 acts on the hub 209. However, the restoring force in the direction as shown by the arrow YD which the hub insertion portion 204 has is set as a predetermined size as described heretofore, thereby sealing between each seal portion 207e and each opening end 210e of the arrow YA side and the arrow YB side is not disengaged between the hub insertion portion 204 and the hub 209 against the maximum differential pressure force predicted.

After filling of the injection medium 252, the needle 221 of the syringe assembly 201 is stuck into an injection portion of a patient.

Subsequently, the outer press plate 227 of the piston 223 is pressed in the direction as shown by the arrow YA so as to drive the piston 223 with respect to the syringe body 202 in the direction as shown by the arrow YA. The injection medium 252 of the medium holding space 253 is pressurized so as to flow into the body in the injection portion of a patient through the piston engagement hole 215 of the hub 209, the flow hole 213, the medium flow hole 221a of the needle 221.

On this occasion, the injection medium 252 is pressurized and an action force by the pressure of the injection medium 252 is added to the hub 209 in the direction as shown by the arrow YA from the end face 210b side of the hub 209 adjacent to the injection medium 252. However, the restoring force in the direction as shown by the arrow YD which the hub insertion portion 204 has is set in such a predetermined size as described heretofore, thereby sealing between each seal portion 207e and each opening end 210e on the arrow YA side and the arrow YB side is not disengaged between the hub insertion portion 204 and the hub 209 against the maximum action force predicted.

After a predetermined amount of the injection medium 252 is flowed into the body in the injection portion of a patient, that is, after the piston 223 is driven to the position where the end portion 235d of the taper 235b of the packing 233 is abutted on the inside of the taper 206 of the syringe body 202, and as shown in FIG. 18, the insertion portion 231b of the hub engagement portion 231 of the piston 223 abuts on the wall face 217a in the introducing hole 217 of the piston engagement hole 215 of the hub 209, that is, to an injection end position YP2 in the figure, the whole syringe assembly 201 is pulled in the direction as shown by the arrow YB to a patient, and the needle 221 is pulled out of the injection portion of a patient.

After the needle 221 is pulled out, the operation of storing the needle is executed as follows.

In the operation of storing the needle, the engagement operation between the piston 223 and the hub 209 is executed as follows.

That is, the outer press plate 227 of the piston 223 is further pressed with fingers in the direction as shown by the arrow YA so as to press the piston body 225 in the direction as shown by the arrow YA, and then the insertion pillar portion 230b of the packing support 230 and the hub engagement portion 231 are fed in the direction as shown by the arrow YA in the hub insertion hole 204b.

Just before start of the operation of storing the needle, the piston 223 is positioned such that the taper 235b in a natural state is positioned corresponding to the inside of the taper 206, the end portion 235d of the arrow YB side of the taper 235b abuts on the inner peripheral face 206a of the taper 206, and the remaining space 251 is formed between the surface 235e excluding the end portion 235d of the taper 235b and the inner peripheral face 206a of the taper 206. Therefore, by pressing pressure in the direction as shown by the arrow YA of the piston body 225, in the packing 233, the portion on the arrow SYB side from the portion near the end portion 235d abutting on the taper 206 is compressed in the directions as shown by the arrows YB and YD, and the other part is pressed out in the direction as shown by the arrow YA making use of the remaining space 251 in such a manner that the surface 235e approaches the taper 206. Therefore, since the quantity of elastic compression in the packing 233 is reduced by the remaining space 251, the piston 223 can be operated with extremely small force.

As shown in FIG. 13, just before start of the operation of storing the needle, the hole space 204a between the end face 210b of the hub 209 and the insertion pillar portion 230b of the piston 223 side (that is, the medium holding space 253) and the remaining space 251 (that is, the medium holding space 253) are filled with the remaining injection medium 252. The operation of storing the needle is started, the piston 223 is pressed and moved in the direction as shown by the arrow YA as described heretofore, thereby the remaining injection medium 252 is pressurized. However, a plurality of grooves 232 are provided with the insertion portion 231b, as described heretofore, and then these grooves 232 are not occupied when the insertion portion 231b and the wall face 217a are abutted on each other by pressing. Therefore, when the insertion portion 231b and the wall face 217a are abutted on each other by pressing, the hole space 204a or the remaining space 251 side and the engagement holding portion 216 side communicate with the grooves 232. The remaining injection medium 252 pressurized of the hole space 204a or the remaining space 251 flows to the engagement holding portion 216 side through these grooves 232 (This is because the injection medium 252 of the remaining space 251 can flow to the hole space 204a side passing between the insertion pillar portion 230b and the small cylindrical portion 207 since the portion between the insertion pillar portion 230b and the small cylindrical portion 207 is not water tight.), and furthermore, is expelled outside through the flow hole 213 and the medium flow hole 221a of the needle 221. That is, when the operation of storing the needle starts and the piston 223 is pressed and moved in the direction as shown by the arrow YA, the remaining injection medium 252 pressurized in the hole space 204a or the remaining space 251 is appropriately expelled outside, and the pressure is not extremely increased. Therefore, the resistance by pressure of remaining injection medium 252 is not extremely acted on the piston 223, and then the piston 223 is pressed and moved in the direction as shown by the arrow YA with extremely small force.

While the packing 233 is elastically reduced, the insertion pillar portion 230b of the packing support 230 and the hub engagement portion 231 are pressed and moved in the direction as shown by the arrow YA in the hub insertion portion 204b, and the insertion portion 231b of the hub engagement portion 231 is pressed and moved in the direction as shown by the arrow YA from the introducing portion 217 of the piston engagement hole 215 for the engagement holding portion 216.

That is, the piston 223 is pressed and moved in the direction as shown by the arrow YA, thereby the insertion portion 231b is pressed to the wall face 217a in the introducing portion 217. However, the arrow YA side of the insertion portion 231b is the spherical face 231c, then the insertion portion 231b is formed in such a manner that the section perpendicular to an axis center YP1 is reduced for the direction as shown by the arrow YA. Then, the insertion portion 231b is pressed to the wall face 217a in this spherical face 231c. In addition, the introducing portion 217 is taperingly formed reducing the inside thereof for the direction as shown by the arrow YA. Therefore, the insertion portion 231b is pressed in the direction as shown by the arrow YA in the introducing portion 217, thereby stress by pressing pressure respectively acting between the insertion portion 231b and the projection 220 forming the wall face 217a respectively effectively acts in such a manner that for the insertion portion 231b the cross section perpendicular to the axis center YP1 is elastically reduced, and for the projection 220, the inside of the introducing portion 217 is elastically enlarged in the direction as shown by the arrow YC. As a result, the cross section perpendicular to the axis center YP1 of the insertion portion 231b is reduced and the inside of the introducing portion 217 is enlarged in the direction as shown by the arrow YC, thereby the insertion portion 231b pressed in the direction as shown by the arrow YA moves in the direction as shown by the arrow YA in the introducing portion 217.

Furthermore, the piston 223 is pressed in the direction as shown by the arrow YA so as to move the insertion portion 231b in the direction as shown by the arrow YA in the introducing portion 217. Therefore, the insertion portion 231b is moved to the engagement holding portion 216 side passing through the boundary portion 219 between the introducing portion 217 and the engagement holding portion 216 from the arrow YA side thereof, and the insertion portion 231b is completely inserted into the engagement holding portion 216, thereby the pressing of the piston 223 is stopped. The insertion portion 231b is completely inserted into the engagement holding portion 216, thereby the hub engagement portion 231 and the piston engagement hole 215 are engaged with each other, and then the operation of engagement between the piston 223 and the hub 209 finishes.

On this occasion, pressing pressure force in the direction as shown by the arrow YA acts on the insertion portion 231b, thereby pressing pressure force in the direction as shown by the arrow YA also acts on the hub 209. However, the hub 209 is supported or can be supported in the direction as shown by the arrow YB with the hand supporting the syringe body 202 through the hub stop rib 207d of the hub insertion portion 204 or the end wall 208. Therefore, the hub 209 is not almost moved in the direction as shown by the arrow YA or the like if receiving pressing pressure force, and the hub 209 is not pulled out of the hole 208a of the end wall 208 in the direction as shown by the arrow YA.

Subsequently, the piston 223 is pulled against the syringe body 202 in the direction as shown by the arrow YB with a predetermined pulling force. That is, an action force in the direction as shown by the arrow YB by a predetermined pulling force acts on the piston 223 and the insertion portion 231b of the hub engagement portion 231. The restoring force in the direction as shown by the arrow YD which the hub insertion portion 204 has is set in such a predetermined sized one, as described heretofore, thereby the sealing between each seal portion 207e and each opening end 210e on the arrow YA side and on the arrow YB side is disengaged between the hub insertion portion 204 and the hub 209 against the action force in the direction as shown by the arrow YB by a predetermined pulling force. Therefore, the sealing between the hub stop rib 207d and the hub stop groove 210c is disengaged. The hub stop rib 207d and the hub stop groove 210c are disengaged from each other and the hub 209 is further advanced in the direction as shown by the arrow YB, and then the hub 209 is pulled until it is completely pulled out of the hub insertion hole 204b in the direction as shown by the arrow YB.

On this occasion, since the gap space 249 is formed between the hub 209 and the hub insertion hole 204b, contact between the hub 209 and the small cylindrical portion 207 is executed only through the hub stop rib 207d portion, and the pulling operation can be easily executed with a small force after the hub stop rib 207d and the hub stop groove 210c are disengaged from each other.

The piston 223 is further pulled in the direction as shown by the arrow YB in such a manner that the needle 221 inserted and fixed on the arrow YA side of the hub 209 is inserted into the hub insertion hole 204b in the direction as shown by the arrow YB from the hole 208a of the end wall

208 and further inserted into the inside space 202*a* of the main cylindrical portion 203 in the direction as shown by the arrow YB, and the top end of the needle 221 is completely inserted into the inside space 202*a*.

Figure 22:
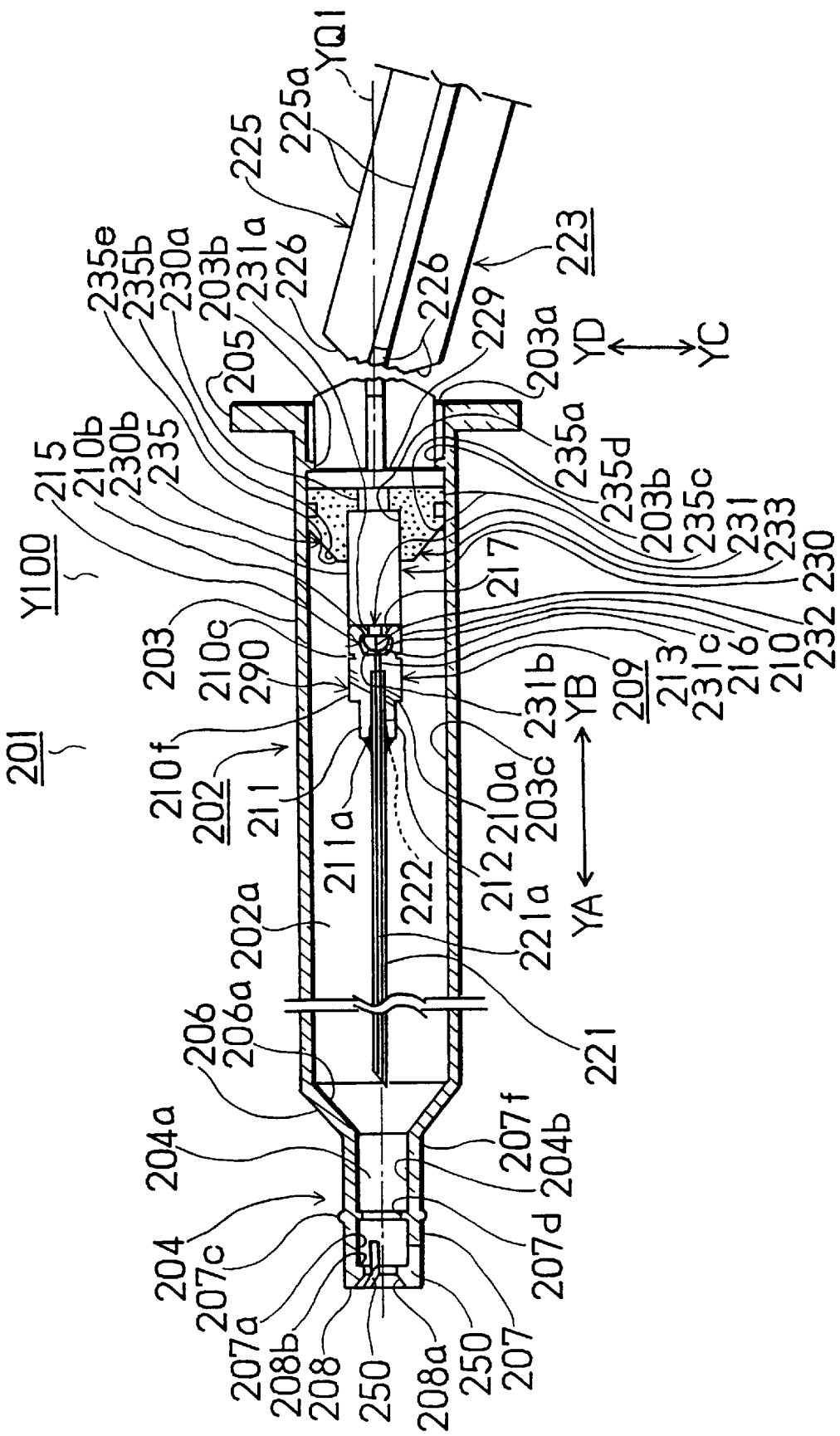
FIG. 22 is a view showing a routine of bending and taking the piston of the syringe assembly as shown in FIG. 19.

As shown in FIG. 22, the piston 223 is further pulled until the inner press plate 229 abuts on the engagement rib 203*b* of the main cylindrical portion 203 of the syringe body 202, and then the piston 223 is stopped.

Then, the notch 226 of the piston body 225 is positioned near the opening end 203*a* of the syringe body 202. Subsequently, a force in the direction as shown by the arrow YC is given to the piston 223. A force in the direction as shown by the arrow YC is added on the piston 223 with respect to the syringe body 202, thereby the piston body 225 is bent in the notch 226 which structure is relatively weak against bending stress in the piston body 225, and the piston body 225 is divided into the arrow YA side portion and the arrow YB side portion forming a boundary by the notch 226.

subsequently, the portion of the syringe body 202 side bent and taken and the portion of the outer press plate 227 of the piston 223 are disposed of so as to be discarded. Since the needle 221 is completely inserted and stored in the inside space 202*a* of the syringe body 202 being held with the top end portion of the piston 223 remaining in the inside space, there is no fear of hurting hands or the like and being secondarily infected from a wound by the needle 221. Therefore, waste disposal can be safely executed. As described before, the operation of storing the needle finishes and the use of the syringe assembly 201 and waste disposal after use all finish.

In the above-mentioned embodiment, the end portion 235*d*, capable of abutting on the taper 206 by the movement of the packing 233 in the directions as shown by the arrows YA and YB, that is, an engagement portion is formed at the packing 233. In addition, the surface 235*e*, that is, a pressing portion is formed such that the remaining space 251 is formed between the surface 235*e* and the taper 206 when the end portion 235*d* and the taper 206 are abutted on each other. However, the syringe assembly or the engagement portion of the packing 233 of the piston according to the present invention may be formed in the form excluding the end portion 235*d*.

Figure 23:
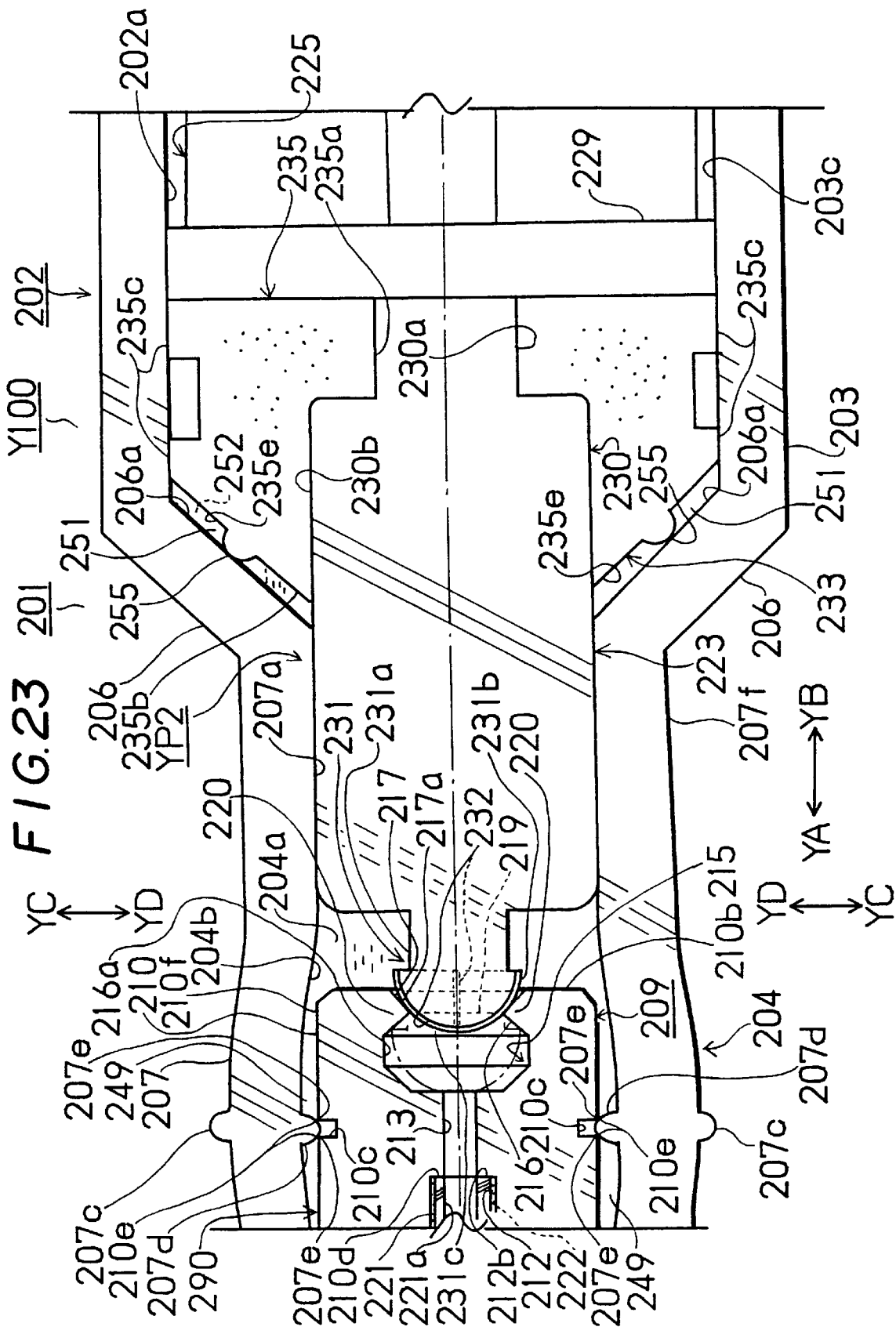
FIG. 23 is a sectional view showing an example of another syringe assembly according to the present invention.

For instance, as shown in FIG. 23, an engagement projection 255, capable of abutting on the taper 206 by movement of the packing 233 in the directions as shown by the arrows YA and YB, is formed on a surface side of the taper 235*b* of the packing 233, and then the engagement projection 255 may become to be the engagement portion. The surface 235*e* excluding the engagement projection 255 of the taper 235*b* becomes to be the Dressing portion, and the remaining space 251 can be formed between the surface 235*e*, that is, the pressing portion and the taper 206 when the engagement projection 255 and the taper 206 are abutted on each other.

Figure 25:
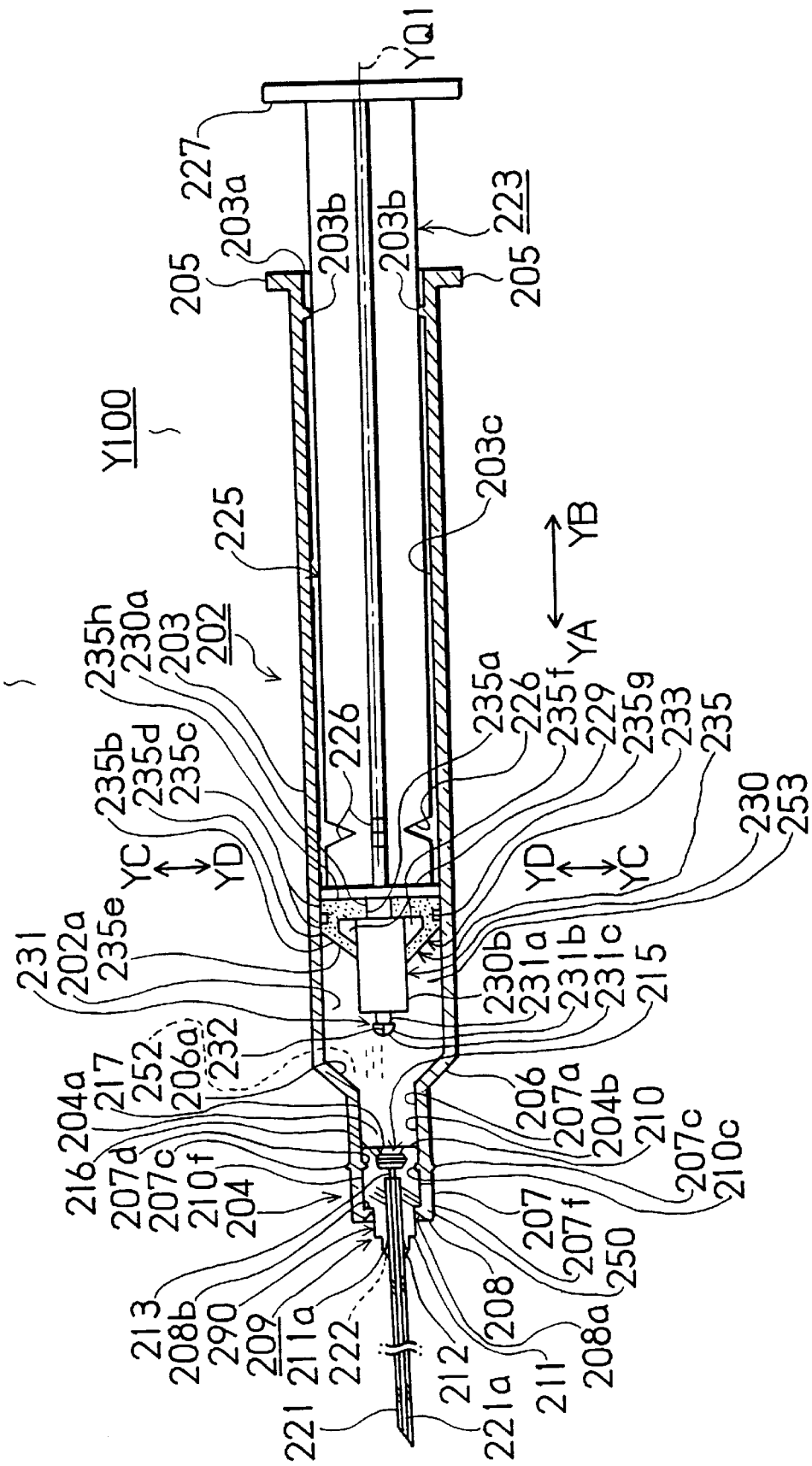
FIG. 25 is a typical sectional view showing the whole syringe assembly as shown in FIG. 24.

A syringe assembly 201 according to the present invention has a syringe Y100 made of resin, as shown in FIG. 25. A syringe body 202 is provided with the sryinge Y100 (FIG. 25 is a typical cross section of the syringe assembly 201, but a side is shown in a part of a piston 223, described hereinafter, not the section, for convenience.). A main cylindrical portion 203, cylindrically formed, is provided with the syringe body 202. A direction of an axis center of the main cylindrical portion 203, that is, the reciprocating directions parallel to an axis center YQ1 are an arrow YA direction in the figure (or the left direction of the paper of FIG. 25.) and an arrow YB direction (or the right direction of the paper of FIG. 25).

On the outer periphery side of the main cylindrical portion 203, a syringe support 205 is provided near an opening end 203*a* of the arrow YB side of the main cylindrical portion 203 (the right side of the paper of FIG. 25), in such a manner as forming a flange of the main cylindrical portion 203. On an inner peripheral face 203*c* side of the main cylindrical portion 203, an engagement rib 203*b*, projecting in the direction for the axis center YQ1 of the main cylindrical portion 203, that is, the direction as shown by an arrow YD of the figure, is annularly formed near the opening end 203*a* along the inner peripheral face 203*c*.

On the arrow YA side of the main cylindrical portion 203 (the left side of the paper of FIG. 25) a taper 206, which inside diameter is reduced at a predetermined rate of K1 for the direction as shown by the arrow YA, in the shape of a funnel, is formed unitedly connecting with the main cylindrical portion 203.

The inside of the main cylindrical portion 203 and the inside of the taper 206 communicate with each other in the directions as shown by the arrows YA and YB, and the space combined both insides is an inside space 202*a* of the syringe body 202.

Figure 24:
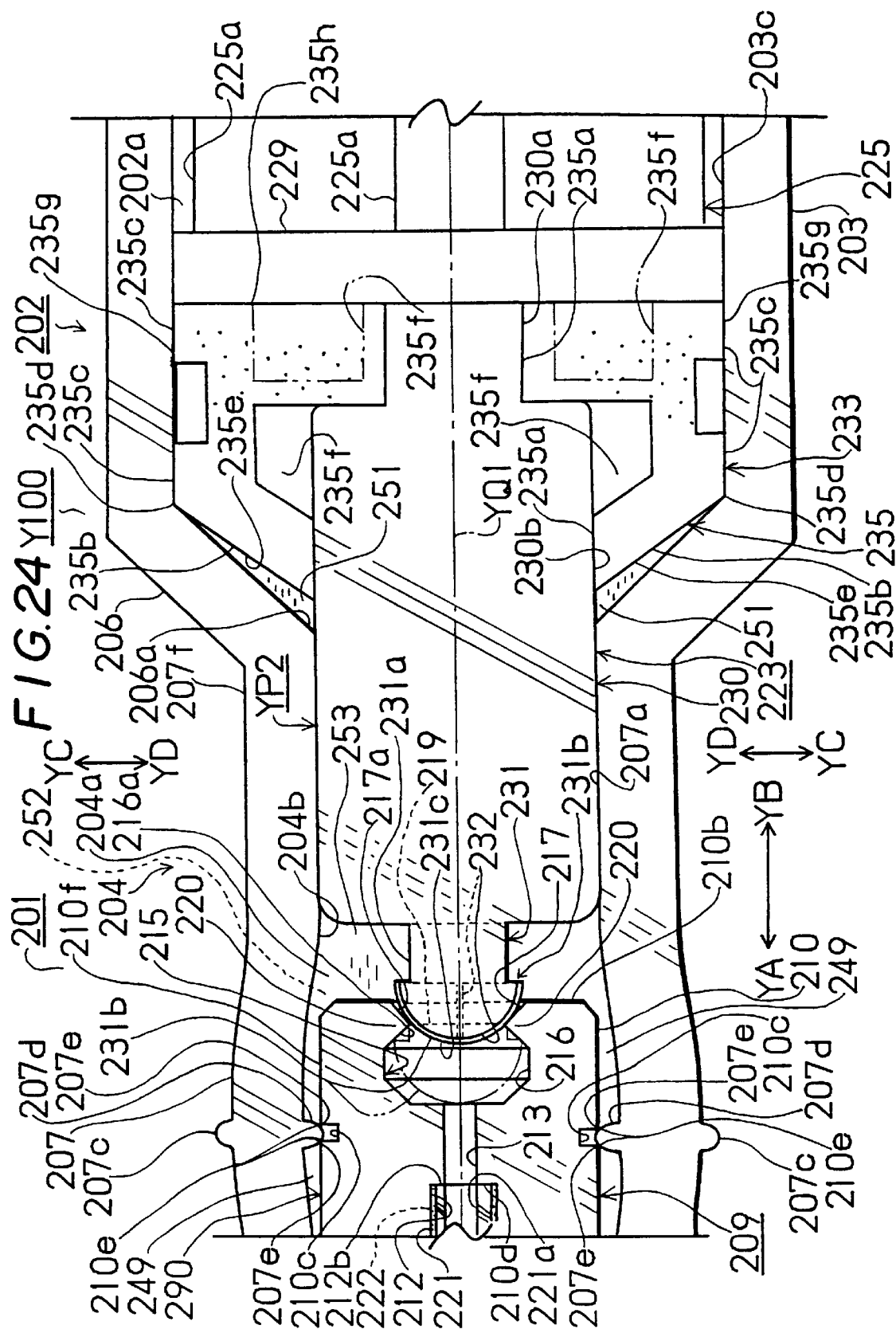
FIG. 24 is the sectional view showing the hub and the portion near the top of the piston, of an example of the syringe assembly according to the present invention.

On the side of the arrow YA of the taper 206, that is, on the side of the top of the syringe body 202, as shown in FIG. 24 and FIG. 25, a hub insertion portion 204 is formed unitely connecting with the taper 206, and the hub insertion portion 204 has a small Cylindrical portion 207. The small cylindrical portion 207 is formed unitedly connecting with the taper 206, coaxial with the main cylindrical portion 203, and the inside diameter of the small cylindrical portion 207 is smaller than one of the main cylindrical portion 203.

An inner peripheral face 207*a* side of the small cylindrical portion 207 is a hub insertion hole 204*b*. A hub stop rib 207*d* projecting for the axis center YQ1 is formed in the hub insertion hole 204*b*. The hub stop rib 207*d* is annularly formed along the inner peripheral face 207*a* of the small cylindrical portion 207. The section of a plane including the axis center YQ1 of the hub stop rib 207*d* (that is, the section as shown in FIG. 24) is a circular arc.

On the other hand, on an outer peripheral face 207*f* side of the small cylindrical portion 207, a stiffening rib 207*c* is annularly provided at the position corresponding to the hub stop rib 207*d* putting the small cylindrical portion 207 therebetween.

As shown in FIG. 20 or FIG. 25, an end wall 208, having an outside diameter equal to one of the small cylindrical portion 207, formed in the shape of a circular plate, is provided with the small cylindrical portion 207. The end wall 208 is provided united with the small cylindrical portion 207 contacting a wall face 208*b* of the arrow YB side of the end wall 208 and an end portion 207*b* of the arrow YA side of the small cylindrical portion 207 with each other. A hole 208*a* having a circular section is provided with the end wall 208 penetrating both front and back wall faces of the end wall 208 in the directions as shown by the arrows YA and YB such that the center is the axis center YQ1. The arrow YA side of the hole 208*a* is taperingly formed such that the sectional inside diameter is made bigger for the direction as shown by the arrow YA.

Three slits 250 are formed extending in the end wall 208 and the small cylindrical portion 207, as shown in FIG. 20 or FIG. 21. The slits 250 are formed extending in a radial direction with respect to the axis center YQ1, that is, in the directions as shown by arrows YC and YD in the figure (The arrow YC direction is opposite to the arrow YD direction.), communicating with the hole 208*a* provided at the end wall 208 in the end wall 208, and are formed parallel to the directions as shown by the arrows YA and YB in the small cylindrical portion 207. The slits 250 are formed on the arrow YA side rather than the hub stop rib 207d and the stiffening rib 207c, not reaching the hub stop rib 207d and the stiffening rib 207c.

Since the arrow YA side of the hub insertion portion 204 is divided into three parts by the slits 250, the portions of the hub insertion portion 204 formed the slits 250 are easy to be elastically enlarged in the direction as shown by the arrow YC. That is, when the syringe assembly 201 is assembled by inserting a hub 209 referred hereinafter into the syringe Y100, the portions of the hub insertion portion 204 formed slits 250 are elastically enlarged in the direction as shown by the arrow YC and the hole 208a of the end wall 208 is enlarged, thereby the hub 209 referred hereinafter can be inserted into the hub insertion hole 204b through the hole 208a.

The hub insertion portion 204 is comprised as explained heretofore. The syringe Y100 is comprised such that the syringe support 205, and the main cylindrical portion 203 comprising the syringe body 202, the taper 206 and the hub insertion portion 204 are unitedly formed.

The hub 209 made of resin, which is harder than the syringe Y100, is provided with the hub insertion hole 204b of the hub insertion portion 204. As shown in FIG. 24, FIG. 25 or FIG. 20, the hub 209 has a hub body 290. A main pillar portion 210, which longitudinal direction is parallel to the directions as shown by the arrows YA and YB, which axis center is the axis center YQ1, is provided in the shape of a cylinder with the hub body 290.

A hub stop groove 210c is formed on the side of the outer peripheral face 210f of the main pillar portion 210. The hub stop groove 210c is annularly formed along the outer peripheral side of the main pillar portion 210.

On an end face 210a side of the arrow YA side of the main pillar portion 210, a small pillar portion 211 is provided extending in the directions as shown by the arrows YA and YB, coaxial with and united with the main pillar portion 210. The hub 209 is provided such that the main pillar portion 210 of the hub 209 is inserted into the hub insertion hole 204b of the hub insertion portion 204, and the small pillar portion 211 of the hub 209 is inserted into the hole 208a of the end wall 208 so as to penetrate. The hub stop rib 207d of the hub insertion portion 204 and the hub stop groove 210c of the hub 209 are at the positions corresponding to and adjusting to each other, and then the hub stop rib 207d is engaged with the hub stop groove 210c inserting the top end side on the arrow YD side thereof into the hub stop groove 210c which is at the position corresponding and adjusting to one of the hub stop rib 207d.

Since the width of the hub stop rib 207d in the directions as shown by the arrows YA and YB is broader than one of the hub stop groove 210c in the directions as shown by the arrows YA and YB, the hub stop rib 207d is engaged with the hub stop groove 210c abutting on opening ends 210e, 210e of both sides of the arrows YA and YB of the hub stop groove 210c in seal portions 207e, 207e on the sides of the arrows YA and YB of the top thereof.

The inner peripheral face 207a of the small cylindrical portion 207 is not in contact with the outer peripheral face 210f of the hub 209 in the portions excluding the hub stop rib 207d, and a gap space 249 is formed bewteen the inner peripheral face 207a and the outer peripheral face 210f. That is, since contact between the inner peripheral face 207a side of the hub insertion portion 204b and the hub 209 is executed only between the hub stop rib 207d and the outer peripheral face 210f side of the hub 209, when the syringe assembly 201 is assembled by inserting the hub 209 into the syringe Y100, the hub 209 can be easily inserted into the hub insertion portion 204. In addition, in case of the operation of storing a needle, described hereinafter, the hub 209 is easily pulled out of the hub insertion portion 204 (As long as insertion of the hub 209 into the hub insertion portion 204 and pulling the hub 209 out of the hub insertion portion 204 can be easily executed, the portions excluding the hub stop rib 207d of the inner peripheral face 207a of the small cylindrical portion 207 may be in contact with the outer peripheral face 210f of the hub 209.).

An end face 210b of the arrow YB side of the main pillar portion 210 of the hub 209 is positioned on the arrow YA side rather than the boundary between the hub insertion hole 204b and the inside space 202a (that is, the boundary between the inside of the small cylindrical portion 207 and the inside of the taper 206), and the space of the inside of the hub insertion hole 204b on the arrow YB side rather than the end face 210b is a hole space 204a.

On the other hand, the hub insertion portion 204 is elastically deformed expanding the small cylindrical portion 207 in the direction as shown by the arrow YC in such a state that the hub 209 is provided with the hub insertion hole 204b. That is, the restoring force by elastic deformation of the small cylindrical portion 207 is transferred to the hub 209 through the hub stop rib 207d of the small cylindrical portion 207. That is, predetermined seal pressures by the restoring force are respectively acted between the hub stop rib 207d and the hub 209 in the portions between the seal portion 207e and the opening end 210e of the hub stop groove 210c in which both abut on each other, and then, the portion between the seal portion 207e and the opening end 210e is in a water tight state or an air tight state.

The rigidity of the hub stop rib 207 and the portion near thereof is increased in the small cylindrical portion 207 by the stiffening rib 207c which is at the position corresponding to the hub stop rib 207d putting the small cylindrical portion 207 therebetween, and then a predetermined restoring force by elastic deformation of the small cylindrical portion 207 can be effectively obtained.

As shown in FIG. 24, FIG. 25 or FIG. 20., a needle insertion hole 212 is provided with the hub 209. The needle insertion hole 212 is provided forming a circular opening 212a, which center is the axis ceter YQ1, at an end face 211a of the arrow YA side of the small pillar portion 211 of the hub 209, extending from the end face 211a in the direction as shown by the arrow YB. An end portion 212b of the arrow YB side of the needle insertion hole 212 reaches the inside of the main pillar portion 210 and the end portion 212b is in contact with a wall face 210d of the main pillar portion 210. In the needle insertion hole 212, tapers are adequately formed such that the diameter of the needle insertion hole 212 is made narrower for the direction as shown by the arrow YB.

On the other hand, a flow hole 213 is provided with the main pillar portion 210 of the hub 209 adjacent to the arrow YB side of the needle insertion hole 212 (right side of the paper of FIG. 24). The flow hole 213 is cylindrically formed such that its center is the axis center YQ1 and its diameter is smaller than one of the end portion 212b of the needle insertion hole 212. The flow hole 213 is provided forming a circular opening at the wall face 210d of the main pillar portion 210, communicating with the needle insertion hole 212.

A piston engagement hole 215, which section perpendicular to the axis center YQ1 is a circle, is provided with the main pillar portion 210 of the hub 209 communicating with and adjacent to the arrow YB side of the flow hole 213, coaxial with the axis center YQ1. The arrow YB side of the piston engagement hole 215 is open outside in the end face 210b of the main pillar portion 210.

The piston engagement hole 215 is comprised of two parts, an engagement holding portion 216 of the arrow YA side and an introducing portion 217 of the arrow YB side. The engagement holding portion 216 is almost cylindrical shape, coaxial with the axis center YQ1, and both end portion sides of the arrows YA and YB thereof are taperingly formed such that each diameter is made narrower for the direction as shown by the arrow YA or arrow YB. The end portion side of the arrow YA side of the engagement holding portion 216 is communicated and connected with the flow hole 213.

The introducing portion 217 communicates with and is adjacent to the end portion of the arrow YB side of the engagement holding portion 216. The diameter of the introducing portion 217 is made bigger for the direction as shown by the arrow YB. Then, the portion sandwitched between a wall face 216a facing the engagement holding portion 216 and a wall face 217a facing the introducing portion 217 of the main pillar portion 210 forms a projection 220 projecting for the axis center YQ1 with a boundary portion 219 between the engagement holding portion 216 and the introducing portion 217 as an apex.

On the other hand, as shown in FIG. 25 or FIG. 20, a needle 221 is inserted into the needle insertion hole 212 of the hub 209. The needle 221 is inserted from the rear end portion side into the needle insertion hole 212 and the top end side is positioned outside of the syringe body 202. The rear end of the needle 221 abuts on the wall face 210d formed on the arrow YB side of the needle insertion hole 212. The medium flow hole 221a provided penetrating from the top end to the rear end side of the needle 221 and the flow hole 213 are adjacent to and communicate with each other in the directions as shown by the arrows YA and YB.

An adhesive 222 is injected into the needle insertion hole 212 filling between the needle 221 and the hub 209 and is hardened.

The piston 223 is provided with the syringe assembly 201, as shown in FIG. 24 or FIG. 25 (FIG. 25 is a typical sectional view of the syringe assembly 201, but with respect to a piston body 225, an outer press plate 227, an inner press plate 229, a packing support 230, a hub engagement portion 231, referred hereinafter, of the piston 223, their sides are shown, not their sections, for convenience.)

The piston 223 has the bar-shaped piston body 225 extending in the directions as shown by the arrows YA and YB. The piston body 225 is comprised such that two congruent plate portions 225a, each which is a plate shaped rectangle especially long in the directions as shown by the arrows YA and YB, are unitedly cross provided with each other such that the sections thereof form the shape of a cross. The width perpendicular to the directions as shown by the arrows YA and YB of the plate face of the plate portion 225a is almost equal to the inside diameter in the engagement rib 203b of the main cylindrical portion 203, and the piston body 225 is inserted into the main cylindrical portion 203 through the opening end 203a from the arrow YA side of the piston body 225.

On each plate portion 225a of the piston body 225, notches 226 are formed from both side portions of respective plate portions 225a, 225a in the direction of the axis center (that is, the axis center YQ1) of the piston body 225 in the shape of a wedge near the direction as shown by the arrow YA. Four notches 226 are provided at the positions adjusted one another in the directions as shown by the arrows YA and YB.

The outer press plate 227 in the shape of a circular plate, which plate face is perpendicular to the directions as shown by the arrows YA and YB, is provided united with the piston body 225 on the end portion side of the arrow YB side of the piston body 225.

The inner press plate 229 in the shape of a circular plate, which plate face is perpendicular to the directions as shown by the arrows YA and YB, is provided united and coaxial with the piston body 225 on the end portion side of the arrow YA side of the piston body 225 (Therefore, the inner press plate 229 is positioned inside of the main cylindrical portion 203.), and the diameter of the inner press plate 229 is almost equal to the inside diameter of the main cylindrical portion 203 (Therefore, the diameter of the inner press plate 229 is bigger than the inside diameter in the engagement rib 203b of the main cylindrical portion 203.).

As shown in FIG. 25, the packing support 230 is provided with the inner press plate 229 on the arrow YA side thereof. A pillar portion 230a in the shape of a cylinder, extending in the directions as shown by the arrows YA and YB, is provided with the packing support 230, being coaxial with the inner press plate 229. The diameter of the pillar portion 230a is smaller than one of the inner press plate 229. The pillar portion 230a is provided on the arrow YA side of the inner press plate 229, being united with the inner press plate 229. As shown in FIG. 24 or FIG. 25, an insertion pillar portion 230b in the shape of a cylinder, extending in the directions as shown by the arrows YA and YB being coaxial with the pillar portion 230a, having an outside diameter almost equal to the inside diameter of the small cylindrical portion 207, is provided on the arrow YA side of the pillar portion 230a, being united with the pillar portion 230a.

The hub engagement portion 231 is provided on the arrow YA side of the insertion pillar portion 230b. A pillar portion 231a in the shape of a cylinder, extending in the directions as shown by the arrows YA and YB, is provided with the hub engagement portion 231, being coaxial with the insertion pillar portion 230b. The diameter of the pillar portion 231a is smaller than one of the insertion pillar portion 230b. The pillar portion 231a is provided on the arrow YA side of the insertion pillar portion 230b, being united with the insertion pillar portion 230b. An insertion portion 231b in the shape of a hemi-sphere, which diameter is bigger than one of the pillar portion 231a, is provided on the arrow YA side of the pillar portion 231a, being united with the pillar portion 231a facing a spherical face 231c side to the arrow YA side. A plurality of grooves 232 in the shape of a stripe are provided with the insertion portion 231b, being parallel to the spherical face 231c, extending from the top portion of the arrow YA side to the arrow YB side.

The diameter of the pillar portion 231a is almost equal to the inside diameter in the boundary portion 219 of the piston engagement hole 215 provided with the hub 209. Therefore, the diameter of the insertion portion 231b is bigger than one of the boundary portion 219. The size of the insertion portion 231b allows itself to be sufficiently inserted into and to be held by the engagement holding portion 216 of the piston engagement hole 215.

On the other hand, as shown in FIG. 24, a packing 233 made of flexible resin, is supported with the packing support 230. The packing 233 has a packing body 235 which is inserted into inside of the main cylindrical portion 203 of the syringe Y100 so as to be adjusted. An engagement hole 235a penetrating the packing body 235 in the directions as shown by the arrows YA and YB is provided with the packing body 235. The engagement hole 235a penetrates the pillar portion 230a of the packing support 230 and a part of the insertion pillar portion 230b. That is, the packing 233 engages with the packing support 230 such that the packing support 230 penetrates the engagement hole 235a, thereby the packing 233 is supported by the packing support 230. A supporting face 235h, perpendicular to the directions as shown by the arrows YA and YB, is formed at the end portion of the arrow YB side of the packing body 235. The supporting face 235h abuts on the inner press plate 229 so as to easily receive a force in the direction as shown by the arrow YA by the inner press plate 229. The packing 233 and the pillar portion 230a in the engagement hole 235a are closely contacted with each other, and the portion therebetween is sealed against water or against air.

A hollow clearance space 235f is formed inside of the packing body 235, enclosing the engagement hole 235a from the arrow YC side and being adjacent to and communicating with the engagement hole 235a (Therefore, the clearance space 235f is enclosed by the packing body 235 on the arrows YA, YB and YC sides thereof, and is contacted with the insertion pillar portion 230b of the packing support 230 on the arrow YD side thereof.). The packing 233 and the insertion pillar portion 230b are contacted with each other in the portion of the arrow YA side rather than the clearance space 235f, of the engagement hole 235a, but both are not closely contacted with each other, that is, the portion therebetween is not sealed against water or against air. That is, air or liquid can flow between the clearance space 235f and the outside of the arrow YA side of the packing body 235 through the engagement hole 235a.

The arrow YA side of the packing body 235 is a taper 235b. While the form of the inside of the taper 206 of the syringe body 202 is a taper, reducing the inside diameter at a predetermined rate K1 for the direction as shown by the arrow YA, as described before, the form of the taper 235b in a natural state is a taper, reducing the outside diameter at a predetermined rate K2, which is bigger than a predetermined rate K1. That is, the taper 235b is formed forming a remaining space 251 between a surface 235e excluding the end portion 235d of the taper 235b (that is, liquid pressing face capable of pressing the injection medium) and the inner peripheral face 206a of the taper 206 when an end portion 235d of the arrow YB side of the taper 235b in a natural state abuts on an inner peripheral face 206a of the taper 206 inside of the taper 206.

A part of the arrow YA side of the insertion pillar portion 230b of the packing support 230 penetrating the engagement hole 235a further projects on the arrow YA side rather than the taper 235b.

In such a state that the end portion 235d of the taper 235b is abutted on the inside of the taper 206 of the syringe body 202 when the taper 235b of the packing 233 is in a natural state, as shown in FIG. 24, the insertion pillar portion 230b of the packing support 230 enagaging with the packing 233 is inserted into the hub insertion hole 204b of the syringe body 202. The form of the packing 233 is set so as to become such a state where the spherical face 231c of the insertion portion 231b of the hub engagement portion 231 contacts with the wall face 217a facing the introducing portion 217 of the piston engagement hole 215.

The outside diameter of the packing body 235 of the packing 233 is almost equal to one of the inner press plate 229. However, on the outer peripheral side of the packing body 235, annular folds 235c are double formed along the outer periphery of the packing body 235 arranging in a line in the directions as shown by the arrows YA and YB. Therefore, the packing 233 is inserted into the main cylindrical portion 203 of the syringe body 202, reducing the portion near the fold 235c of the packing body 235 in the direction for the axis center YQ1, that is, in the direction as shown by the arrow YD by elastic deformation. That is, the packing 233 and the main cylindrical portion 203 are closely contacted with each other in the folds 235c and the inner peripheral face 203c, and the portion between the packing 233 and the main cylindrical portion 203 is sealed against water or against air.

The outer peripheral side of the packing body 235, that is, the surface of the side where the folds 235c and the like are formed is a sliding face 235g facing the inner peripheral face 203c of the syringe body 202. The packing 233 contacts with the inner peripheral face 203c in the sliding face 235g. Since the inner peripheral face 203c and the sliding face 235g are smoothly formed, the piston 223 inserted the packing 233 therein is free to slide and move in the directions as shown by the arrows YA and YB in the inside space 202a of the main cylindrical portion 203.

The syringe assembly 201 is comprised as before, and then the syringe assembly 201 is used and, after that, the syringe assembly 201 is discarded as follows.

At first, the needle 221 of the syringe assembly 201 is advanced into an injection medium 252 in a medicine bottle (not shown), the piston 223 is pulled in the direction as shown by the arrow YB with respect to the syringe body 202, and by differential pressure, the injection medium 252 in the medicine bottle flows to a medium holding space 253 which is a space on the needle 221 side rather than the piston 223 of the hole space 204a of the hub insertion portion 204 and the inside space 202a of the syringe body 202 passing through the medium flow hole 221a of the needle 221, the flow hole 213 of the hub 209 and the piston engagement hole 215 so as to fill the syringe assembly 201 with the injection medium 252.

In case of filling with the injection medium 252, a differential pressure force in the direction as shown by the arrow YB by differential pressure between the outside and the medium holding space 253 acts on the hub 209. However, the restoring force in the direction as shown by the arrow YD which the hub insertion portion 204 has is set in such a predetermined size as described heretofore, thereby sealing between each seal portion 207e and each opening end 210e of the arrow YA side and the arrow YB side is not disengaged between the hub insertion portion 204 and the hub 209 against the maximum differential pressure force predicted.

After filling with the injection medium 252, the needle 221 of the syringe assembly 201 is stuck into an injection portion of a patient. Subsequently, the outer press plate 227 of the piston 223 is pressed in the direction as shown by the arrow YA so as to drive the piston 223 with respect to the syringe body 202 in the direction as shown by the arrow YA. The injection medium 252 of the medium holding space 253 is pressurized so as to flow into the body in the injection portion of a patient through the piston engagement hole 215 of the hub 209, the flow hole 213, the medium flow hole 221a of the needle 221.

On this occasion, the injection medium 252 is pressurized and an action force by the pressure of the injection medium 252 is added to the hub 209 in the direction as shown by the arrow YA from the end face 210b side of the hub 209 adjacent to the injection medium 252. However, the restoring force in the direction as shown by the arrow YD which the hub insertion portion 204 has is set in such a predetermined size as described heretofore, thereby sealing between each seal portion 207e and each opening end 210e on the arrow YA side and the arrow YB side is not disengaged between the hub insertion portion 204 and the hub 209 against the maximum action force predicted.

After a predetermined amount of the injection medium 252 flows into the body in the injection portion of a patient, that is, after the piston 223 is driven to the position where the end portion 235d of the taper 235b of the packing 233 is abutted on the inside of the taper 206 of the syringe body 202, and as shown in FIG. 24, the insertion portion 231b of the hub engagement portion 231 of the piston 223 abuts on the wall face 217a in the introducing hole 217 of the piston engagement hole 215 of the hub 209, that is, to an injection end position YP2 in the figure, the whole syringe assembly 201 is pulled in the direction as shown by the arrow YB to a patient, and the needle 221 is pulled out of the injection portion of a patient.

After the needle 221 is pulled out, the operation of storing the needle is executed as follows.

In the operation of storing the needle, the engagement operation between the piston 223 and the hub 209 is executed as follows.

That is, the outer press plate 227 of the piston 223 is further pressed with fingers in the direction as shown by the arrow YA so as to press the piston body 225 in the direction as shown by the arrow YA, and then the insertion pillar portion 230b of the packing support 230 and the hub engagement portion 231 are fed in the direction as shown by the arrow YA in the hub insertion hole 204b.

Just before start of the operation of storing the needle, the piston 223 is positioned such that the taper 235b in a natural state is positioned corresponding to the inside of the taper 206, the end portion 235d of the arrow YB side of the taper 235b abuts on the inner peripheral face 206a of the taper 206, and the remaining space 251 is formed between the surface 235e excluding the end portion 235d of the taper 235b and the inner peripheral face 206a of the taper 206. Therefore, by pressing pressure in the direction as shown by the arrow YA of the piston body 225, in the packing 233, the portion on the arrow YB side from the portion near the end portion 235d abutting on the taper 206 is compressed in the directions as shown by the arrows YB and YD, and the other part is pressed out in the direction as shown by the arrow YA making use of the remaining space 251 in such a manner that the surface 235e approaches the taper 206. Therefore, since the quantity of elastic compression in the packing 233 is extremely reduced by the remaining space 251, the piston 223 can be operated with extremely small force.

In addition, the clearance space 235f is formed inside of the packing body 235, the clearance space 235f is reduced with the packing body 235 when the packing body 235 is elastically compressed. Therefore, since the quantity of elastic compression in the packing 233 is reduced by the clearance space 235f, the piston 233 can be operated with extremely small force.

As shown in FIG. 24, just before start of the operation of storing the needle, the hole space 204a between the end face 210b of the hub 209 and the insertion pillar portion 230b of the piston 223 side (that is, the medium holding space 253) and the remaining space 251 (that is, the medium holding space 253) are filled with the remaining injection medium 252. The operation of storing the needle is started, the piston 223 is pressed and moved in the direction as shown by the arrow YA as described heretofore, thereby the remaining injection medium 252 is pressurized. However, a plurality of grooves 232 are provided with the insertion portion 231b, as described heretofore, and then these grooves 232 are not closed when the insertion portion 231b and the wall face 217a are abutted on each other by pressing. Therefore, when the insertion portion 231b and the wall face 217a are abutted on each other by pressing, the hole space 204a or the remaining space 251 side and the engagement holding portion 216 side communicate with the grooves 232. The remaining injection medium 252 pressurized of the hole space 204a or the remaining space 251 flows to the engagement holding portion 216 side through these grooves 232 (This is because the injection medium 252 of the remaining space 251 can flow to the hole space 204a side passing between the insertion pillar portion 230b and the small cylindrical portion 207 since the portion between the insertion pillar portion 230b and the small cylindrical portion 207 is not water tight.), and furthermore, is expelled outside through the flow hole 213 and the medium flow hole 221a of the needle 221. That is, when the operation of storing the needle starts and the piston 223 is pressed and moved in the direction as shown by the arrow YA, the remaining injection medium 252 pressurized in the hole space 204a or the remaining space 251 is appropriately expelled outside, and the pressure is not extremely increased. Therefore, the resistance by pressure of remaining injection medium 252 is not extremely acted on the piston 223, and then the piston 223 is pressed and moved in the direction as shown by the arrow YA with extremely small force.

While the packing 233 is elastically reduced, the insertion pillar portion 230b of the packing support 230 and the hub engagement portion 231 are pressed and moved in the direction as shown by the arrow YA in the hub insertion portion 204b, and the insertion portion 231b of the hub engagement portion 231 is pressed and moved in the direction as shown by the arrow YA from the introducing portion 217 of the piston engagement hole 215 for the engagement holding portion 216.

That is, the piston 223 is pressed and moved in the direction as shown by the arrow YA, thereby the insertion portion 231b is pressed to the wall face 217a in the introducing portion 217. However, the arrow YA side of the insertion portion 231b is the spherical face 231c, then the insertion portion 231b is formed in such a manner that the section perpendicular to the axis center YQ1 is reduced for the direction as shown by the arrow YA. Then, the insertion portion 231b is pressed to the wall face 217a in this spherical face 231c. In addition, the introducing portion 217 is taperingly formed reducing the inside thereof for the direction as shown by the arrow YA. Therefore, the insertion portion 231b is pressed in the direction as shown by the arrow YA in the introducing portion 217, thereby stress by pressing pressure respectively acting between the insertion portion 231b and the projection 220 forming the wall face 217a respectively effectively acts in such a manner that for the insertion portion 231b the cross section perpendicular to the axis center YQ1 is elastically reduced, and for the projection 220, the inside of the introducing portion 217 is elastically enlarged in the direction as shown by the arrow YC. As a result, the cross section perpendicular to the axis center YQ1 of the insertion portion 231b is reduced and the inside of the introducing portion 217 is enlarged in the direction as shown by the arrow YC, thereby the insertion portion 231b pressed in the direction as shown by the arrow YA moves in the direction as shown by the arrow YA in the introducing portion 217.

Furthermore, the piston 223 is pressed in the direction as shown by the arrow YA so as to move the insertion portion 231b in the direction as shown by the arrow YA in the introducing portion 217. Therefore, the insertion portion 231b is moved on the engagement holding portion 216 side passing through the boundary portion 219 between the introducing portion 217 and the engagement holding portion 216 from the arrow YA side thereof, and the insertion portion 231b is completely inserted into the engagement holding portion 216, thereby the pressing of the piston 223 is stopped. The insertion portion 231b is completely inserted into the engagement holding portion 216, thereby the hub engagement portion 231 and the piston engagement hole 215 are engaged with each other, and then the operation of engagement between the piston 223 and the hub 209 finishes.

On this occasion, pressing pressure force in the direction as shown by the arrow YA acts on the insertion portion 231b, thereby pressing pressure force in the direction as shown by the arrow YA also acts on the hub 209. However, the hub 209 is supported or can be supported in the direction as shown by the arrow YB with the hand supporting the syringe body 202 through the hub stop rib 207d of the hub insertion portion 204 or the end wall 208. Therefore, the hub 209 is not almost moved in the direction as shown by the arrow YA or the like if receiving pressing pressure force, and the hub 209 is not pulled out of the hole 208a of the end wall 208 in the direction as shown by the arrow YA.

Subsequently, the piston 223 is pulled against the syringe body 202 in the direction as shown by the arrow YB with a predetermined pulling force. That is, an action force in the direction as shown by the arrow YB by a predetermined pulling force acts on the piston 223 and the insertion portion 231b of the hub engagement portion 231. The restoring force in the direction as shown by the arrow YD which the hub insertion portion 204 has is set in a predetermined size, as described heretofore, thereby the sealing between each seal portion 207e and each opening end 210e on the arrow YA side and on the arrow YB side is disengaged between the hub insertion portion 204 and the hub 209 against the action force in the direction as shown by the arrow YB by a predetermined pulling force. Therefore, the sealing between the hub stop rib 207d and the hub stop groove 210c is disengaged. The hub stop rib 207d and the hub stop groove 210c are disengaged from each other and the hub 209 is further advanced in the direction as shown by the arrow YB, and then the hub 209 is pulled until it is completely pulled out of the hub insertion hole 204b in the direction as shown by the arrow YB.

On this occasion, since the gap space 249 is formed between the hub 209 and the hub insertion hole 204b, contact between the hub 209 and the small cylindrical portion 207 is executed only through the hub stop rib 207d portion, and the pulling operation can be easily executed with a small force after the hub stop rib 207d and the hub stop groove 210c are disengaged from each other.

The piston 223 is further pulled in the direction as shown by the arrow YB in such a manner that the needle 221 inserted and fixed on the arrow YA side of the hub 209 is inserted into the hub insertion hole 204b in the direction as shown by the arrow YB from the hole 208a of the end wall 208 and further inserted into the inside space 202a of the main cylindrical portion 203 in the direction as shown by the arrow YB, and the top end of the needle 221 is completely inserted into the inside space 202a.

Figure 26:
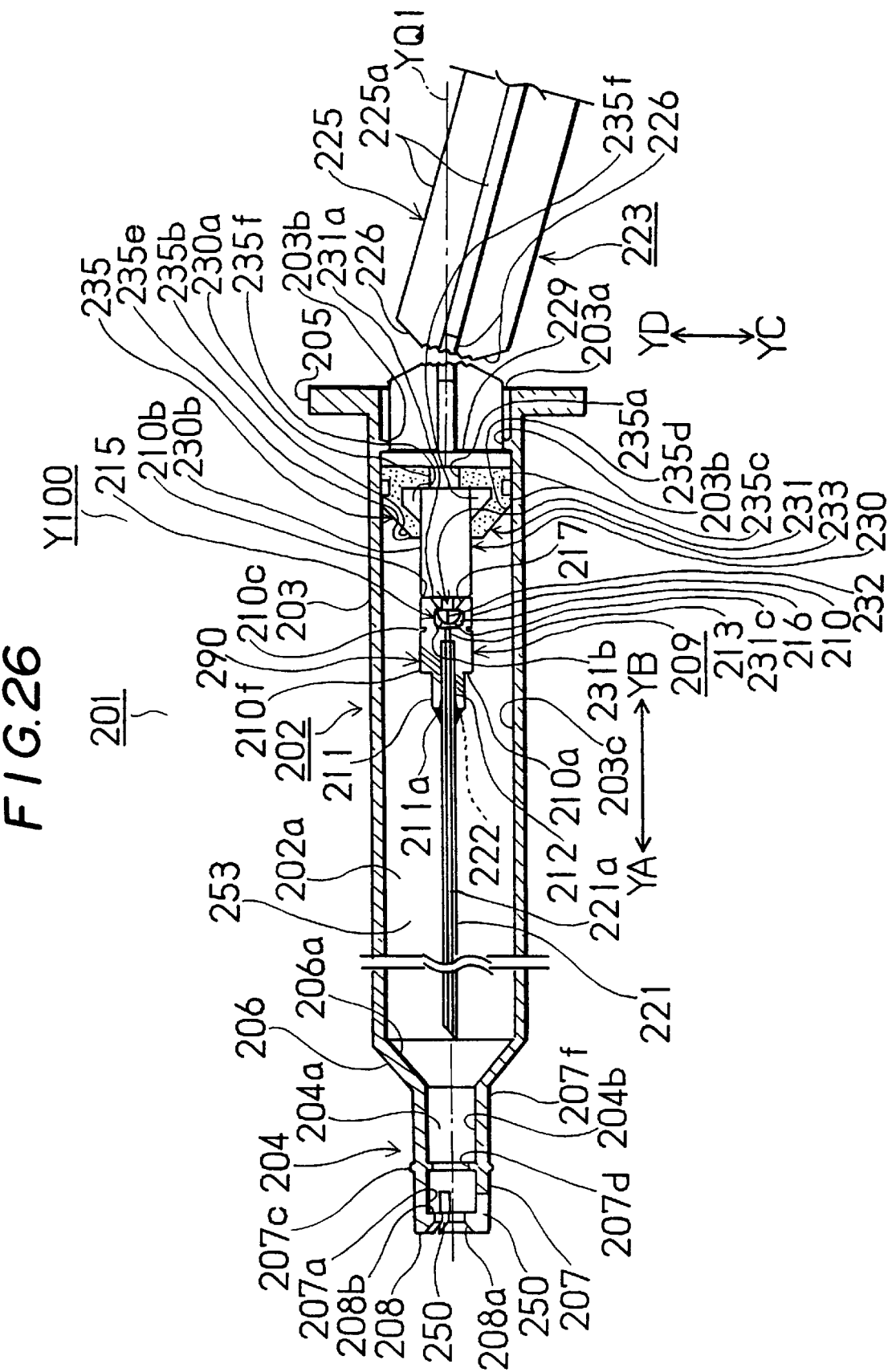
FIG. 26 is a view showing an operation of bending and taking the piston of the syringe assembly as shown in FIG. 25.

As shown in FIG. 26, the piston 223 is further pulled until the inner press plate 229 abuts on the engagement rib 203b of the main cylindrical portion 203 of the syringe body 202, and then the piston 223 is stopped.

Then, the notch 226 of the piston body 225 is positioned near the opening end 203a of the syringe body 202.

Subsequently, a force in the direction as shown by the arrow YC is given to the piston 223. A force in the direction as shown by the arrow YC is added to the piston 223 with respect to the syringe body 202, thereby the piston body 225 is bent in the notch 226 which structure is relatively weak against bending stress in the piston body 225, and the piston body 225 is divided into the arrow YA side portion and the arrow YB side portion forming a boundary by the notch 226.

Subsequently, the portion of the syringe body 202 side bent and taken and the portion of the outer press plate 227 of the piston 223 are disposed of so as to be discarded. Since the needle 221 is completely inserted and stored in the inside space 202a of the syringe body 202 being held with the top end portion of the piston 223 remaining in the inside space, there is no fear of hurting hands or the like and being secondarily infected from a wound by the needle 221. Therefore, waste disposal can be safely executed. As described before, the operation of storing the needle finishes and the use of the syringe assembly 201 and waste disposal after use all finish.

In the above-mentioned embodiment, the clearance space 235f of the packing 233 is formed communicating outside of the packing 233 through the engagement hole 235a and the like. However, the clearance space 235f may be formed not communicating with outside of the packing 233, that is, inside of the packing 233 as long as the clearance space 235f can be reduced and changed in size when the packing 233 is compressed.

In addition, in the above-mentioned embodiment, the clearance space 235f of the packing 233 is formed being adjacent to the engagement hole 235a. However, as long as the clearance space 235f is formed inside of the packing 233, and between the engagement hole 235a and the sliding face 235g, for instance, the clearance space 235f may be formed being open to the supporting face 235h of the packing body 235, as shown by the two-dot chain line of FIG. 24, that is, may be formed adjacent to he inner press plate 229.

In addition, in order to prevent entering the injection medium 252 and air into the clearance space 235f, the clearance space 235f may be filled with soft material, such as rubber, soft plastics, porous rubber having flexibility, porous plastics, which is softer than the packing 233.

In addition, in the above-mentioned embodiment, the piston side engagement means is the hub engagement portion 231 in the shape of a projection, and the hub side engagement means is the piston engagement hole 215 in the shape of a hole. However, the piston side engagement means may be formed as a hole and the hub side engagement means may be formed as a projection as long as the piston side engagement means and the hub side engagement means can be enagaged with each other.

Figure 28:
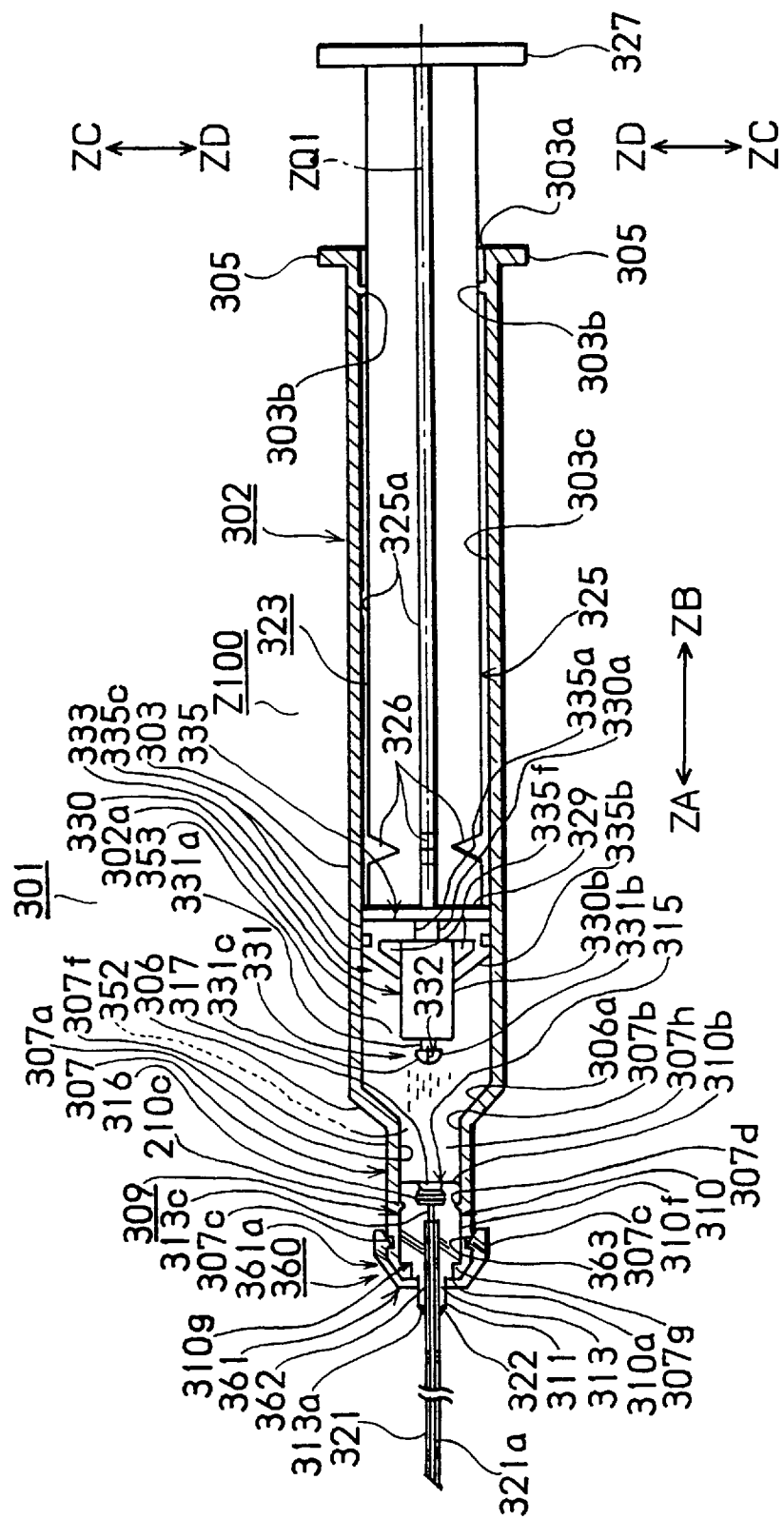
FIG. 28 is a sectional view showing a whole syringe assembly to which the needle assembly unit and the syringe as shown in FIG. 27 are applied.

A syringe assembly 301 just before an injection action, or in such a state that a needle and a syringe are connected with each other, has a syringe Z100 made of resin, as shown in FIG. 28. A syringe body 302 is provided with the syringe Z100 (FIG. 28 is a typical cross section of the syringe assembly 301, but a side is shown in a part of a piston 323, described hereinafter, not the section, for convenience.). A main cylindrical portion 303, cylindrically formed, is provided with the syringe body 302. A direction of an axis center of the main cylindrical portion 303, that is, the reciprocating directions parallel to an axis center ZQ1 are an arrow ZA direction in the figure (or the left direction of the paper of FIG. 28.) and an arrow ZB direction (or the right direction of the paper of FIG. 28).

On the outer periphery side of the main cylindrical portion 303, a syringe support 305 is provided near an opening end 303a of the arrow ZB side of the main cylindrical portion 303 (the right side of the paper of FIG. 28), in such a manner as forming a flange of the main cylindrical portion 303. On an inner peripheral face 303c side of the main cylindrical portion 303, an engagement rib 303b, projecting in the direction for the axis center ZQ1 of the main cylindrical portion 303, that is, the direction as shown by an arrow ZD of the figure, is annularly formed near the opening end 303a along the inner peripheral face 303c.

Figure 27:
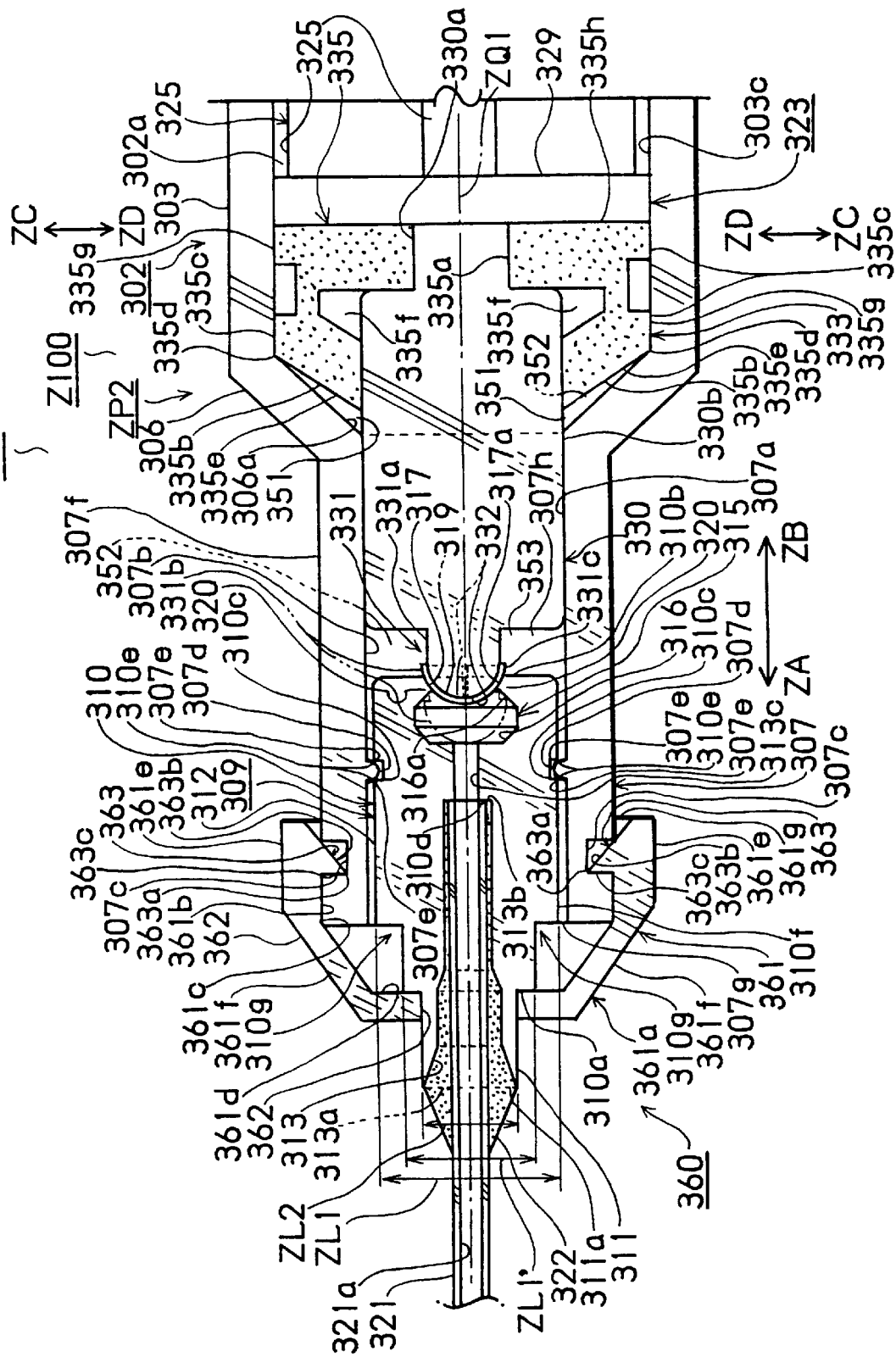
FIG. 27 is a sectional view showing connecting portion of an example of a needle assembly unit according to the present invention and an example of a syringe according to the present invention.

As shown in FIG. 27 or FIG. 28, on the arrow ZA side of the main cylindrical portion 303 a taper 306, which inside diameter is reduced at a predetermined rate of K1 for the direction as shown by the arrow ZA, in the shape of a funnel, is formed unitedly connecting with the main cylindrical portion 303.

The inside of the main cylindrical portion 303 and the inside of the taper 306 communicate with each other in the directions as shown by the arrows ZA and ZB, and the space combined both insides is an inside space 302a of the syringe body 302.

On the side of the arrow ZA of the taper 306, that is, on the side of the top of the syringe body 302, as shown in FIG. 27 and FIG. 28, a hub insertion portion 307 is formed unitely connecting with the taper 306. The hub insertion portion 307 is cylindrically formed, coaxial with the main cylindrical portion 303. The inside diameter of the hub insertion portion 307 is smaller than one of the main cylindrical portion 303.

An inner peripheral face 307a side of the hub insertion portion 307 is a hub insertion hole 307b. A hub stop rib 307d projecting for the axis center ZQ1 is formed in the hub insertion hole 307b. The hub stop rib 307d is annularly formed along the inner peripheral face 307a. The section of a plane including the axis center ZQ1 of the hub stop rib 307d (that is, the section as shown in FIG. 27 or FIG. 28) is a circular arc.

On the other hand, on an outer peripheral face 307f side of the hub insertion portion 307, a hub fixed member engagement groove 307c is annularly provided along the outer peripheral face 307f.

The top portion of the arrow ZA side of the hub insertion portion 307 is an opening end 307g. The inside diameter of the hub insertion portion 307 (in such a state that it is not elastically deformed) is set as a predetermined size extending from the end portion of the arrow ZB side which is a boundary between the hub insertion portion 307 and the taper 306 to the end portion of the arrow ZA side which is the opening end 307g excluding the hub stop rib 307d.

The hub insertion portion 307 is comprised as described heretofore. The syringe Z100 is comprised such that the syringe support 305, the main cylindrical portion 303 comprising the syringe body 302, the taper 306 and the hub insertion portion 307 are unitedly formed.

A needle assembly unit 360 is connected with the syringe Z100. The needle assembly unit 360 is comprised of a hub 309, a needle 321 and a hub fixed member 361, as shown in FIG. 27.

The hub 309 of the needle assembly unit 360 is provided with the hub insertion hale 307b of the hub insertion portion 307 of the syringe Z100. The hub 309 has a hub body 310, as shown in FIG. 27. The hub body 310, which longitudinal direction is parallel to the directions as shown by the arrows ZA and ZB, is formed in the shape of a cylinder which axis center is the axis center ZQ1. The outside diameter is an outside diameter ZL1 on the arrow ZB side and an outside diameter ZL1' which is smaller than the outside diameter ZL1 on the arrow ZA side. That is, the hub body 310 is formed in the shape of a cylinder having a cavernous portion 310g by difference of the outside diameter. A hub stop groove 310c is formed on the outer peripheral face 310f side of the portion of the outside diameter ZL1 of the hub body 310. The hub stop groove 310c is annularly formed along the outer peripheral face 310f.

An engagement holding pillar portion 311 having an outside diameter ZL2 being smaller than the outside diameter ZL1', extending in the directions as shown by the arrows ZA and ZB, is provided being united and coaxial with the hub body 310 on an end face 310a side of the arrow ZA side of the hub body 310 (that is, the arrow ZA side of the portion of the outside diameter ZL1' of the hub body 310).

The hub 309 is provided such that the portion of the outside diameter ZL1 of he hub body 310 is inserted into the hub insertion hole 307b of the hub insertion portion 307, and the portion of the outside diameter ZL1' of the hub body 310 and the engagement holding pillar portion 311 project outside of the opening end 307g, that is, on the arrow ZA side. The hub stop rib 307d of the hub insertion portion 307 and the hub stop groove 310c of the hub 309 are at the positions corresponding to and adjusting to each other, and then the hub stop rib 307d is engaged with the hub stop groove 310c inserting the top end side on the arrow ZD side thereof into the hub stop groove 310c which is at the position corresponding and adjusting to one of the hub stop rib 307d.

Since the width of the hub stop rib 307d in the directions as shown by the arrows ZA and ZB is broader than one of the hub stop groove 310c in the directions as shown by the arrows ZA and ZB, as shown in FIG. 27, the hub stop rib 307d is engaged with the hub stop groove 310c abutting on opening ends 310e, 310e of both sides of the arrows ZA and ZB of the hub stop groove 310c in seal portions 307e, 307e on the sides of the arrows ZA and ZB of the top thereof.

The inner peripheral face 307a of the hub insertion portion 307 is not in contact with the outer peripheral face 310f of the hub 309 in the portions excluding the hub stop rib 307d, and a gap space 312 is formed bewteen the inner peripheral face 307a and the outer peripheral face 310f. That is, since contact between the inner peripheral face 307a side of the hub insertion portion 307 and the hub 309 is executed only between the hub stop rib 307d and the outer peripheral face 310f side of the hub 309, when the hub 309 is inserted into the syringe Z100, the hub 309 can be easily inserted into the hub insertion portion 307. In addition, in case of the operation of storing a needle, described hereinafter, the hub 309 is easily pulled out of the hub insertion portion 307 (As long as insertion of the hub 309 into the hub insertion portion 307 and pulling of the hub 309 out of the hub insertion portion 307 can be easily executed, the portions excluding the hub stop 307d of the inner peripheral face 307a of the hub insertion portion 307 may be in contact with the outer peripheral face 310f of the hub 309.).

An end face 310b of the arrow ZB side of the hub body 310 is positioned on the arrow ZA side rather than the boundary between the hub insertion hole 307b and the inside space 302a (that is, the boundary between the inside of the hub insertion portion 307 and the inside of the taper 306), and the space of the inside of the hub insertion hole 307b on the arrow ZB side rather than the end face 310b is a hole space 307h.

On the other hand, the hub insertion portion 307 is elastically deformed expanding in the direction as shown by an arrow ZC in such a state that the hub 309 is provided with the hub insertion hole 307b. That is, the restoring force by elastic deformation of the hub insertion portion 307 is transferred to the hub 309 through the hub stop rib 307d of the hub insertion portion 307. That is, predetermined seal pressures by the restoring force are respectively acted between the hub stop rib 307d and the hub 309 in the portions between the seal portion 307e and an opening end 310e of the hub stop groove 310c in which both abut on each other, and then, the portion between the seal portion 307e and the opening end 310e is in a water tight state or an air tight state.

As shown in FIG. 27, a needle insertion hole 313 is provided with the hub 309. The needle insertion hole 313 is provided forming a circular opening 313a, which center is the axis ceter ZQ1, at an end face 311a of the arrow ZA side of the engagement holding pillar portion 311 of the hub 309, extending from the end face 311a in the direction as shown by the arrow ZB. An end portion 313b of the arrow ZB side of the needle insertion hole 313 reaches the inside of the hub body 310 and the end portion 313b is in contact with a wall face 310d of the hub body 310. In the needle insertion hole 313, tapers are adequately formed such that the diameter of the needle insertion hole 313 is made narrower for the direction as shown by the arrow ZB.

On the other hand, a flow hole 313c is provided with the hub body 310 adjacent to the arrow ZB side of the needle insertion hole 313 (right side of the paper of FIG. 27). The flow hole 313c is cylindrically formed such that its center is the axis center ZQ1 and its diameter is smaller than one of the end portion 313b of the needle insertion hole 313. The flow hole 313c is provided forming a circular opening at the wall face 310d of the hub body 310, communicating with the needle insertion hole 313.

A piston engagement hole 315, which section perpendicular to the axis center ZQ1 is a circle, is provided with the hub body 310, communicating with and being adjacent to the arrow ZB side of the flow hole 313c, coaxial with the axis center ZQ1. The arrow ZB side of the piston engagement hole 315 is open outside in the end face 310b of the hub body 310.

The piston engagement hole 315 is comprised of two parts, an engagement holding portion 316 of the arrow ZA side and an introducing portion 317 of the arrow ZB side. The engagement holding portion 316 is almost cylindrical shape, coaxial with the axis center ZQ1, and both end portion sides of the arrows ZA and ZB thereof are taperingly formed such that each diameter is made narrower for the direction as shown by the arrow ZA or arrow ZB. The end portion side of the arrow ZA side of the engagement holding portion 316 is communicated and connected with the flow hole 313c.

The introducing portion 317 communicates with and is adjacent to the end portion of the arrow ZB side of the engagement holding portion 316. The diameter of the introducing portion 317 is made bigger for the direction as shown by the arrow ZB. Then, the portion sandwitched between a wall face 316a facing the engagement holding portion 316 and a wall face 317a facing the introducing portion 317 of the hub body 310 forms a projection 320 projecting for the axis center ZQ1 with a boundary portion 319 between the engagement holding portion 316 and the introducing portion 317 as an apex.

On the other hand, as shown in FIG. 27, the needle 321 of the needle assembly unit 360 is inserted into the needle insertion hole 313 of the hub 309. The needle 321 is inserted from the rear end portion side thereof into the needle insertion hole 313 and the top end side is positioned outside of the syringe body 302. The rear end of the needle 321 abuts on the wall face 310d formed on the arrow ZB side of the needle insertion hole 313. A medium flow hole 321a provided penetrating from the top end to the rear end side of the needle 321 and the flow hole 313c are adjacent to and communicate with each other in the directions as shown by the arrows ZA and ZB.

An adhesive 322 is injected into the needle insertion hole 313 filling between the needle 321 and the hub 309 and is hardened.

As shown in FIG. 27, the hub fixed member 361 of the needle assembly unit 360 has a fixed member body 361a capable of enclosing the opening end 307g of the hub insertion portion 307 and enclosing the portion near the opening end 307g of the hub insertion portion 307 from the outer peripheral face 307f side of the hub insertion portion 307. The fixed member body 361a is comprised of a reaction wall portion 361d facing the opening end 307g of the hub insertion portion 307 and perpendicular in the directions as shown by the arrows ZA and ZB, a cylindrical portion 361e cylindrically formed enclosing the outer peripheral face 307f side of the hub insertion portion 307, and a communicating portion 361f communicating between the reaction wall portion 361d and the cylindrical portion 361e. A hub engagement hole 362 penetrating the reaction wall portion 361d in the directions as shown by the arrows ZA and ZB is provided with the reaction wall portion 361d. The communicating portion 361f is taperingly formed such that the inside and outside diameters are reduced for the direction as shown by the arrow ZA.

That is, the hub fixed member 361 is installed on the hub insertion portion 307 inserting the portion near the opening end 307g side of the hub insertion portion 307 into a syringe insertion hole 361c which is inside of the cylindrical portion 361e, and is engaged with the hub 309 penetrating the engagement holding pillar portion 311 of the hub 309 in the hub engagement hole 362 formed at the reaction wall portion 361d.

In such a state that the engagement holding pillar portion 311 penetrates the hub engagement hole 362, the fixed member body 361a and the engagement holding pillar portion 311 stress each other in the directions as shown by the arrows ZC and ZD in the hub engagement hole 362. By the force of this stress, a predetermined frictional force in the directions as shown by the arrows ZA and ZB can be relatively acted in the contact portion between the fixed member body 361a and the engagement holding pillar portion 311 in the hub engagement hole 362 between both 361a and 311.

On the other hand, a syringe engagement projection 363 is annularly formed protecting along the inner peripheral face 361b on an inner peripheral face 361b side of the cylindrical portion 361e of the fixed member body 361a. The position formed the syringe engagement projection 363 corresponds and adjusts to one of the hub fixed member engagement groove 307c of the hub insertion portion 307. Therefore, in such a state that the fixed member body 361a is installed on the hub insertion portion 307, the position of the syringe engagement projection 363 and the position of the hub fixed member engagement groove 307c are corresponded and adjusted to each other. The syringe engagement projection 363 is in a state of being inserted into and engaged with the hub fixed member engagement groove 307c. That is, the hub fixed member 361 is installed in the hub insertion portion 307 engaging the syringe engagement projection 363 and the hub fixed member engagement groove 307c with each other.

The side portion 363b, which is the portion of the arrow ZB side of an apex portion 363a positioned the nearest position to the arrow ZD side of the syringe engagement projection 363, is formed gradually inclining in the direction by the arrow ZC for the direction as shown by the arrow ZB. Then, when the hub fixed member 361 is installed in the hub insertion portion 307 by pressing in the direction as shown by the arrow ZB, the side portion 363b receives a force in the direction as shown by the arrow ZC from the opening end 307g of the hub insertion portion 307 abutting on the side portion 363b and the like. Therefore, the cylindrical portion 361e is effectively expanded in the direction as shown by the arrow ZC, thereby the hub fixed member 361 can be smoothly installed in the hub insertion portion 307.

A side portion 363c which is the portion on the arrow ZA side of the apex portion 363a of the syringe engagement projection 363 is formed in a predetermined shape (in the shape of a wall face perpendicular to the directions as shown by the arrows ZA and ZB in FIG. 27). Then, in such a state that the syringe engagement projection 363 and the hub fixed member engagement groove 307c are engaged with each other, the side portion 363c and the hub insertion portion 307 can add a force only in the directions as shown by the arrows ZA and ZB to each other in the portion where the both 363c and 307 are abutted on each other, in the hub fixed member engagement groove 307c. That is, after the syringe engagement projection 363 and the hub fixed member engagement groove 307c are engaged with each other, even if the hub fixed member 361 is pulled to the syringe Z100 in the direction as shown by the arrow ZA, the fixed member body 361a receives a reaction only in the direction as shown by the arrow ZB from the syringe Z100 through the syringe engagement projection 363. Therefore, since the cylindrical portion 361e is not expanded in the direction as shown by the arrow ZC, the engagement between the syringe engagement projection 363 and the hub fixed member engagement groove 307c is not disengaged.

The needle assembly unit 360 is comprised of the hub 309, the needle 321 and the hub fixed member 361, as described heretofore. The needle assembly unit 360 is connected with the syringe Z100 such that the hub 309 connected the needle 321 therewith is provided with the hub insertion hole 307b and the hub fixed member 361 engaged the hub 309 therewith is installed in the hub insertion portion 307.

The piston 323 is provided with the syringe assembly 301, as shown in FIG. 28 (FIG. 28 is a typical sectional view of the syringe assembly 301, but with respect to a piston body 325, an outer press plate 327, an inner press plate 329, a packing support 330, a hub engagement portion 331, referred hereinafter, of the piston 323, their sides are shown, not their sections, for convenience.)

The piston 323 has the bar-shaped piston body 325 extending in the directions as shown by the arrows ZA and ZB. The piston body 325 is comprised such that two congruent plate portions 325a, each which is a plate shaped rectangle especially long in the directions as shown by the arrows ZA and ZB, are unitedly cross provided with each other such that the sections thereof form the shape of a cross. The width perpendicular to the directions as shown by the arrows ZA and ZB of the plate face of the plate portion 325a is almost equal to the inside diameter in the engagement rib 303b of the main cylindrical portion 303, and the piston body 325 is inserted into the main cylindrical portion 303 through the opening end 303a from the arrow ZA side of the piston body 325.

On each plate portion 325a of the piston body 325, notches 326 are formed from both side portions of the respective plate portions 325a, 325a in the direction of the axis center (that is, the axis center ZQ1) of the piston body 325 in the shape of a wedge near the direction as shown by the arrow ZA. Four notches 326 are provided at the positions adjusted one another in the directions as shown by the arrows ZA and ZB.

The outer press plate 327 in the shape of a circular plate, which plate face is perpendicular to the directions as shown by the arrows ZA and ZB, is provided united with the piston body 325 on the end portion side of the arrow ZB side of the piston body 325.

The inner press plate 329 in the shape of a circular plate, which plate face is perpendicular to the directions as shown by the arrows ZA and ZB, is provided united and coaxial with the piston body 325 on the end portion side of the arrow ZA side of the piston body 325 (Therefore, the inner press plate 329 is positioned inside of the main cylindrical portion 303.), and the diameter of the inner press plate 329 is almost equal to the inside diameter of the main cylindrical portion 303 (Therefore, the diameter of the inner press plate 329 is bigger than the inside diameter in the engagement rib 303b of the main cylindrical portion 303.).

As shown in FIG. 27, the packing support 330 is provided with the inner press plate 329 on the arrow ZA side thereof. A pillar portion 330a in the shape of a cylinder, extending in the directions as shown by the arrows ZA and ZB, is provided with the packing support 330, being coaxial with the inner press plate 329. The diameter of the pillar portion 330a is smaller than one of the inner press plate 329. The pillar portion 330a is provided on the arrow ZA side of the inner press plate 329, being united with the inner press plate 329. As shown in FIG. 27, an insertion pillar portion 330b in the shape of a cylinder, extending in the directions as shown by the arrows ZA and ZB being coaxial with the pillar portion 330a, having an outside diameter almost equal to the inside diameter of the hub insertion portion 307, is provided on the arrow ZA side of the pillar portion 330a, being united with the pillar portion 330a.

The hub engagement portion 331 is provided on the arrow ZA side of the insertion pillar portion 330b. A pillar portion 331a in the shape of a cylinder, extending in the directions as shown by the arrows ZA and ZB, is provided with the hub engagement portion 331, being coaxial with the insertion pillar portion 330b. The diameter of the pillar portion 331a is smaller than one of the insertion pillar portion 330b. The pillar portion 331a is provided on the arrow ZA side of the insertion pillar portion 330b, being united with the insertion pillar portion 330b. An insertion portion 331b in the shape of a hemi-sphere, which diameter is bigger than one of the pillar portion 331a, is provided on the arrow ZA side of the pillar portion 331a, being united with the pillar portion 331a facing an spherical face 331c side to the arrow ZA side. A plurality of grooves 332 in the shape of a stripe are provided with the insertion portion 331b, being parallel to the spherical face 331c, extending from the top portion of the arrow ZA side to the arrow ZB side.

The diameter of the pillar portion 331a is almost equal to the inside diameter in the boundary portion 319 of the piston engagement hole 315 provided with the hub 309. Therefore, the diameter of the insertion portion 331b is bigger than one of the boundary portion 319. The side of the insertion portion 331b allows to be sufficiently inserted into and to be held by the engagement holding portion 316 of the piston engagement hole 315.

On the other hand, as shown in FIG. 27, a packing 333 made of flexible resin, is supported with the packing support 330. The packing 333 has a packing body 335 which is inserted into inside of the main cylindrical portion 303 of the syringe Z100 so as to adjust. An engagement hole 335a penetrating the packing body 335 in the directions as shown by the arrows ZA and ZB is provided with the packing body 335. The pillar portion 330a of the packing support 330 and a part of the insertion pillar portion 330b penetrate the engagement hole 335a. That is, the packing 333 engages with the packing support 330 such that the packing support 330 penetrates the engagement hole 335a, thereby the packing 333 is supported by the packing support 330. A supporting face 335h, perpendicular to the directions as shown by the arrows ZA and ZB, is formed at the end portion of the arrow ZB side of the packing body 335. The supporting face 335h abuts on the inner press plate 329 so as to easily receive a force in the direction as shown by the arrow ZA by the inner press plate 329. The packing 333 and the pillar portion 330a in the engagement hole 335a are closely contacted with each other, and the portion therebetween is sealed against water or against air.

A hollow clearance space 335f is formed inside of the packing body 335, enclosing the engagement hole 335a from the arrow ZC side and being adjacent to and communicating with the engagement hole 335a (Therefore, the clearance space 335f is enclosed by the packing body 335 on the arrows ZA, ZB and ZC sides thereof, and is contacted with the insertion pillar portion 330b of the packing support 330 on the arrow ZD side thereof.). The packing 323 and the insertion pillar portion 330b are contacted with each other in the portion of the arrow ZA side rather than the clearance space 335f, of the engagement hole 335a, but both are not closely contacted with each other, that is, the portion therebetween is not sealed against water or against air. That is, air or liquid can flow between the clearance space 335f and the outside of the arrow ZA side of the packing body 335 through the engagement hole 335a.

The arrow ZA side of the packing body 335 is a taper 335b. While the form of the inside of the taper 306 of the syringe body 302 is a taper, reducing the inside diameter at a predetermined rate K1 for the direction as shown by the arrow ZA, as described before, the form of the taper 335b in a natural state is a taper, reducing the outside diameter at a predetermined rate K2, which is bigger than a predetermined rate K1. That is, the taper 335b is formed forming a remaining space 351 between a surface 335e excluding the end portion 335d of the taper 335b (that is, liquid pressing face capable of pressing the injection medium) and the inner peripheral face 306a of the taper 306 when an end portion 335d of the arrow ZB side of the taper 335b in a natural state abuts on an inner peripheral face 306a of the taper 306 inside of the taper 306.

A part of the arrow ZA side of the insertion pillar portion 330b of the packing support 330 penetrating the engagement hole 335a further projects on the arrow ZA side rather than the taper 335b.

In such a state that the end portion 335d of the taper 335b is abutted on the inside of the taper 306 of the syringe body 302 when the taper 335b of the packing 333 is in a natural state, as shown in FIG. 27, the insertion pillar portion 330b of the packing support 330 engaging with the packing 333 is inserted into the hub insertion hole 307b of the syringe body 302. The form of the packing 333 is set so as to become such a state that the spherical face 331c of the insertion portion 331b of the hub engagement portion 331 contacts with the wall face 317a facing the introducing portion 317 of the piston engagement hole 315.

The outside diameter of the packing body 335 of the packing 333 is almost equal to one of the inner press plate 329. However, on the outer peripheral side of the packing body 335, annular folds 335c are double formed along the outer periphery of the packing body 335 arranging in a line in the directions as shown by the arrows ZA and ZB. Therefore, the packing 333 is inserted into the main cylindrical portion 303 of the syringe body 302, reducing the portion near the fold 335c of the packing body 335 in the direction for the axis center ZQ1, that is, in the direction as shown by the arrow ZD by elastic deformation. That is, the packing 333 and the main cylindrical portion 303 are closely contacted with each other in the folds 335c and the inner peripheral face 303c, and the portion between the packing 333 and the main cylindrical portion 303 is sealed against water or against air.

The outer peripheral side of the packing body 335, that is, the surface of the side where the folds 335c and the like are formed is a sliding face 335g facing the inner peripheral face 303c of the syringe body 302. The packing 333 contacts with the inner peripheral face 303c in the sliding face 335g. Since the inner peripheral face 303c and the sliding face 335g are smoothly formed, the piston 323 inserted the packing 333 therein is free to slide and move in the directions as shown by the arrows ZA and ZB in the inside space 302a of the main cylindrical portion 303.

The syringe assembly 301 just before an injection action, or in such a state that the needle 321 and the syringe Z100 are connected with each other, is comprised, as described heretofore.

The syringe assembly 301 in the state of being stored, that is, in such a state that the needle 321 and the syringe Z100 are not yet connected with each other, is as follows.

That is, the syringe assembly 301 in the state of being stored has the syringe Z100. The piston 323 is provided with the syringe Z100 in such a state that it is inserted into the inside space 302a of the syringe body. In addition, the syringe assembly 301 in the state of being stored has the needle assembly unit 360 in the state of being separated from the syringe Z100 (in the state of not being connected).

Figure 29:
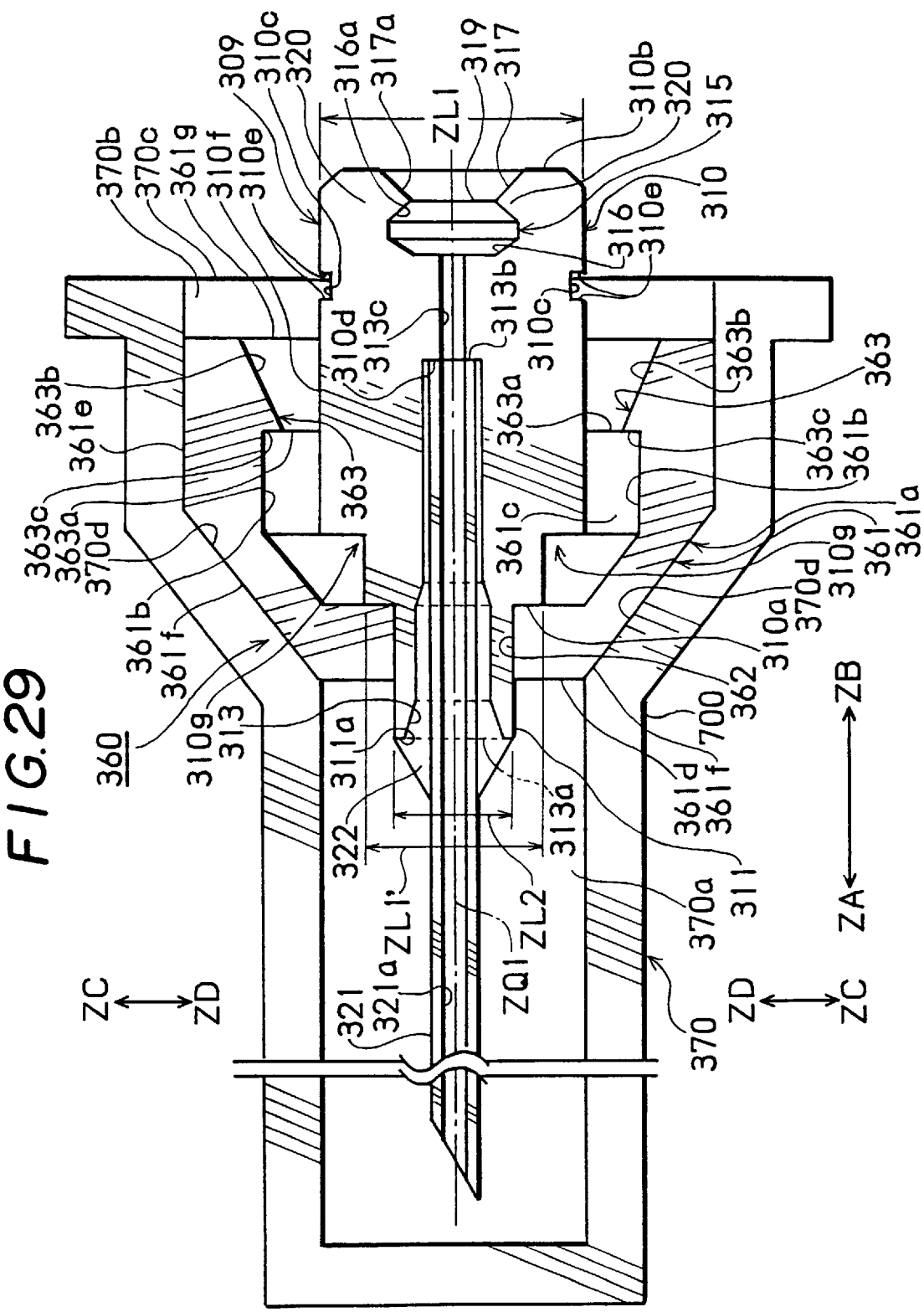
FIG. 29 is a view showing a state in which a cap for storing is installed on the needle assembly unit as shown in FIG. 27.

In the syringe assembly 301 in the state of being stored, a cap for storing 370 is installed on the needle assembly unit 360, as shown in FIG. 29.

The cap for storing 370 has a cap body 700 cylindrically formed, extending in the directions as shown by the arrows ZA and ZB. An end portion side of the arrow ZA side of the cap body 700 is closed, and an end portion side of the arrow ZB side of the cap body 700 is open. Inside of the cap body 700, a cylindrical needle keeping space 370a is provided extending from the end portion side of the arrow ZA side for the direction as shown by the arrow ZB. On the arrow ZB side of the needle keeping space 370a, a fixed member insertion space 370b capable of inserting the fixed member body 361a of the needle assembly unit 360 therein is provided connecting with the needle keeping space 370a. The end portion of the arrow ZB side of the fixed member insertion space 370b is open outside forming an opening 370c at the cap body 700. The opening 370c is open on the end portion side of the arrow ZB side of the cap body 700, as described heretofore.

The cap for storing 370 as described heretofore is installed on the needle assembly unit 360 inserting the top end side of the needle 321 into the needle keeping space 370a of the cap for storing 370 and inserting the fixed member body 361a into the fixed member insertion space 370b of the cap for storing 370.

In such a state that the cap for storing 370 is installed, the cap body 700 and the fixed member body 361a in the fixed member insertion space 370b are fixed and closely contacted with each other in such a manner that a predetermined pressure is added in the directions as shown by the arrows ZC and ZD. The top end of the needle 321 is not in contact with the cap body 700 in the needle keeping space 370a.

Since the fixed member insertion space 370b is formed in the shape corresponding to the fixed member body 361a, the communicating portion 361f of the fixed member body 361a in the state of being inserted into the fixed member insertion space 370b abuts on an abutting surface 370d corresponding to the communicating portion 361f of the surface on the fixed member insertion space 370b side of the cap body 700.

The syringe assembly 301 in the state of being stored, or in such a state that the needle 321 and the syringe Z100 are not yet connected with each other, is comprised as described heretofore.

As explained before, the hub 309 and the hub fixed member 361 are fixed since the engagement holding pillar portion 311 engages with the hub engagement hole 362 so as to penetrate. Since the cap body 700 and the hub fixed member 361 are fixed, as described heretofore, the hub 309, the hub fixed member 361 and the cap for storing 370 are all fixed. That is, the hub 309 and the hub fixed member 361 are installed in the cap for storing 370 in the syringe assembly 301 in the state of being stored, such that the needle 321 is stored in and inserted into the cap for storing 370, and the hub 309, the hub fixed member 361 and the cap for storing 370 are not separated from one another even by inadvertence. Therefore, storing maintenance of the needle assembly unit 360 can be safely executed.

Since the syringe assembly 301 just before injection action and the syringe assembly 301 in the state of being stored are respectively comprised, as described before, and then the syringe assembly 301 in the state of being stored just before injection action, that is, in the state of use is used and, after that, the syringe assembly 301 is discarded as follows.

At first, an injection actor (not shown) elects the needle assembly unit 360, installed the cap for storing 370 thereon, installed the needle 321 having length and diameter suitable for injection therein, of the syringe assemblies 301 in the state of being stored, and connects it with the syringe Z100 inserted the piston 323 therein. In case of connection, after the end face 310b side of the hub 309 of the needle assembly unit 360 and the arrow ZB side of the syringe insertion hole 361c of the hub fixed member 361, that is, an opening end 361g are adjusted to the opening end 307g of the hub insertion portion 307, the needle assembly unit 360 is pressed with the cap for storing 370 on the syringe Z100, that is, in the direction as shown by the arrow ZB. Since the abutting face 370d inside the cap for storing 370 and the communicating portion 361f of the hub fixed member 361 are abutted on each other such that a stress can be added to one by the other in the directions as shown by the arrows ZA and ZB, and the reaction wall portion 361d of the hub fixed member 361 and the end face 310a of the hub 309 are abutted on each other (or approach each other) such that a stress can be added to one by the other in the directions as shown by the arrows ZA and ZB, the hub fixed member 361 and the hub 309 are pressed in the direction as shown by the arrow ZB through the cap for storing 370 when the cap for storing 370 is pressed in the direction as shown by the arrow ZB.

Since the outside diameter ZL1 of the hub body 310 is smaller than the inside diameter of the hub insertion portion 307 including the opening end 307g, the hub body 310 is inserted in the hub insertion hole 307b in the direction as shown by the arrow ZB. By further continuing the insertion, the outer peripheral side of the hub body 310 abuts on the hub stop rib 307d inside of the hub insertion portion 307. Since the inside diameter of the hub insertion portion 307 in the portion of the hub stop rib 307d is smaller than the outside diameter of the hub body, the side portion of the arrow ZA side of the hub stop rib 307d is abutted on the hub body. However, since the section of the hub stop rib 307d is formed in the shape of an arc, pressing pressure force is added by the portion near the end face of the hub body to the side portion, the pressing pressure force acts so as to be a force expanding and deforming the hub insertion portion 307 in the direction as shown by the arrow ZC on the basis of the arc shape of the section and then, the hub insertion portion 307 is expanded and deformed enlarging its inside diameter. The insertion is smoothly executed by expansion and deformation. By further continuting the insertion, the position of the hub stop rib 307d and the position of the hub stop groove 310c in the directions as shown by the arrows ZA and ZB are ajusted to each other. By adjustment, the hub stop rib 307d and the hub stop groove 310c are engaged with each other. The engagement means insertion of the hub 309 into the hub insertion portion 307.

The opening end 307g side of the hub insertion portion 307 is inserted into the syringe insertion hole 361c from the opening end 361g of the hub fixed member 361. Since the inside diameter of the cylindrical portion 361e of the fixed member body 361a is smaller than the outside diameter of the hub insertion portion 307 in the portion of the syringe engagement projection 363, the portion near the opening end 307g of the hub insertion portion 307 abuts on the side face 363b of the syringe engagement projection 363. Since the side portion 363b is formed gradually inclining in the direction as shown by the arrow ZC for the direction as shown by the arrow ZB, as described before, however, the side portion 363b receives a force in the direction as shown by the arrow ZC from the opening end 307g of the hub insertion portion 307 abutting on the side portion 363b and the like. That is, since the cylindrical portion 361e is effectively expanded in the direction as shown by the arrow ZC by this force in the direction as shown by the arrow ZC, the hub insertion portion 307 is smoothly inserted into the hub fixed member 361. By further pressing the hub fixed member 361, the hub insertion portion 307 is further inserted into the syringe insertion hole 361c, and the position of the syringe engagement projection 363 and the position of the hub fixed member engagement groove 307c of the hub insertion portion 307 in the directions as shown by the arrows ZA and ZB are adjusted to each other. By adjustment, the syringe engagement projection 363 and the hub fixed member engagement groove 307c are engaged with each other. This engagement means installation of the hub fixed member 361 in the syringe Z100.

As described heretofore, the hub 309 is inserted into the hub insertion portion 307 and the hub fixed member 361 is installed in the syringe Z100, thereby the needle assembly unit 360 is connected with the syringe Z100.

After connection, the syringe Z100 side is fixed and the cap for storing 370 is taken away in the direction as shown by the arrow ZA. On this occasion, a frictional force against a predetermined pressure acts between the cap body 700 and the fixed member body 361a in the directions as shown by the arrows ZA and ZB so as to keep the both 700 and 361a. However, since the fixed member body 361a and the syringe Z100 are fixed through the syringe engagement projection 363, as described heretofore, only the cap for storing 370 is taken away being out of the hub fixed member 361. In this way, the syringe assembly 301 becomes to be such a state that the needle 321 and the syringe Z100 are connected with each other, that is, the state just before use.

Subsequently, this syringe assembly 301 is used. That is, the needle 321 of the syringe assembly 301 is advanced into an injection medium 352 in a medicine bottle (not shown), the piston 323 is pulled in the direction as shown by the arrow ZB with respect to the syringe body 302, and by differential pressure, the injection medium 352 in the medicine bottle is streamed to a medium holding space 353 on the the needle 321 side rather than the piston 323, of the hole space 307h of the hub insertion portion 307 and the inside space 302a of the syringe body 302 passing through the medium flow hole 321a of the needle 321, the flow hole 313c of the hub 309 and the piston engagement hole 315 so as to fill the syringe assembly 301 with the injection medium 352.

In case of filling of the injection medium 352, a differential pressure force in the direction as shown by the arrow ZB by differential pressure between the outside and the medium holding space 353 acts on the hub 309. However, the restoring force in the direction as shown by the arrow ZD which the hub insertion portion 307 has is set as a predetermined size as described heretofore, thereby sealing between each seal portion 307e and each opening end 310e of the arrow ZA side and the arrow ZB side is not disengaged between the hub 309 and the hub insertion portion 307 against the maximum differential pressure force predicted.

After filling of the injection medium 352, the needle 321 of the syringe assembly 301 is stuck into an injection portion of a patient (not shown).

Subsequently, the outer press plate 327 of the piston 323 is pressed in the direction as shown by the arrow ZA so as to drive the piston 323 with respect to the syringe body 302 in the direction as shown by the arrow ZA. The injection medium 352 of the medium holding space 353 is pressurized so as to flow into the body in the injection portion of a patient (not shown) through the piston engagement hole 315 of the hub 309, the flow hole 313c, the medium flow hole 321a of the needle 321.

On this occasion, the injection medium 352 is pressurized and an action force by the pressure of the injection medium 352 is added to the hub 309 in the direction as shown by the arrow ZA from the end face 310b side of the hub 309 adjacent to the injection medium 352. However, the restoring force in the direction as shown by the arrow ZD which the hub insertion portion 307 has is set in such a predetermined size as described heretofore, thereby sealing between each seal portion 307e and each opening end 310e on the arrow ZA side and the arrow ZB side is not disengaged between the hub insertion portion 307 and the hub 309 against the maximum action force predicted.

After a predetermined amount of the injection medium 352 is flowed into the body in the injection portion of a patient, that is, after the piston 323 is driven to the position where the end portion 335d of the taper 335b of the packing 333 is abutted on the inside of the taper 306 of the syringe body 302, and as shown in FIG. 27, the insertion portion 331b of the hub engagement portion 331 of the piston 323 abuts on the wall face 317a in the introducing hole 317 of the piston engagement hole 315 of the hub 309, that is, to an injection end position ZP2 in the figure, the whole syringe assembly 301 is pulled in the direction as shown by the arrow ZB to a patient (not shown), and the needle 321 is pulled out of the injection portion of a patient.

After the needle 321 is pulled out, the operation of storing the needle is executed as follows.

In the operation of storing the needle, the engagement operation between the piston 323 and the hub 309 is executed as follows.

That is, the outer press plate 327 of the piston 323 is further pressed with fingers in the direction as shown by the arrow ZA so as to press the piston body 325 in the direction as shown by the arrow ZA, and then the insertion pillar portion 330b of the packing support 330 and the hub engagement portion 331 are fed in the direction as shown by the arrow ZA in the hub insertion hole 307b.

Just before start of the operation of storing the needle, the piston 323 is positioned such that the taper 335b in a natural state is positioned corresponding to the inside of the taper 306, the end portion 335d of the arrow ZB side of the taper 335b abuts on the inner peripheral face 306a of the taper 306, and a remaining space 351 is formed between the surface 335e excluding the end portion 335d of the taper 335b and the inner peripheral face 306a of the taper 306. Therefore, by pressing pressure in the direction as shown by the arrow ZA of the piston body 325, in the packing 333, the portion on the arrow ZB side from the portion near the end portion 335d abutting on the taper 306 is compressed in the directions as shown by the arrows ZB and ZD, and the other portion is pressed out in the direction as shown by the arrow ZA making use of the remaining space 351 in such a manner that the surface 335e approaches the taper 306. Therefore, since the quantity of elastic compression in the packing 333 is extremely reduced by the remaining space 351, the piston 323 can be operated with extremely small force.

In addition, since the clearance space 335f is formed inside of the packing body 335, the clearance space 335f is also reduced with the packing body 335 when the packing body 335 is elastically compressed. Therefore, since the quantity of elastic compression in the packing 333 is reduced by the clearance space 335f, the piston 323 can be operated with extremely small force.

As shown in FIG. 27, just before start of the operation of storing the needle, the hole space 307h between the end face 310b of the hub 309 and the insertion pillar portion 330b of the piston 323 side (that is, the medium holding space 353) and the remaining space 351 (that is, the medium holding space 353) are filled with the remaining injection medium 352. The operation of storing the needle is started, the piston 323 is pressed and moved in the direction as shown by the arrow ZA as described heretofore, thereby the remaining injection medium 352 is pressurized. However, a plurality of grooves 332 are provided with the insertion portion 331b, as described heretofore, and then these grooves 332 are not closed when the insertion portion 331b and the wall face 317a are abutted on each other by pressing. Therefore, when the insertion portion 331b and the wall face 317a are abutted on each other by pressing, the hole space 307h or the remaining space 351 side and the engagement holding portion 316 side communicate with the grooves 332. The remaining injection medium 352 pressurized of the hole space 307h or the remaining space 351 flows to the engagement holding portion 316 side through these grooves 332

(This is because the injection medium 352 of the remaining space 351 can flow to the hole space 307h side passing between the insertion pillar portion 330b and the hub insertion portion 307 since the portion between the insertion pillar portion 330b and the hub insertion portion 307 is not water tight.), and furthermore, is expelled outside through the flow hole 313c and the medium flow hole 321a of the needle 321. That is, when the operation of storing the needle starts and the piston 323 is pressed and moved in the direction as shown by the arrow ZA, the remaining injection medium 352 pressurized in the hole space 307h or the remaining space 351 is appropriately expelled outside, and the pressure is not extremely increased. Therefore, the resistance by pressure of remaining injection medium 352 is not extremely acted on the piston 323, and then the piston 323 is pressed and moved in the direction as shown by the arrow ZA with extremely small force.

While the packing 333 is elastically reduced, the insertion pillar portion 330b of the packing support 330 and the hub engagement portion 331 are pressed and moved in the direction as shown by the arrow ZA in the hub insertion portion 307b, and the insertion portion 331b of the hub engagement portion 331 is pressed and moved in the direction as shown by the arrow ZA from the introducing portion 317 of the piston engagement hole 315 for the engagement holding portion 316.

That is, the piston 323 is pressed and moved in the direction as shown by the arrow ZA, thereby the insertion portion 331b is pressed to the wall face 317a in the introducing portion 317. However, the arrow ZA side of the insertion portion 331b is the spherical face 331c, then the insertion portion 331b is formed in such a manner that the section perpendicular to an axis center ZQ1 is reduced for the direction as shown by the arrow ZA. Then, the insertion portion 331b is pressed to the wall face 317a in this spherical face 331c. In addition, the introducing portion 317 is taperingly formed reducing the inside thereof for the direction as shown by the arrow ZA. Therefore, the insertion portion 331b is pressed in the direction as shown by the arrow ZA in the introducing portion 317, thereby stress by pressing pressure respectively acting between the insertion portion 331b and the projection 320 forming the wall face 317a respectively effectively acts in such a manner that for the insertion portion 331b the cross section perpendicular to the axis center ZQ1 is elastically reduced, and for the projection 320, the inside of the introducing portion 317 is elastically enlarged in the direction as shown by the arrow ZC. As a result, the cross section perpendicular to the axis center ZQ1 of the insertion portion 331b is reduced and the inside of the introducing portion 317 is enlarged in the direction as shown by the arrow ZC, thereby the insertion portion 331b pressed in the direction as shown by the arrow ZA moves in the direction as shown by the arrow ZA in the introducing portion 317.

Furthermore, the piston 323 is pressed in the direction as shown by the arrow ZA so as to further move the insertion portion 331b in the direction as shown by the arrow ZA in the introducing portion 317. Therefore, the insertion portion 331b is moved on the engagement holding portion 316 side passing through the boundary portion 319 between the introducing portion 317 and the engagement holding portion 316 from the arrow ZA side thereof, and the insertion portion 331b is completely inserted into the engagement holding portion 316, thereby the pressing of the piston 323 is stopped. The insertion portion 331b is completely inserted into the engagement holding portion 316, thereby the hub engagement portion 331 and the piston engagement hole 315 are engaged with each other, and then the operation of engagement between the piston 323 and the hub 309 finishes.

On this occasion, a pressing pressure force in the direction as shown by the arrow ZA acts on the insertion portion 331b, thereby a pressing pressure force in the direction as shown by the arrow ZA also acts on the hub 309. However, the hub 309 is supported in the direction as shown by the arrow ZB with the hand supporting the syringe body 302 through the hub stop rib 307d of the hub insertion portion 307, through the syringe body 302. Even if the hub 309 is not supported through the hub stop rib 307d, it can be supported with a hand supporting the syringe body 302 in the direction as shown by the arrow ZB, being supported the end face 310a of the hub 309 with the reaction wall portion 361d of the hub fixed member 361 and being supported the hub fixed member 361 with the hub insertion portion 307 through the syringe engagement projection 363. This is because in such a state that the syringe engagement projection 363 and the hub fixed member engagement groove 307c are engaged with each other, as described before, the side portion 363c and the hub insertion portion 307 can add a force to each other only in the directions as shown by the arrows ZA and ZB in the portion where both 363c and 307 are abutted on each other in the hub fixed member engagement groove 307c. Therefore, if the hub fixed member 361 receives a pressing pressure force in the direction as shown by the arrow ZA by the hub 309 so as to pull to the syringe Z100 in the direction as shown by the arrow ZA, the fixed member body 361a receives a reaction only in the direction as shown by the arrow ZB from the syringe Z100 through the syringe engagement projection 363, and therefore, the cylindrical portion 361e is not expanded in the direction as shown by the arrow ZC, the syringe engagement projection 363 and the hub fixed member engagement groove 307c are not disengaged from each other, and then, a pressing pressure force by the hub 309 is completely transferred to the syringe Z100 through the hub fixed member 361.

Therefore, the hub 309 is not almost moved in the direction as shown by the arrow ZA and the like if receiving the pressing pressure force in the direction as shown by the arrow ZA, and the hub 309 is not pulled out of the hub insertion portion 307 in the direction as shown by the arrow ZA.

Subsequently, the piston 323 is pulled with respect to the syringe body 302 in the direction as shown by the arrow ZB with a predetermined pulling force. That is, an action force in the direction as shown by the arrow ZB by a predetermined pulling force acts on the piston 323 and the insertion portion 331b of the hub engagement portion 331. The restoring force in the direction as shown by the arrow ZD which a hub insertion portion 304 has is set in such a predetermined size as one described heretofore, thereby the sealing between each seal portion 307e and each opening end 310e on the arrow ZA side and on the arrow ZB side is disengaged between the hub 309 and the hub insertion portion 307 against the action force in the direction as shown by the arrow ZB by a predetermined pulling force. Therefore, the sealing between the hub stop rib 307d and the hub stop groove 310c is disengaged.

The hub fixed member 361 and the hub 309 are engaged with each other such that the engagement holding pillar portion 311 penetrates the hub fixed member 361. In addition, as described heretofore, a predetermined pressure in the directions as shown by the arrows ZC and ZD acts between the both 311 and 361, and by this pressure, a predetermined frictional force in the directions as shown by the arrows ZA and ZB acts between both 311 and 361 so as to keep the both 311 and 361. However, since a predetermined pulling force when the hub 309 is pulled out is one defeating the predetermined frictional force, the engagement holding pillar portion 311 and the hub fixed member 361 are disengaged from each other being pulled the engagement holding pillar portion 311 out of the hub fixed member 361.

The hub stop rib 307d and the hub stop groove 310c are disengaged from each other, the engagement holding pillar portion 311 and the hub fixed member 361 are disengaged from each other, and the hub 309 is further advanced in the direction as shown by the arrow ZB, and then the hub 309 is pulled until it is completely pulled out of the hub insertion hole 307b in the direction as shown by the arrow ZB.

On this occasion, since the gap space 312 is formed between the hub 309 and the hub insertion hole 307b, contact between the hub 309 and the hub insertion portion 307 is executed only through the hub stop rib 307d portion, and the pulling operation can be easily executed with a small force after the hub stop rib 307d and the hub stop groove 310c are disengaged from each other.

The piston 323 is further pulled in the direction as shown by the arrow ZB in such a manner that the needle 321 inserted and fixed on the arrow ZA side of the hub 309 is inserted into the hub insertion hole 307b in the direction as shown by the arrow ZB from the hub engagement hole 362 of the hub fixed member 361 and the opening end 307g of the hub insertion portion 307 and further inserted into the inside space 302a of the main cylindrical portion 303 in the direction as shown by the arrow ZB, and the top end of the needle 321 is completely inserted into the inside space 302a.

Figure 30:
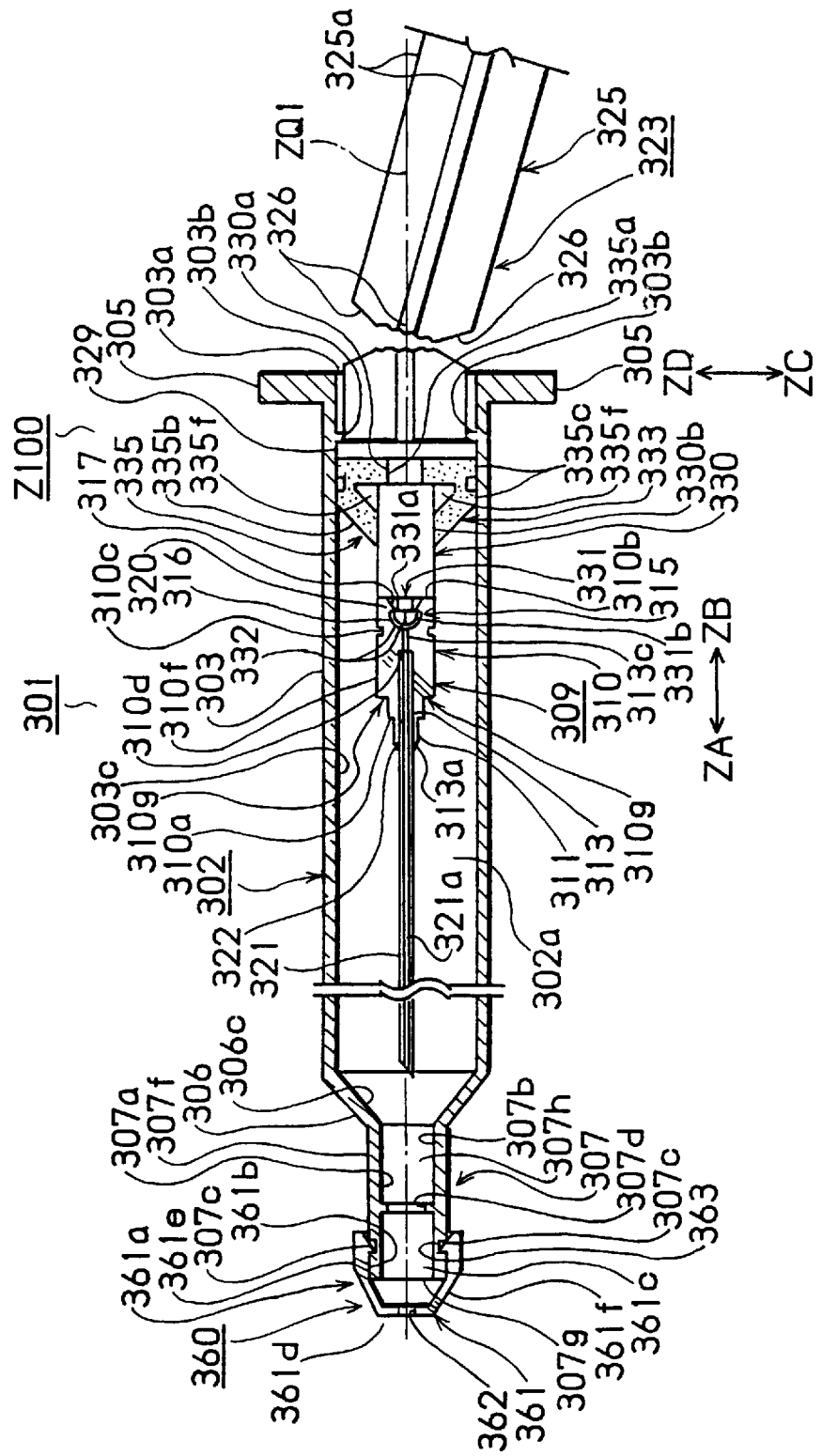
FIG. 30 is a view showing a way of bending and taking the piston in the syringe assembly as shown in FIG. 28.

As shown in FIG. 30, the piston 323 is further pulled until the inner press plate 329 abuts on the engagement rib 303b of the main cylindrical portion 303 of the syringe body 302, and then the piston 323 is stopped.

Then, the notch 326 of the piston body 325 is positioned near the opening end 303a of the syringe body 302. Subsequently, a force in the direction as shown by the arrow ZC is given to the piston 323. A force in the direction as shown by the arrow ZC is added on the piston 323 with respect to the syringe body 302, thereby the piston body 325 is bent in the notch 326 which structure is relatively weak against bending stress in the piston body 325, and the piston body 325 is divided into the arrow ZA side portion and the arrow ZB side portion forming a boundary by the notch 326.

Subsequently, the portion of the syringe body 302 side bent and taken and the portion of the outer press plate 327 of the piston 323 are disposed of so as to be discarded. Since the needle 321 is completely inserted and stored in the inside space 302a of the syringe body 302 being held with the top end portion of the piston 323 remaining in the inside space, there is no fear of hurting hands or the like and being secondarily infected from a wound by the needle 321. Therefore, waste disposal can be safely executed. As described before, the operation of storing the needle finishes and the use of the syringe assembly 301 and waste disposal after use all finish.

In the above-mentioned embodiment, the syringe engagement projection 363 formed in the shape of a projection is formed at the hub fixed member 361 of the needle assembly unit 360 as a syringe fixed means, and the hub fixed member engagement groove 307c formed in the shape of a groove is formed at the hub insertion portion 307 of the syringe Z100 as the reaction fixed member engagement means. However, as long as the syringe fixed means and the reaction fixed member engagement means may be formed such that both can be fixed and engaged with each other, any form of both is acceptable. For instance, the syringe fixed means may be formed in the shape of a groove, and the reaction fixed member engagement means may be formed in the shape of a projection. Alternatively, the syringe fixed means and the reaction fixed member engagement means may be formed in the shape of a screw so as to engage with each other.

The present invention has been explained on the basis of the embodiments presented herein. However, the embodiments which are described in the present specification are illustrative and not limiting. The scope of the invention is designated by the accompanying claims and is not restricted by the descriptions of the specific embodiments. Accordingly, all the transformations and changes belonging to the claims are included in the scope of the present invention.

I claim:

1. An occupying member for a syringe assembly comprising:
   a main body made of elastic material;
   a sliding face for the syringe formed at a periphery of said main body;
   a liquid pressing face formed at one end of said main body;
   a supporting face formed at the other end of said main body;
   a piston engagement insertion space extending into said main body from said supporting face; and
   a deformation accelerating space defined between said liquid pressing face and said supporting face and inside of said main body so as to enclose said piston engagement insertion space;
   whereby the deformation accelerating space reduces the force required to elastically compress the main body of the occupying member.

2. The occupying member as set forth in claim 1, wherein said deformation accelerating space is hollow.

3. The occupying member as set forth in claim 1, wherein said deformation accelerating space is filled with soft material being softer than said main body.

4. The occupying member as set forth in claim 1, wherein said piston engagement insertion space extends sufficiently into the main body so as to be in communication with said deformation accelerating space.

5. The occupying member as set forth in claim 1, wherein said liquid pressing face has a tapered portion.

6. The occupying member as set forth in claim 1, wherein said main body has an axial center, and wherein said supporting face has a plane perpendicular to the axial center of said main body.

7. An occupying member for a syringe assembly comprising:
   a main body made of elastic material;
   a sliding face for the syringe formed at a periphery of said main body;
   a liquid pressing face formed at one end of said main body;

a supporting face formed at the other end of said main body;

a piston engagement insertion space extending into said main body from said supporting face; and a deformation accelerating space defined between said liquid pressing face and said supporting face of said main body;

wherein said deformation accelerating space is cylindrically formed, wherein said piston engagement insertion space extends axially from said insertion space, and wherein said main body includes a periphery substantially enclosing said deformation accelerating space and said piston engagement insertion space;

whereby the deformation accelerating space reduces the force required to elastically compress the main body of the occupying member.

8. The occupying member as set forth in claim 7, wherein said deformation accelerating space is hollow.

9. The occupying member as set forth in claim 7, wherein said deformation accelerating space is filled with soft material being softer than said main body.

10. The occupying member as set forth in claim 7, wherein said piston engagement insertion space extends into said main body from said supporting face.

11. The occupying member as set forth in claim 7, wherein said piston engagement insertion space extends sufficiently into the main body so as to be in communication with said deformation accelerating space.

12. The occupying member as set forth in claim 7, wherein said liquid pressing face has a tapered portion.

13. The occupying member as set forth in claim 7, wherein said main body has an axial center, and wherein said supporting face has a plane perpendicular to the axial center of said main body.

* * * * *